United States Patent
Kelly et al.

(10) Patent No.: US 7,273,857 B2
(45) Date of Patent: *Sep. 25, 2007

(54) BENZIMIDAZOLIDINONE DERIVATIVES AS MUSCARINIC AGENTS

(75) Inventors: Nicholas Michael Kelly, Köbenhavn Ö (DK); Kristian Norup Koch, Köbenhavn Ö (DK); Bo-Ragnar Tolf, Köbenhavn Ö (DK)

(73) Assignee: ACADIA Pharmaceuticals Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/418,342

(22) Filed: May 3, 2006

(65) Prior Publication Data

US 2006/0205785 A1   Sep. 14, 2006

Related U.S. Application Data

(63) Continuation of application No. 10/262,517, filed on Sep. 30, 2002, now Pat. No. 7,087,593.

(60) Provisional application No. 60/326,754, filed on Oct. 2, 2001.

(51) Int. Cl.
*A01N 43/00* (2006.01)
*A61K 31/33* (2006.01)

(52) U.S. Cl. ............ 514/183; 514/210.21; 514/217.09; 514/321; 514/322; 514/367; 514/375; 514/394; 540/480; 540/603; 546/198; 546/199; 148/152; 148/217

(58) Field of Classification Search ............ 514/183, 514/210.21, 217.09, 321, 375, 394; 540/480, 540/603; 546/198, 199; 548/152, 217, 304.7
See application file for complete search history.

(56) References Cited

U.S. PATENT DOCUMENTS

| | | |
|---|---|---|
| 4,254,127 A | 3/1981 | Vandenberk et al. |
| 4,861,889 A | 8/1989 | Helsley et al. |
| 5,707,798 A | 1/1998 | Brann |
| 5,718,912 A | 2/1998 | Thomspon et al. |
| 5,726,188 A | 3/1998 | Takano et al. |

(Continued)

FOREIGN PATENT DOCUMENTS

EP   0 816 362 A1   1/1998

(Continued)

OTHER PUBLICATIONS

Bodick, et al., "Effects of xanomeline, a selective muscarinic receptor agonist, on cognitive function and behavioral symptoms in alzheimer disease", *Arch. Neurol.*, (1997) 54:465.

(Continued)

*Primary Examiner*—Johann Richter
*Assistant Examiner*—Chukwuma Nwaonicha
(74) *Attorney, Agent, or Firm*—Knobbe, Martens, Olson & Bear, LLP

(57) ABSTRACT

Benzimidazolidinone derivative compounds, which increase acetylcholine signaling or effect in the brain, and highly selective muscarinic agonists, particularly for the $M_1$ and/or $M_4$ receptor subtypes, pharmaceutical compositions comprising the same, as well as methods of treating psychosis using these compounds are disclosed.

9 Claims, 3 Drawing Sheets

U.S. PATENT DOCUMENTS

| | | | |
|---|---|---|---|
| 5,756,508 | A | 5/1998 | Thompson et al. |
| 5,789,425 | A | 8/1998 | Takano et al. |
| 6,586,435 | B2 | 7/2003 | Cereda et al. |
| 6,649,705 | B2 | 11/2003 | Ramesh |
| 6,815,458 | B2 | 11/2004 | Andersson et al. |
| 6,951,849 | B2 * | 10/2005 | Kelly et al. ............ 514/210.21 |
| 7,087,593 | B2 | 8/2006 | Kelly et al. |

FOREIGN PATENT DOCUMENTS

| | | |
|---|---|---|
| GB | 1017613 | 1/1966 |
| WO | WO96/13262 | 5/1996 |
| WO | WO97/16186 | 5/1997 |
| WO | WO97/16187 | 5/1997 |
| WO | WO97/16192 | 5/1997 |
| WO | WO99/32481 | 7/1999 |
| WO | WO 01/83472 A1 | 11/2001 |
| WO | WO 02/24662 | 3/2002 |
| WO | WO 03/028650 A2 | 4/2003 |

OTHER PUBLICATIONS

Bonner, et al., "Cloning and expression of the human and rat m5 muscarinic acetylcholine receptor genes", *Neuron*, (1988) 1:403.

Bonner, et al., "Identification of a family of muscarinic acetylcholine receptor genes", *Science*, (1987) 237:527.

Braüner-Osborne, et al., "Pharmacology of muscarinic acetylcholine receptor subtypes (m1-m5): high throughput assays in mammalian cells", *Eur. J. Pharamacol.*, (1996) 295:93-102.

Bymaster, et al., "Potential role of muscarinic receptors in schizophrenia", *Life Science*, (1999) 64:527.

Bymaster, et al., "Unexpected antipsychotic-like activity with the muscarinic receptor ligand (5R,6R)6-(3-propylthio-1,2,5-thiadiazol-4-yl)-1-azabicyclo[3.2.1]octane", *Eur. J. Pharmacol.*, (1998) 356:109.

Cakir, et al., "Synthesis and antinociceptive activity of some 3-subsitiuted benzothiazolone derivatives" *Il Farmaco*, (1999) 54:846.

Chahine, et al., "Functional expression and properties of the human skeletal muscle sodium channel", *Pfluegers Arch.*, (1994) 427:136-142.

Felder, et al., "Therapeutic opportunities for muscarinic receptors in the central nervous system", *J. Med. Chem.*, (2000) 43:4333.

Friedman, et al., "Pharmacologic strategies for augmenting cognitive performance in schizophrenia", *Biol. Psychiatry*, (1999) 45:1.

Itani, et al., "Novel Potent Antagonists of Human Neuropeptide Y Y5 Receptors", *Bioorganic & Medicinal Chemistry Letters*, (2002) 12:799-802.

Rowley, et al., "Current and novel approaches to the drag treatment of schizophrenia", *J. Med. Chem.*, (2001) 44:477.

Sauerberg, et al., "Muscarinic agonists with antipsychotic-like activity: structure-activity relationships of 1,2,5-thiadiazole analogues with functional dopamine antagonist activity", *J. Med. Chem.*, (1998) 41:4378.

Shannon, et al., "Xanomeline: a novel muscarinic receptor agonist with functional selectivity for M receptors", *J. Pharmacol. Exp. Ther.*, (1994) 269:271.

Shannon, et al., "Muscarinic receptor agonists, like dopamine receptors antagonist antipsychotics, inhibit conditioned avoidance response in rats", *J. Pharmacol. Exp. Ther.*, (1999) 290:901.

Shannon, et al., "Xanomeline, an $M_1/M_4$ preferring muscarinic cholinergic receptor agonist, produces antipsychotic-like activity in rats and mice", *Schizophrenia Res.*, (2000) 42:249.

Stormann, et al., "Molecular cloning and expression of a dopamine D2 receptor from Human retina", *Mol. Pharmacol.*, (1990) 37:1-6.

Supplementary European Search Report for Application No. EP 02 76 3824, Sep. 22, 2005.

Verma, et al., "Synthesis and Antibacterial Activity of Certain 3-Substituted Benzoxazolinones", J. Pharm. Sciences, (1968) 57(1):39-44.

Chemical Abstracts Reference No. 736980-05-5 as published in Vyas, K., et al., "Domperidone maleate," *Acta Crystallographica, Section C: Crystal Structure Communications*, 1999, C55(8), ii, IUC 9900104.

\* cited by examiner

BENZIMIDAZOLIDINONE DERIVATIVES AS MUSCARINIC AGENTS

RELATED APPLICATIONS

The present application is a continuation of U.S. application Ser. No. 10/262,517, filed Sep. 30, 2002 now U.S. Pat. No. 7,087,593, which claims priority to U.S. Provisional Patent Application Ser. No. 60/326,754, filed Oct. 2, 2001, both of which are incorporated herein by reference in their entirety.

FIELD OF THE INVENTION

Novel benzimidazolidinone derivatives have been prepared and identified as having high affinity for muscarinic $M_1$ and $M_4$ receptors. The treatment of mental disorders associated with increasing the activity of a cholinergic receptor using these novel compounds is anticipated. Moreover, these compounds also have dopamine $D_2$ antagonist activity, rendering them particularly interesting as antipsychotic agents.

BACKGROUND OF THE INVENTION

Muscarinic cholinergic receptors mediate the actions of the neurotransmitter acetylcholine in the central and peripheral nervous systems. Muscarinic receptors play a critical role in the central nervous system mediating higher cognitive functions, as well as in the peripheral parasympathetic nervous system where they mediate cardiac, respiratory, digestive, and endocrine and exocrine responses. Five distinct muscarinic receptor subtypes have been identified, $M_1$-$M_5$. The muscarinic $M_1$ receptor subtype is predominantly expressed in the cerebral cortex and is believed to be involved in the control of higher cognitive functions; the $M_2$ receptor is the predominant subtype found in heart and is involved in the control of heart rate; the $M_3$ receptor is widely expressed in many peripheral tissues and is believed to be involved in gastrointestinal and urinary tract stimulation as well as sweating and salivation; the $M_4$ receptor is present in brain and may be involved in locomotion; the $M_5$, receptor is present in the brain where its role is at present poorly defined. $M_1$ and $M_4$ have been particularly associated with the dopaminergic system.

Conditions associated with cognitive impairment, such as Alzheimer's disease, are accompanied by a reduction of acetylcholine content in the brain. This is believed to be the result of degeneration of cholinergic neurons of the basal forebrain, which widely innervate multiple areas of the brain, including the association cortices and hippocampus, that are critically involved in higher processes.

Efforts to increase acetylcholine levels have focused on increasing levels of choline, the precursor for acetylcholine synthesis, and on blocking acetylcholineesterase (AChE), the enzyme that metabolizes acetylcholine. Attempts to augment central cholinergic function through the administration of choline or phosphatidylcholine have not been successful. AChE inhibitors have shown therapeutic efficacy, but have been found to have frequent cholinergic side effects due to peripheral acetylcholine stimulation, including abdominal cramps, nausea, vomiting, and diarrhea. These gastrointestinal side effects have been observed in about a third of the patients treated. In addition, some AChE inhibitors, such as tacrine, have also been found to cause significant hepatotoxicity with elevated liver transaminases observed in about 30% of patients. The adverse effects of AChE inhibitors have severely limited their clinical utility.

The dopamine hypothesis of schizophrenia suggests that increased dopamine neurotransmission underlies the positive symptoms of the disease and is supported by the evidence that dopamine receptor blockade is effective in ameliorating such psychotic symptoms. Further, drugs that enhance dopamine neurotransmission in the brain cause psychotic-like episodes in man and exacerbate psychotic symptoms in schizophrenic patients. In animal studies, drugs that increase dopamine neurotransmission cause behavioural effects such as increased locomotion, climbing and deficits in prepulse inhibition. Known antipsychotics and dopamine receptor antagonists can block these behavioural effects. Unfortunately, dopamine receptor antagonists also cause severe extrapyramidal side effects in patients as predicted by induction of catalepsy in animal models. These extrapyramidal side effects include tremor, bradykinesia, akithesias, and tardive dyskinesias.

Due in part to these observations, the discovery of agents with $M_1$ receptor agonist activity has been sought after for the treatment of dementia. However, existing agents lack specificity in their actions at the various muscarinic receptor subtypes. Known $M_1$ muscarinic agonists such as arecoline have also been found to be weak agonists of $M_2$ as well as $M_3$ receptor subtypes and are ineffective in the treatment of cognitive impairment, due in large part to their dose-limiting $M_2$ and $M_3$ receptor mediated side effects.

Xanomeline (Shannon et al., *J. Pharmacol. Exp. Ther.* 1994, 269, 271; Shannon et al., *Schizophrenia Res*. 2000, 42, 249) is an $M_1$/$M_4$ preferring muscarinic receptor agonist with little or no affinity for dopamine receptors despite inhibiting A10 but not A9 dopamine cells. The thiadiazole derivative PTAC has been reported (Shannon et al., *European Journal of Pharmacology*, 1998, 356, 109) to have partial agonist effect at muscarinic $M_2$ and $M_4$ receptors and antagonist effect at muscarinic $M_1$, $M_3$, and $M_5$ receptors as well as exhibiting functional dopamine antagonism.

Recently, muscarinic agonists including xanomeline have been shown to be active in animal models with similar profiles to known antipsychotic drugs, but without causing catalepsy (Bymaster et al., *Eur. J. Pharmacol.* 1998, 356, 109, Bymaster et al., *Life Sci*. 1999, 64, 527, Shannon et al., *J. Pharmacol. Exp. Ther*. 1999, 290, 901, Shannon et al., *Schizophrenia Res*. 2000, 42, 249). Further, xanomeline was shown to reduce psychotic behavioural symptoms such as delusions, suspiciousness, vocal outbursts, and hallucinations in Alzheimer's disease patients (Bodick et al., *Arch. Neurol*. 1997, 54, 465), however treatment induced side effects that severely limit the clinical utility of this compound.

Analogues of 1,2,5-thiadiazole have been reported (Sauerberg et al., *J. Med. Chem*. 1998, 41, 4378) to have high affinity and selectivity for central muscarinic receptors as well as exhibiting functional dopamine antagonism despite lack of affinity for dopamine receptors.

The present investigators have focussed their efforts on the development of a molecule that simultaneously reduced the positive symptoms and improved the negative symptoms and the cognitive impairments associated with schizophrenia as a novel treatment of mental disorders. It is the intent of the present investigators to demonstrate that muscarinic $M_1$ and/or $M_4$ agonists with combined $D_2$ antagonist activity may possess superior antipsychotic efficacy without the side effects associated with high dose $D_2$ antagonism alone. The $D_2$ antagonist properties of these molecules may contribute to a reduction in the positive symptoms of this disease.

Based on distribution of $M_1$ and $M_4$ receptors in the cerebral cortex and hippocampus (the areas involved in higher order cognitive functions), the $M_1$ and/or $M_4$ agonist properties of these compounds may reduce the cognitive dulling and perhaps ameliorate other negative symptoms associated with schizophrenia. (Friedman, *Biol. Psychiatry*, 1999, 45, 1; Rowley, *J. Med. Chem.* 2001, 44, 477; Felder, *J. Med. Chem.* 2000, 43, 4333). This unique combination of central nervous system activities in one molecule is unprecedented and may lead to the development of an entirely new class of antipsychotic drugs, ones with the superior clinical properties without the limiting side-effect profile.

WO 99/32481 discloses derivatives including 1-substituted benzimidazolones and derivatives thereof. The compounds according to WO 99/32481 are intended for treatment of glaucoma, myopia, psychosis and various other conditions involving muscarinic receptors.

U.S. Pat. No. 4,254,127 discloses 1-(1-piperidinyl)alkyl-benzimidazolone derivatives wherein the piperidine is 4-substituted with aryl-alkyls, aryl-alkylcarbonyls, aryl-alkylcarbonyl derivatives, and aryl-alkoxides. The compounds according to U.S. Pat. No. 4,254,127 are reported to have psychotropic activity acting as serotonin antagonists.

U.S. Pat. No. 5,789,425 and U.S. Pat. No. 5,726,188 discloses 1-substituted imidazolidin-2-one derivatives with muscarinic $M_1$ activity. Benzimidazolidinone derivatives are not disclosed therein.

WO 96/13262 disclose benzimidazolidin-2-one derivatives 1-subsituted with a 4-piperidinyl moiety which in turn is 1-substituted. The compounds according to WO 96/13262 are reported to have anti-muscarinic activity intended for the treatment of myopia. Benzimidazolidin-2-one derivatives 1-subsituted with moieties other than a 4-piperidinyl group is not disclosed.

WO 97/16192, WO 97/16187 and U.S. Pat. No. 5,756,508 disclose novel 1,3-dihydro[1-(1-heteroarylpiperidine-4-yl) piperidine-4-yl]-2H-benzimidazolones. The compounds according to WO 97/16192, WO 97/16187 and U.S. Pat. No. 5,756,508 are reported to have antimuscarinic activity used for treatment and/or prevention of myopia.

WO 97/16186 and U.S. Pat. No. 5,718,912 disclose 1-[cycloalkylpiperidin-4-yl]-2H-benzimidazolones as selective muscarinic agonists of the $M_2$ subtype with low activity at the $M_3$ subtype, and when utilised for glaucoma therapy have fewer side effects than pilocarpine therapy.

Cakir, B et al. describes the synthesis and antinociceptive activity of some 1-(3-piperidinopropyl)benzothiazolone derivatives in *Farmaco*, 1999, 54, 846.

There is a need in the art to provide compounds that increase acetylcholine signaling or effect in the brain. Specifically there is a need for muscarinic agonists that are active at various muscarinic receptor subtypes in the central and peripheral nervous system. There is a further need to develop more highly selective muscarinic agonists, such as $M_1$ and/or $M_4$ selective agents, both as pharmacological tools and as potential therapeutic agents. Moreover, there is a need for compounds aimed at the approach of treating psychosis using compounds which has a combined muscarinic agonist and dopamine antagonist profile.

SUMMARY OF THE INVENTION

The present invention seeks to provide compounds which increase acetylcholine signaling or effect in the brain, and highly selective muscarinic agonists, particularly for the $M_1$ and/or $M_4$ receptor subtypes as well as providing compounds aimed at the approach of treating psychosis using compounds which has a combined muscarinic agonist and dopamine antagonist profile.

In a first aspect, the present invention relates to a compound of Formula I

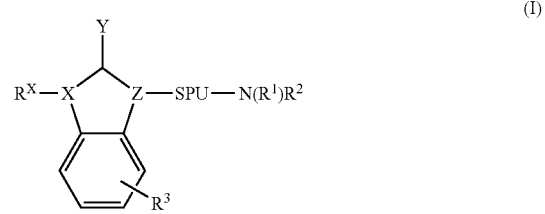

or a pharmaceutically acceptable salt or prodrug thereof, wherein

X is selected from the group consisting of C, O, N and S

Z is selected from the group consisting of CH and N

Y is selected from the group consisting of =O, =N and =S or tautomers thereof, such as Y-alkylated tautomers;

SPU is a spacer unit providing a distance d between Z and N wherein

—SPU— is a biradical selected from the group consisting of —$(CR^6R^7)_n$—A— and —$C_{3-8}$-cycloalkyl- wherein n is in the range 1 to 5, such as 1, 2, 3, 4, or 5 and A is absent or an optionally substituted —$C_{3-8}$-cycloalkyl;

N together with $R^1$ and $R^2$ form a heterocyclic ring wherein said heterocyclic ring is selected from the group consisting of perhydroazocine, perhydroazepine, piperidine, pyrrolidine, azetidine, aziridine and 8-azabicyclo[3.2.1]octane and wherein the heterocyclic ring is substituted with one or more substituents $R^4$ selected from the group consisting of hydroxy, halogen, $C_{1-8}$-alkyl, $C_{3-8}$-cycloalkyl, $C_{1-8}$-alkoxy, $C_{1-8}$-alkylcarbonyl, $C_{1-8}$-alkylidene, $C_{2-8}$-alkenyl, $C_{2-8}$-alkynyl, $C_{1-6}$-alkyloxyimino, and $C_{1-6}$-alkyloxyamino each of which may be optionally substituted with a substituent $R^5$ and wherein at least one of said substituents $R^4$ is $R^4$ selected from the group consisting of $C_{1-8}$-alkyl, $C_{3-8}$-cycloalkyl, $C_{1-8}$-alkoxy, $C_{1-8}$-alkylcarbonyl, $C_{1-8}$-alkylidenec $C_{1-8}$-alkyloxyimino, and $C_{1-8}$-alkyloxyamino each of which may be optionally substituted with a substituent $R^5$;

$R^5$ is selected from the group consisting of hydrogen, halogen, hydroxy, $C_{1-8}$-alkyl, $C_{1-8}$-alkoxy, $C_{3-8}$-cycloalkyl, $C_{3-8}$-heterocyclyl, $C_{1-8}$-alkylcarbonyl, $C_{1-8}$-alkylidene, $C_{2-8}$-alkenyl and $C_{2-8}$-alkynyl;

$R^X$ may be absent or selected from the group consisting of hydrogen, optionally substituted $C_{1-8}$-alkyl, optionally substituted $C_{3-8}$-cycloalkyl, optionally substituted $C_{2-8}$-alkenyl, optionally substituted $C_{2-8}$-alkynyl, optionally substituted aryl, optionally substituted heteroaryl $CH_2$—$N(R^5)(R^5)$, $CH_2$—$OR^5$, $CH_2$—$SR^5$, $CH_2$—O—$C(=O)R^5$, $CH_2$—O—$C(=S)R^5$;

$R^3$ may be present 0-4 times and selected from the group consisting of halogen, hydroxy, optionally substituted $C_{1-8}$-alkyl, $C_{1-8}$-alkoxy, optionally substituted $C_{1-8}$-alkylidene, optionally substituted $C_{2-8}$-alkenyl, optionally substituted $C_{2-8}$-alkynyl optionally substituted aryl, optionally substituted heteroaryl, optionally substituted $C_{3-8}$-cycloalkyl, optionally substituted $C_{3-8}$-heterocyclyl, and optionally substituted $C_{1-8}$-alkylcarbonyl;

each $R^6$ and each $R^7$ is independently selected from the group consisting of hydrogen, halogen, hydroxy, optionally substituted $C_{1-8}$-alkyl, $C_{1-8}$-alkoxy, optionally substituted $C_{1-8}$-alkylidene, optionally substituted $C_{2-8}$-alkenyl, optionally substituted $C_{2-8}$-alkynyl optionally substituted aryl, optionally substituted heteroaryl, optionally substituted $C_{3-8}$-cycloalkyl, optionally substituted $C_{3-8}$-heterocyclyl, and optionally substituted $C_{1-8}$-alkylcarbonyl.

A second aspect of the invention relates to a method of increasing an activity of a cholinergic receptor comprising contacting the cholinergic receptor or a system containing the cholinergic receptor with an effective amount of at least one compound of Formula I.

An increase in activity of the cholinergic receptor and the cholinergic system is, as discussed supra, associated to the activity of anti-psychotics. Accordingly, further aspects of the present invention relate to a method of treating or preventing a mental disorder in a mammal, comprising the administration of an effective amount of a compound of Formula I and to the use of a compound of Formula I, a pharmaceutically acceptable salt thereof, or a pharmaceutical composition containing either entity, for the preparation of a medicament for the prophylactic or curative treatment of psychosis or alleviation of symptoms of psychosis. In the context of the present invention a mammal may be selected from the group consisting of mice, rats, rabbits, guinea pigs, dogs, cats, sheep, goats, cows, primates, such as monkeys, chimpanzees, and apes, and humans. Most preferably, the mammal is a human.

Aspects of the invention relate to compounds of Formula I for use as selective modulators of $M_1$ and/or $M_4$ muscarinic receptors for the treatment of disorders associated with muscarinic receptors and especially with said receptor subtypes.

As stated, compounds of Formula I have surprisingly been found to have selectivity for the $M_1$ and $M_4$ muscarinic receptor subtypes. Therapeutic advantages may be derived from this selectivity. Further therapeutic advantages may be derived from the concomitant muscarinic $M_1$ and $M_4$ agonist activity and dopaminergic $D_2$ antagonist activity.

Compounds of Formula I, by the modulation of muscarinic receptors may be implicated in the control of amyloid precursor processing, in particular by the activation of the $M_1$ receptor. Thus, a further aspect of the present invention relates to a method of modulating or preventing the progression or formation of amyloid plaques in an individual susceptible to or affected by Alzheimer's Disease by administering an effective amount of a compound of Formula I, said effective amount sufficient to modulate amyloid precursor protein processing.

DETAILED DESCRIPTION OF THE PREFERRED EMBODIMENTS

Figure 1:
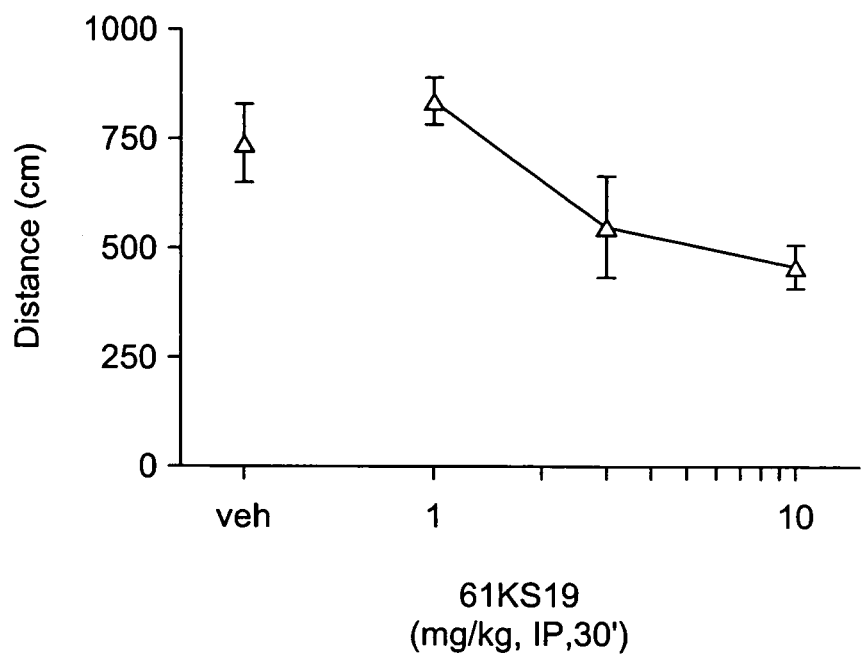
FIG. 1 is a graph depicting the reduction of spontaneous locomotor activity in mice with the administration of 10 mg/kg i.p. of 61KS19.
Figure 2:
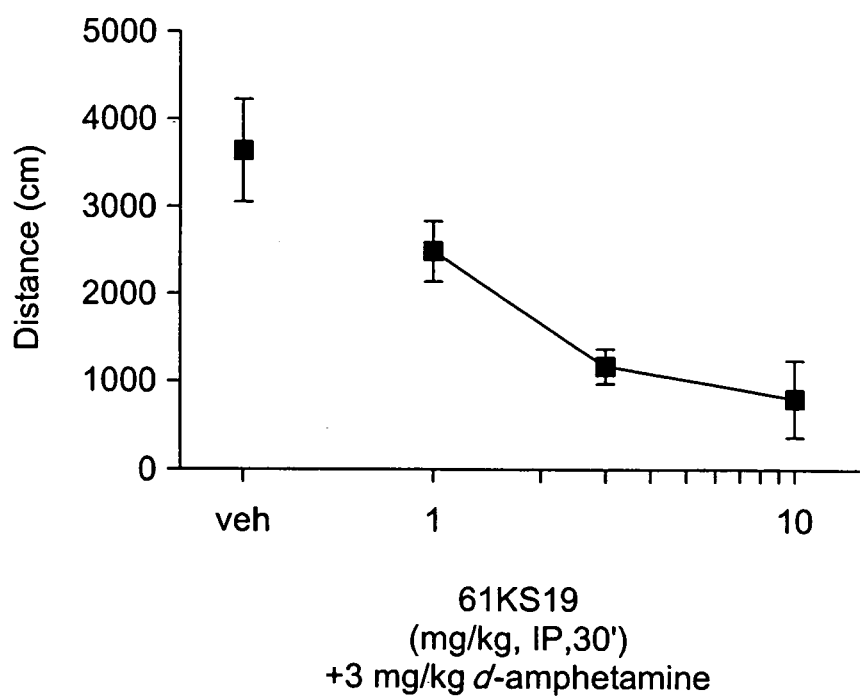
FIG. 2 is a graph that shows the reduction of amphetamine-induced hyperactivity in mice with the administration of 3 and 10 mg/kg i.p. of 61KS19
Figure 3:
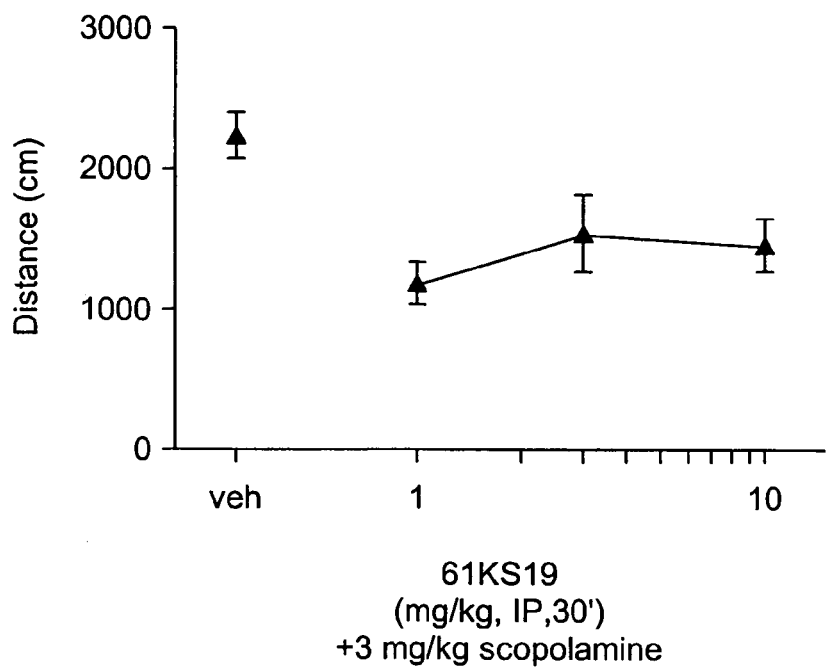
FIG. 3 is a graph that shows the reduction of scopolamine-induced hyperactivity in mice with the administration of 1, 3 and 10 mg/kg i.p. of 61KS19
Figure 4:
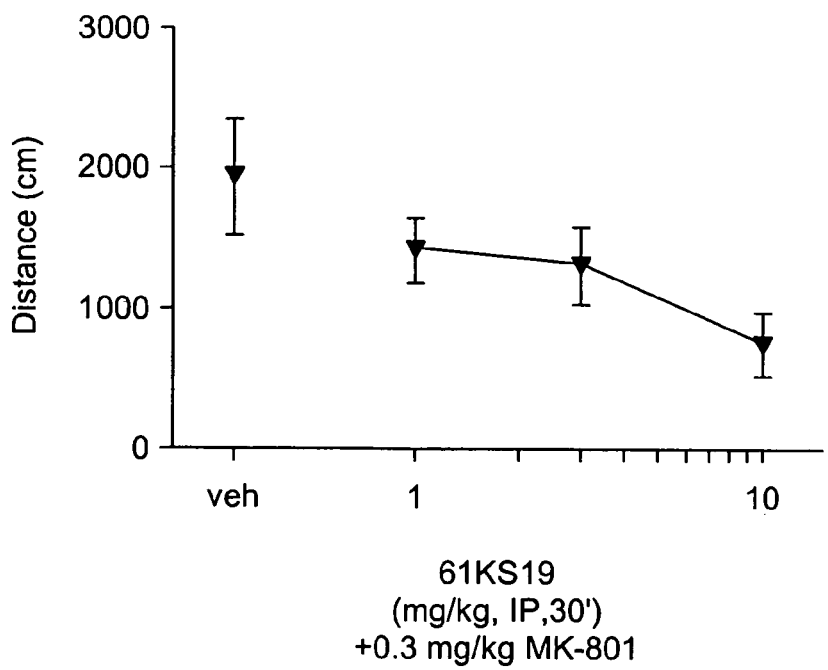
FIG. 4 is a graph that shows the reduction of MK-801-induced hyperactivity in mice with the administration of 10 mg/kg i.p. of 61KS19.
Figure 5:
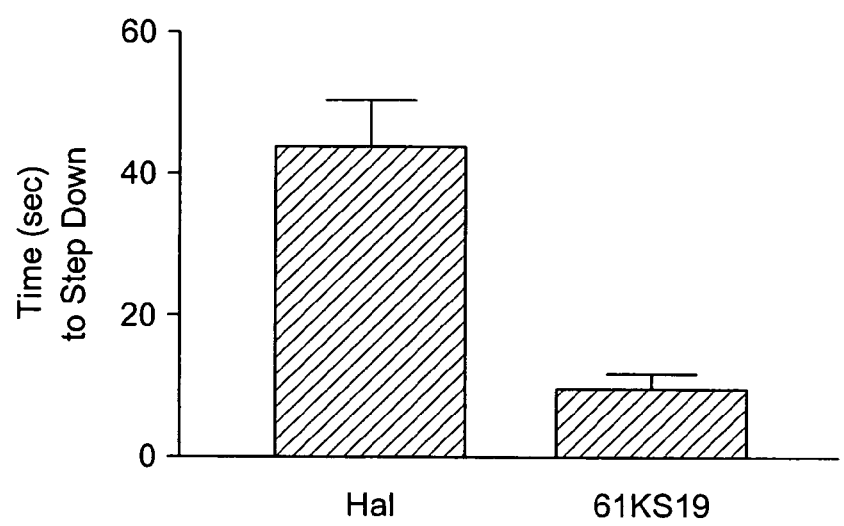
FIG. 5 depicts the result of a comparison between haloperidol and 61KS19, and shows that unlike haloperidol, 61KS19 (10 mg/kg i.p.) failed to induce catalepsy.

In a first aspect, the present invention relates to a compound of Formula I

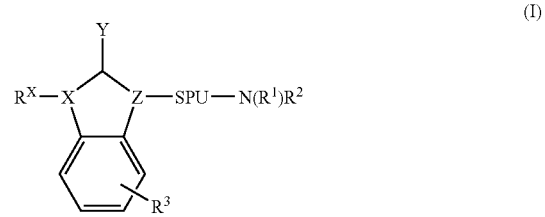

(I)

or a pharmaceutically acceptable salt or prodrug thereof, wherein

X is selected from the group consisting of C, O, N and S

Z is selected from the group consisting of C and N

Y is selected from the group consisting of =O, =N and =S or tautomers thereof, such as Y-alkylated tautomers;

SPU is a spacer unit providing a distance d between Z and N wherein

—SPU— is a biradical selected from the group consisting of —$(CR^6R^7)_n$—A— and —$C_{3-8}$-cycloalkyl- wherein n is in the range 1 to 5, such as 1, 2, 3, 4, or 5 and A is absent or an optionally substituted —$C_{3-8}$-cycloalkyl;

N together with $R^1$ and $R^2$ form a heterocyclic ring wherein said heterocyclic ring is selected from the group consisting of perhydroazocine, perhydroazepine, piperidine, pyrrolidine, azetidine, aziridine and 8-azabicyclo[3.2.1]octane and wherein the heterocyclic ring is substituted with one or more substituents $R^4$ selected from the group consisting of hydroxy, halogen, $C_{1-8}$-alkyl, $C_{3-8}$-cycloalkyl, $C_{1-8}$-alkoxy, $C_{1-8}$-alkylcarbonyl, $C_{1-8}$-alkylidene, $C_{2-8}$-alkenyl, $C_{2-8}$-alkynyl, $C_{1-6}$-alkyloxyimino, and $C_{1-6}$-alkyloxyamino each of which may be optionally substituted with a substituent $R^5$ and wherein at least one of said substituents $R^4$ is $R^{4'}$ selected from the group consisting of $C_{1-8}$-alkyl, $C_{3-8}$-cycloalkyl, $C_{1-8}$-alkoxy, $C_{1-8}$-alkylcarbonyl, $C_{1-8}$-alkylidene $C_{1-8}$-alkyloxyimino, and $C_{1-8}$-alkyloxyamino each of which may be optionally substituted with a substituent $R^5$;

$R^5$ is selected from the group consisting of hydrogen, halogen, hydroxy, $C_{1-8}$-alkyl, $C_{3-8}$-cycloalkyl, $C_{3-8}$-heterocyclyl, $C_{1-8}$-alkylcarbonyl, $C_{1-8}$-alkylidene, $C_{2-8}$-alkenyl and $C_{2-8}$-alkynyl;

$R^x$ may be absent or selected from the group consisting of hydrogen, optionally substituted $C_{1-8}$-alkyl, optionally substituted $C_{3-8}$-cycloalkyl, optionally substituted $C_{2-8}$-alkenyl, optionally substituted $C_{2-8}$-alkynyl, optionally substituted aryl, optionally substituted heteroaryl, CH$_2$—N(R$^5$)(R$^5$), CH$_2$—OR$^5$, CH$_2$—SR$^5$, CH$_2$—O—C(=O)R$^5$, CH$_2$—O—C(=S)R$^5$;

R$^3$ may be present 0-4 times and selected from the group consisting of halogen, hydroxy, optionally substituted C$_{1-8}$-alkyl, C$_{1-8}$-alkoxy, optionally substituted C$_{1-8}$-alkylidene, optionally substituted C$_{2-8}$-alkenyl, optionally substituted C$_{2-8}$-alkynyl optionally substituted aryl, optionally substituted heteroaryl, optionally substituted C$_{3-8}$-cycloalkyl, optionally substituted C$_{3-8}$-heterocyclyl, and optionally substituted C$_{1-8}$-alkylcarbonyl;

each R$^6$ and each R$^7$ is independently selected from the group consisting of hydrogen, halogen, hydroxy, optionally substituted C$_{1-8}$-alkyl, C$_{1-8}$-alkoxy, optionally substituted C$_{1-8}$-alkylidene, optionally substituted C$_{2-8}$-alkenyl, optionally substituted C$_{2-8}$-alkynyl optionally substituted aryl, optionally substituted heteroaryl, optionally substituted C$_{3-8}$-cycloalkyl, optionally substituted C$_{3-8}$-heterocyclyl, and optionally substituted C$_{1-8}$-alkylcarbonyl.

The term "pharmaceutically acceptable salt" refers to a formulation of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

The term "selective" or "selectivity" is intended to mean the ability of a compound to generate a desired response from a particular receptor type, subtype, class or subclass while generating less or little response from other receptor types. "Selective" or "selectivity" of an M$_1$ or M$_4$ muscarinic agonist compound is intended to mean the ability of a compound to increase the activity of the M$_1$ or M$_4$ muscarinic receptor, respectively, while causing non-substantial, little or no increase in the activity of other subtypes including M$_3$ and M$_5$ subtypes, and preferably the M$_2$ subtype. Compounds of the presents invention may also show selectivity toward both M$_1$ and M$_4$ receptors, i.e. increase the activity of both the M$_1$ and M$_4$ muscarinic receptors, while causing little or no increase in the activity of other subtypes including M$_3$ and M$_5$ subtypes, and preferably the M$_2$ subtype.

In the present context, the term "C$_{1-8}$-alkyl" is intended to mean a linear or branched saturated hydrocarbon chain wherein the longest chains has from one to eight carbon atoms, such as methyl, ethyl, n-propyl, isopropyl, n-butyl, isobutyl, sec-butyl, tert-butyl, pentyl, isopentyl, neopentyl, hexyl, heptyl and octyl. A branched hydrocarbon chain is intended to mean a C$_{1-8}$-alkyl substituted at any carbon with a hydrocarbon chain.

In the present context, the term "C$_{2-8}$-alkenyl" is intended to mean a linear or branched hydrocarbon group having from two to eight carbon atoms and containing one or more double bonds. Illustrative examples of C$_{2-8}$-alkenyl groups include allyl, homo-allyl, vinyl, crotyl, butenyl, pentenyl, hexenyl, heptenyl and octenyl. Illustrative examples of C$_{2-10}$-alkenyl groups with more than one double bond include butadienyl, pentadienyl, hexadienyl, heptadienyl, hexatrienyl, heptatrienyl and octatrienyl groups as well as branched forms of these. The position of the unsaturation (the double bond) may be at any position along the carbon chain.

In the present context, the term "C$_{1-8}$-alkylidene" is intended to mean a linear or branched hydrocarbon chain radical wherein the longest chain has from one to eight carbon atoms and an unsaturated bond at the radical position. Bonds further than the radical position may also be unsaturated.

In the present context the term "C$_{2-8}$-alkynyl" is intended to mean linear or branched hydrocarbon groups containing from two to eight carbon atoms and containing one or more triple bonds. Illustrative examples of C$_{2-8}$-alkynyl groups include ethynyl, propynyl, butynyl, pentynyl, hexynyl, heptynyl and octynyl groups as well as branched forms of these. The position of unsaturation (the triple bond) may be at any position along the carbon chain. More than one bond may be unsaturated such that the "C$_{2-8}$-alkynyl" is a di-yne or enedi-yne as is known to the person skilled in the art.

In the present context the term "C$_{3-8}$-cycloalkyl" is intended to cover three-, four-, five-, six- seven-, and eight-membered rings comprising carbon atoms only whereas the term "heterocyclyl" is intended to mean three-, four-, five-, six- seven-, and eight-membered rings wherein carbon atoms together with from 1 to 3 heteroatoms constitute said ring. The heteroatoms are independently selected from oxygen, sulphur, and nitrogen.

C$_{3-8}$-cycloalkyl and heterocyclyl rings may optionally contain one or more unsaturated bonds situated in such a way, however, that an aromatic π-electron system does not arise.

Illustrative examples of preferred "C$_{3-8}$-cycloalkyl" are the carbocycles cyclopropane, cyclobutane, cyclopentane, cyclopentene, cyclopentadiene, cyclohexane, cyclohexene, 1,3-cyclohexadiene, 1,4-cyclohexadiene, cycloheptane, cycloheptene, 1,2-cycloheptadiene, 1,3-cycloheptadiene, 1,4-cycloheptadiene and 1,3,5 cycloheptatriene.

Illustrative examples of "heterocyclyls" are the heterocycles 2H-thipyran, 3H-thipyran, 4H-thipyran, tetrahydrothiopyran, 2H-pyran, 4H-pyran, tetrahydropyran, piperidine, 1,2-dithiin, 1,2-dithiane, 1,3-dithiin, 1,3-dithiane, 1,4-dithiin, 1,4-dithiane, 1,2-dioxin, 1,2-dioxane, 1,3-dioxin, 1,3-dioxane, 1,4-dioxin, 1,4-dioxane, piperazine, 1,2-oxathiin, 1,2-oxathiane, 4H-1,3-oxathiin, 1,3-oxathiane, 1,4-oxathiin, 1,4-oxathiane, 2H-1,2-thiazine, tetrahydro-1,2-thiazine, 2H-1,3-thiazine, 4H-1,3-thiazine, 5,6-dihydro-4H-thiazine, 4H-1,4-thiazine, tetrahydro-1,4-thiazine, 2H-1,2- oxazine, 4H-1,2-oxazine, 6H-1,2-oxazine, 2H1,3-oxazine, 4H-1,3-oxazine, 4H-1,4-oxazine, maleimide, succinimide, dioxopiperazine, hydantoin, morpholine, trioxane, 4H-1,2,3-trithiin, 1,2,3-trithiane, 1,3,5-trithiane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,2-dioxole, 1,2-dioxolane, 1,3-dioxole, 1,3-dioxolane, 3H-1,2-dithiole, 1,2-dithiolane, 1,3-dithiole, 1,3-dithiolane, isoxazoline, isoxazolidine, oxazoline, oxazolidine, thiazoline, thiozolidine, 3H-1,2-oxathiole, 1,2-oxathiolane, 5H-1,2-oxathiole, 1,3-oxathiole, 1,3-oxathiolane, 1,2,3-trithiole, 1,2,3-trithiolane, 1,2,4-trithiolane, 1,2,3-trioxole, 1,2,3-trioxolane, 1,2,4-trioxolane, 1,2,3-triazoline and 1,2,3-triazolidine. Binding to the heterocycle may be at the position of the heteroatom or via carbon atom of the heterocycle.

In the present context the term "aryl" is intended to mean a carbocyclic aromatic ring or ring system. Moreover, the term "aryl" includes fused ring systems wherein at least two aryl rings, or at least one aryl and at least one $C_{3-8}$-cycloalkyl, or at least one aryl and at least one heterocyclyl, share at least chemical bond. Illustrative examples of "aryl" rings include optionally substituted phenyl, naphthalenyl, phenanthrenyl, anthracenyl, acenaphthylenyl, tetralinyl, fluorenyl, indenyl, indolyl, coumaranyl, coumarinyl, chromanyl, isochromanyl, and azulenyl. A preferred aryl group is phenyl.

In the present context, the term "heteroaryl" is intended to mean an aryl group where one or more carbon atoms in an aromatic ring have been replaced with one or more heteroatoms selected from the group comprising nitrogen, sulphur, phosphorous and oxygen.

Furthermore, in the present context, the term "heteroaryl" comprises fused ring systems wherein at least one aryl ring and at least one heteroaryl ring, at least two heteroaryls, at least one heteroaryl and at least one heterocyclyl, or at least one heteroaryl and at least one $C_{3-8}$-cycloalkyl share at least one chemical bond, such as one or two chemical bonds.

Illustrative examples of a heteroaryl may be selected from the group comprising furanyl, thienyl, pyrrolyl, phenoxazonyl, oxazolyl, thiazolyl, isothiazolyl, imidazolyl, pyrazolyl, isoxazolyl, imidazolyl isothiazolyl, oxadiazolyl, furazanyl, triazolyl, thiadiazolyl, piperidinyl, pyridinyl, pyridazinyl, pyrimidinyl, pyrazinyl, pyrazolyl and triazinyl, isoindolyl, indolinyl, benzofuranyl, benzothiophenyl, benzopyrazolyl, indazolyl, benzimidazolyl, benzthiazolyl, purinyl, quinolizinyl, quinolinyl, isoquinolinyl, cinnolinyl, phthalazinyl, quinazolinyl, quinoxalinyl, naphthyridinyl, pteridinylthienofuranyl, carbazolyl, acridinyl, phenazinyl, phenothiazinyl, phenoxazinyl and thianthrenyl.

When used herein the term "$C_{1-8}$-alkoxy" is intended to mean $C_{1-8}$-alkyl-oxy such as methoxy, ethoxy, n-propoxy, isopropoxy, n-butoxy, isobutoxy, sec-butoxy, tert-butoxy, pentoxy, isopentoxy, neopentoxy and hexoxy The term "halogen" includes fluorine, chlorine, bromine and iodine.

In the present context, i.e. in connection with the terms "aryl", "heteroaryl", "$C_{3-8}$-cycloalkyl", "heterocyclyl", "$C_{1-8}$-alkyl", "$C_{1-8}$-alkoxy", "$C_{2-8}$-alkenyl", and "$C_{2-8}$-alkynyl", the term "optionally substituted" is intended to mean that the group in question may be substituted one or several times, such as 1 to 5 times, preferably 1 to 3 times, most preferably 1 to 2 times, with one or more groups selected from $C_{1-8}$-alkyl, $C_{1-8}$-alkoxy, oxo (which may be represented in the tautomeric enol form), carboxyl, amino, hydroxy (which when present in an enol system may be represented in the tautomeric keto form), nitro, sulphono, sulphanyl, $C_{1-8}$-carboxyl, $C_{1-8}$-alkoxycarbonyl, $C_{1-8}$-alkylcarbonyl, formyl, aryl, aryloxy, aryloxycarbonyl, arylcarbonyl, heteroaryl, amino, mono- and di($C_{1-8}$-alkyl)amino; carbamoyl, mono- and di($C_{1-8}$-alkyl)aminocarbonyl, amino-$C_{1-8}$-alkyl-aminocarbonyl, mono- and di($C_{1-8}$-alkyl)amino-$C_{1-8}$-alkyl-aminocarbonyl, $C_{1-8}$-alkylcarbonylamino, cyano, guanidino, carbamido, $C_{1-8}$-alkanoyloxy, $C_{1-8}$-alkylsulphonyloxy, dihalogen-$C_{1-8}$-alkyl, trihalogen-$C_{1-8}$-alkyl, halogen, where aryl and heteroaryl representing substituents may be substituted 1-3 times with $C_{1-8}$-alkyl, $C_{1-8}$-alkoxy, nitro, cyano, hydroxy, amino or halogen. In general, the above substituents may be susceptible to further optional substitution.

The term "salts" is intended to mean pharmaceutically acceptable acid addition salts obtainable by treating the base form of a functional group, such as an amine, with appropriate acids such as inorganic acids, for example hydrohalic acids; typically hydrochloric, hydrobromic, hydrofluoric, or hydroiodic acid; sulfuric acid; nitric acid; phosphoric acid and the like; or organic acids, for example acetic, propionic, hydroacetic, 2-hydroxypropanoic acid, 2-oxopropanoic acid, ethandioic, propanedioic, butanedioic, (Z)-2-butenedioic, (E)-butenedioic, 2-hydroxybutanedioic, 2,3-dihydroxybutanedioic, 2-hydroxy-1,2,3-propanetricarboxylic, methane sulfonic, ethanesulfonic, benzenesulfonic, 4-methylbenzenesulfonic acid, cyclohexanesulfamic, 2-hydoxybenzoic, 4-amino-2-hydroxybenzoic, ethanedisulfonic, and other acids known to the skilled practitioner.

In certain embodiments of the present invention, the spacer unit SPU comprises a number of optionally substituted methylene groups $CR^6R^7$. It is understood by the phrase "each $R^6$ and each $R^7$ is optionally and independently selected" that not all $R^6$ groups may be identical and not all $R^7$ groups may be identical. Thus, each substituted methylene group may have an $R^6$ and an $R^7$ that is different than any other $R^6$ or $R^7$ substituents on other methylene groups. In some embodiments, some of $R^6$ or $R^7$ substituents may be identical in one or more methylene groups.

In one embodiment, the present invention relates to a compound of Formula I, wherein
X is selected from the group consisting of O, N and S;
Z is N
Y is =O or tautomers thereof;
SPU is a spacer unit providing a distance d between Z and N wherein —SPU— is —$(CR^6R^7)_n$—A—, n is 3, and A is absent;
N together with $R^1$ and $R^2$ form a piperidine ring substituted with one or more substituents $R^4$ selected from the group consisting of hydroxy, halogen, $C_{1-8}$-alkyl, $C_{3-8}$-cycloalkyl, $C_{1-8}$-alkoxy, $C_{1-8}$-alkylcarbonyl, $C_{1-8}$-alkylidene, $C_{2-8}$-alkenyl, $C_{2-8}$-alkynyl, $C_{1-6}$-alkyloxyimino, and $C_{1-6}$-alkyloxyamino each of which may be optionally substituted with a substituent $R^5$
and wherein at least one of said substituents $R^4$ is $R^{4'}$ selected from the group consisting of $C_{1-8}$-alkyl, $C_{3-8}$-cycloalkyl, $C_{1-8}$-alkoxy, $C_{1-8}$-alkylidenec, each of which may be optionally substituted with a substituent $R^5$;
$R^5$ is selected from the group consisting of hydrogen, halogen, hydroxy, $C_{1-8}$-alkyl, $C_{1-8}$-alkoxy, $C_{3-8}$-cycloalkyl, $C_{3-8}$-heterocyclyl, $C_{1-8}$-alkylcarbonyl, $C_{1-8}$-alkylidene, $C_{2-8}$-alkenyl and $C_{2-8}$-alkynyl;
$R^X$ may be absent or selected from the group consisting of hydrogen, optionally substituted $C_{1-8}$-alkyl;
$R^3$ may be present 0-4 times and selected from the group consisting of halogen, hydroxy, optionally substituted $C_{1-8}$-alkyl, $C_{1-8}$-alkoxy, optionally substituted $C_{1-8}$- alkylidene, optionally substituted $C_{2-8}$-alkenyl, optionally substituted $C_{2-8}$-alkynyl optionally substituted aryl, optionally substituted heteroaryl, optionally substituted $C_{3-8}$-cycloalkyl, optionally substituted $C_{3-8}$-heterocyclyl, and optionally substituted $C_{1-8}$-alkylcarbonyl; and each $R^6$ and each $R^7$ is optionally and independently selected from the group consisting of hydrogen, halogen, hydroxy, optionally substituted $C_{1-8}$-alkyl, $C_{3-8}$-cycloalkyl, In certain embodiments of compound of Formula I, Z is N (nitrogen). Thus, the distance d relates to the distance between the ring nitrogen atom and the nitrogen atom of $N(R^1)R^2$.

In compounds of Formula I, X may be selected from the group consisting of N, S, and O, preferably N and O. In a preferred embodiment X and Z are both N.

In a suitable embodiment of compounds of Formula I, —Y is selected from the group consisting of =O, =S and tautomers thereof. Tautomers of the carbonyl and thiocarbonyl moiety are known to the person skilled in the art and are isomers involving migration of the pi system from the exo-cyclic to the endocyclic position. The enolic or thio-enolic derivative may be O— or S-alkylated in a manner known to the person skilled in the art.

In a preferred embodiment however, —Y is =O or its tautomer. Preferably —Y is =O. Thus, in a combination of preferred embodiments, X is N, —Y is =O, and Z is N, resulting in a benzimidazolidinone ring system.

The moiety Z is substituted with a spacer unit (SPU). SPU provides a distance d between Z and N. The distance d is formed from a short, optionally substituted aliphatic chain, $(CR^6R^7)_n$, wherein n is in the range 1 to 5, such as 1, 2, 3, 4 or 5 or from said chain and a —$C_{3-8}$-cycloalkyl- ring. Thus, d may be defined in terms of through-bond distances between Z and N of $N(R^1)R^2$ or a combination of through-bond and through-space distances between Z and N of $N(R^1)R^2$. Thus, —SPU— is a biradical selected from the group consisting of —$(CR^6R^7)_n$—A— and —$C_{3-8}$-cycloalkyl- wherein n is in the range 1 to 5 and A is absent or an optionally substituted —$C_{3-8}$-cycloalkyl. Preferably, n is in the range 2 to 5, most preferably 2 to 4, such as 2, 3, or 4.

In an interesting embodiment of the present invention, the $C_{3-8}$-cycloalkyl- ring of —SPU— is an optionally substituted cyclohexylene. Thus, —SPU— may be selected from the group consisting of —$(CR^4R^5)_n$—A— and an optionally substituted cyclohexylene wherein n is in the range 1 to 5, preferably 2 to 5 and A is absent or an optionally substituted cyclohexylene.

In an interesting embodiment, —SPU— is an ethylene, propylene, butylene, or pentylene biradical, preferably ethylene, propylene or butylene, each of which may be optionally substituted. Alternatively, —SPU— is a cylcohexylene biradical.

The cyclohexylene of —SPU— may be an optionally substituted 1,3-cyclohexylene or an optionally substituted 1,4-cyclohexylene, preferably an optionally substituted 1,4-cyclohexylene. That is to say that in the embodiment where SPU is or comprises of a cyclohexylene, said cyclohexylene is preferably bond to Z and N at positions 1 and 4 or 1 and 3 of said ring.

As stated, N together with $R^1$ and $R^2$ form a heterocyclic ring wherein said heterocyclic ring is selected from the group consisting of perhydroazocine, perhydroazepine, piperidine, pyrrolidine, azetidine, aziridine and 8-azabicyclo [3.2.1]octane. In a preferred embodiment, $N(R^1)R^2$ is selected from the group consisting of a piperidine, pyrrolidine, and azetidine, most preferably piperidine and pyrrolidine, particularly preferably piperidine.

The heterocyclic ring formed by N together with $R^1$ and $R^2$ is substituted with one or more substituents $R^4$ selected from the group consisting of hydroxy, halogen, $C_{1-8}$-alkyl, $C_{3-8}$-cycloalkyl, $C_{1-8}$-alkoxy, $C_{1-8}$-alkylcarbonyl, $C_{1-8}$-alkylidene, $C_{2-8}$-alkenyl, $C_{2-8}$-alkynyl, $C_{1-8}$-alkyloxyimino, and $C_{1-8}$-alkyloxyamino each of which may be optionally substituted with a substituent $R^5$ and at least one of said substituents $R^4$ is $R^{4'}$ selected from the group consisting of $C_{1-8}$-alkyl, $C_{3-8}$-cycloalkyl, $C_{1-8}$-alkoxy, $C_{1-8}$-alkylcarbonyl, $C_{1-8}$-alkylidene, $C_{2-8}$-alkenyl, $C_{2-8}$-alkynyl, $C_{1-8}$-alkyloxyimino, and $C_{1-8}$-alkyloxyamino each of which may be optionally substituted with a substituent $R^5$.

Thus, the heterocyclic ring formed by N together with $R^1$ and $R^2$ may be substituted with one or more substituent $R^4$ wherein at least one $R^4$ is $R^{4'}$.

As stated, the heterocyclic ring formed by N together with $R^1$ and $R^2$ is substituted with one more substituent $R^4$. In a preferred embodiment, the heterocyclic ring is selected from the group comprising of a piperidine with at least one substituent $R^{4'}$ in the 2-position, a piperidine with at least one substituent $R^{4'}$ in the 3-position, a piperidine with at least one substituent $R^{4'}$ in the 4-position, a pyrrolidine with at least one substituent $R^{4'}$ in the 3-position, an azetidine with at least one substituent $R^{4'}$ in the 3-position and an aziridine with at least one substituent $R^{4'}$ in the 2-position.

In a particularly suitable embodiment, $N(R^1)R^2$ is selected from the group consisting of a piperidine with at least one substituent $R^{4'}$ in the 2-position, a piperidine with at least one substituent $R^4$ in the 3-position, a piperidine with at least one substituent $R^{4'}$ in the 4-position, most preferably consisting of a piperidine with at least one substituent $R^{4'}$ in the 4-position.

In the preferred embodiment wherein N together with $R^1$ and $R^2$ form a piperidine with at least one substituent $R^{4'}$ in the 4-position, $N(R^1)R^2$ may be defined as

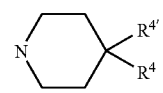

wherein $R^4$ is selected from the group consisting of hydrogen, hydroxy, halogen, $C_{1-8}$-alkyl, $C_{3-8}$-cycloalkyl, $C_{1-8}$-alkoxy, $C_{1-8}$-alkylcarbonyl, $C_{1-8}$-alkylidene, $C_{2-8}$-alkenyl, and $C_{2-8}$-alkynyl each of which may be optionally substituted with a substituent $R^5$ and wherein $R^{4'}$ is selected from the group consisting of $C_{1-8}$-alkyl, $C_{3-8}$-cycloalkyl, $C_{1-8}$-alkylidene, $C_{2-8}$-alkenyl, and $C_{2-8}$-alkynyl each of which may be optionally substituted with a substituent $R^5$; and $R^5$ is selected from the group consisting of hydrogen, halogen, hydroxy, $C_{1-8}$-alkyl, $C_{3-8}$-cycloalkyl, $C_{1-8}$-alkylidene, $C_{2-8}$-alkenyl and $C_{2-8}$-alkynyl.

In a preferred embodiment, $R^4$ is selected from the group consisting of hydrogen, hydroxy and halogen most preferably hydrogen and hydroxy and $R^5$ substituted $C_{1-8}$-alkyl.

The one or more substituent $R^{4'}$ may be selected from the group consisting of $C_{1-8}$-alkyl, $C_{3-8}$-cycloalkyl, $C_{1-8}$-alkylidene, each of which may be optionally substituted with a substituent $R^5$. In a combination of preferred embodiments, the one or more substituent $R^4$ may be selected from the group consisting of a $C_{1-8}$-alkyl, and $C_{3-8}$-alkylidene, each of which may be optionally substituted with a substituent $R^5$ wherein $R^5$ is selected from the group consisting of hydrogen, halogen, hydroxy, $C_{1-8}$-alkyl and $C_{3-8}$-cycloalkyl.

Most preferably, $R^5$ is selected from the group consisting of hydrogen, halogen, hydroxy, $C_{1-8}$-alkyl, $C_{3-8}$-cycloalkyl, $C_{3-8}$-heterocyclyl, $C_{1-8}$-alkylcarbonyl, $C_{1-8}$-alkylidene, $C_{2-8}$-alkenyl and $C_{2-8}$-alkynyl, particularly hydrogen, hydroxy, halogen and $C_{1-8}$-alkyl.

In a particularly preferred embodiment, $R^4$ is selected from the group consisting of propyl, propylidene, butyl, butylidene, pentyl and pentylidene, each of which may be optionally substituted. In a most preferred embodiment, $R^4$ is selected from the group consisting of butyl, a pentyl and 3-($C_{1-8}$-alkyl)-butylidene, each of which may be optionally substituted.

As will be clear to the person skilled in the art, embodiments of compound I may be chiral or comprised of one or more chiral centres. Where the compounds according to the invention have at least one chiral center, they may exist as a racemate, enantiomers or diastermeomers. It should be noted that all such isomers and mixtures thereof are included in the scope of the present invention. Furthermore, some of the crystalline forms for compounds of the present invention may exist as polymorphs and as such are intended to be included in the present invention. In addition, some of the compounds of the present invention may form solvates with water (i.e. hydrates) or common organic solvents. Such solvates are also included in the scope of this invention.

Where the processes for the preparation of the compounds according to the invention give rise to mixtures of stereoisomers, such isomers may be separated by conventional techniques such as preparative chiral chromatography. The compounds may be prepared in racemic form, or individual enantiomers may be prepared either by stereoselective synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary.

During any of the processes for preparation of the compounds of the present invention, it may be necessary or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

The term $R^X$ relates to a substituent of the term X and may be absent or selected from the group consisting of hydrogen, $C_{1-8}$-alkyl, $C_{3-8}$-cycloalkyl, $CH_2—N(R^5)(R^5)$, $CH_2—OR^5$, $CH_2—SR^5$, $CH_2—O—C(=O)R^5$, $CH_2—O—C(=S)R^5$; wherein $R^5$ is selected from the group consisting of hydrogen, halogen, optionally substituted aryl, optionally substituted heteroaryl, optionally substituted $C_{3-8}$-cycloalkyl, optionally substituted $C_{3-8}$-heterocyclyl, optionally substituted $C_{1-8}$-alkyl, optionally substituted $C_{1-8}$-alkylidene, optionally substituted $C_{2-8}$-alkenyl, optionally substituted $C_{2-8}$-alkynyl and optionally substituted $C_{1-8}$-alkylcarbonyl.

In a preferred embodiment, $R^X$ is selected from the group consisting of hydrogen, $C_{1-8}$-alkyl, $CH_2—N(R^5)(R^5)$, $CH_2—OR^5$, and $CH_2—O—C(=O)R^5$. The nature of $R^X$ depends on X. It is intended to serve so as to make a prodrug of the molecule, to increase its bioavailability, or to lower the reactivity of the term X, such as in a protective group. In a suitable embodiment, $R^X$ is a $C_{1-8}$-alkyl such as methyl, ethyl, propyl, butyl, pentyl, or hexyl, typically methyl, ethyl or propyl.

As can be derived from the Examples and from the disclosure herein, the compounds according to Formula I are intended for use as a pharmaceutical. Thus, a further aspect of the invention relates to a pharmaceutical composition comprising a compound as described herein, together with pharmaceutically acceptable carriers or excipients. Excipients and carriers will depend on, amongst other factors, the route of administration of the compound.

Compounds of the present invention may be administered in any of the foregoing compositions and according to dosage regimens established in the art whenever specific pharmacological modification of the activity of muscarinic receptors is required.

The present invention also provides pharmaceutical compositions comprising one or more compounds of Formula I together with a pharmaceutically acceptable diluent or excipient. Preferably such compositions are in unit dosage forms such as tablets, pills, capsules (including sustained-release or delayed-release formulations), powders, granules, elixirs, tinctures, syrups and emulsions, sterile parenteral solutions or suspensions, aerosol or liquid sprays, drops, ampoules, auto-injector devices or suppositories; for oral, parenteral (e.g., intravenous, intramuscular or subcutaneous), intranasal, sublingual or rectal administration, or for administration by inhalation or insufflation, and may be formulated in an appropriate manner and in accordance with accepted practices such as those disclosed in Remington's Pharmaceutical Sciences, Gennaro, Ed., Mack Publishing Co., Easton Pa., 1990. Alternatively, the compositions may be in sustained-release form suitable for once-weekly or once-monthly administration; for example, an insoluble salt of the active compound, such as the decanoate salt, may be adapted to provide a depot preparation for intramuscular injection. The present invention also contemplates providing suitable topical formulations for administration to, e.g., eye or skin or mucosa.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents, flavoring agents and coloring agents can also be incorporated into the mixture. Suitable binders include, without limitation, starch, gelatin, natural sugars such as glucose or beta-lactose, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For preparing solid compositions such as tablets, the active ingredient is mixed with a suitable pharmaceutical excipient, e.g., such as the ones described above, and other pharmaceutical diluents, e.g., water, to form a solid preformulation composition containing a homogeneous mixture of a compound of the present invention, or a pharmaceutically acceptable salt thereof. By the term "homogeneous" is meant that the active ingredient is dispersed evenly throughout the composition so that the composition may be readily subdivided into equally effective unit dosage forms such as tablets, pills and capsules. The solid preformulation composition may then be subdivided into unit dosage forms of the type described above containing from 0.1 to about 50 mg of the active ingredient of the present invention. The tablets or pills of the present composition may be coated or otherwise compounded to provide a dosage form affording the advantage of prolonged action. For example, the tablet or pill can comprise an inner core containing the active compound and an outer layer as a coating surrounding the core. The outer coating may be an enteric layer, which serves to resist disintegration in the stomach and permits the inner core to pass intact into the duodenum or to be delayed in release. A variety of materials can be used for such enteric layers or coatings, such materials including a number of polymeric acids and mixtures of polymeric acids with conventional materials such as shellac, cetyl alcohol and cellulose acetate.

The liquid forms in which the present compositions may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical carriers. Suitable dispersing or suspending agents for aqueous suspensions include synthetic and natural gums such as tragacanth, acacia, alginate, dextran, sodium carboxymethylcellulose, gelatin, methylcellulose or polyvinyl-pyrrolidone. Other dispersing agents, which may be employed, include glycerin and the like. For parenteral administration, sterile suspensions and solutions are desired. Isotonic preparations, which generally contain suitable preservatives, are employed when intravenous administration is desired. The compositions can also be formulated as an ophthalmic solution or suspension formation, i.e., eye drops, for ocular administration.

Advantageously, compounds of the present invention may be administered in a single daily dose, or the total daily dosage may be administered in divided doses two, three or four times daily. Furthermore, compounds for the present invention may be administered in intranasal form via topical use of suitable intranasal vehicles, or via transdermal routes, using those forms of transdermal skin patches well known to persons skilled in the art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound employed. A physician or veterinarian of ordinary skill can readily determine and prescribe the effective amount of the drug required to prevent, counter or arrest the progress of the disease or disorder, which is being treated.

The daily dosage of the products may be varied over a wide range from 0.01 to 100 mg per adult human per day. For oral administration, the compositions are preferably provided in the form of tablets containing 0.01, 0.05, 0.1, 0.5, 1.0, 2.5, 5.0, 10.0, 15.0, 25.0 or 50.0 mg of the active ingredient for the symptomatic adjustment of the dosage to the patient to be treated. A unit dose typically contains from about 0.001 mg to about 50 mg of the active ingredient, preferably from about 1 mg to about 10 mg of active ingredient. An effective amount of the drug is ordinarily supplied at a dosage level of from about 0.0001 mg/kg to about 25 mg/kg of body weight per day. Preferably, the range is from about 0.001 to 10 mg/kg of body weight per day, and especially from about 0.001 mg/kg to 1 mg/kg of body weight per day. The compounds may be administered on a regimen of 1 to 4 times per day.

Compounds according to the present invention may be used alone at appropriate dosages defined by routine testing in order to obtain optimal pharmacological effect on a muscarinic receptor, in particular the muscarinic $M_1$ or $M_4$ receptor subtype, while minimizing any potential toxic or otherwise unwanted effects. In addition, co-administration or sequential administration of other agents, which improve the effect of the compound, may, in some cases, be desirable.

The pharmacological properties and the selectivity of the compounds of this invention for specific muscarinic receptor subtypes may be demonstrated by a number of different assay methods using recombinant receptor subtypes, preferably of the human receptors if these are available, e.g., conventional second messenger or binding assays. A particularly convenient functional assay system is the receptor selection and amplification assay disclosed in U.S. Pat. No. 5,707,798 describing a method of screening for bioactive compounds by utilizing the ability of cells transfected with receptor DNA, e.g., coding for the different muscarinic subtypes, to amplify in the presence of a ligand of the receptor. Cell amplification is detected as increased levels of a marker also expressed by the cells.

An important aspect of the present invention relates to a method of increasing an activity of a cholinergic receptor comprising contacting the cholinergic receptor or a system containing the cholinergic receptor with an effective amount of at least one compound of Formula I, as defined supra. The present investigators have surprisingly found that the compounds of Formula I act as cholinergic agonists and, most remarkably, the compounds of Formula I are selective for the either the $M_1$ or $M_4$, or both the $M_1$ and $M_4$ muscarinic receptor subtypes.

Furthermore, beyond the remarkable selectivity of the compounds of the present invention for the $M_1$ and $M_4$ muscarinic receptor subtypes, the present investigators have surprisingly found that compounds of Formula I further act as dopaminergic $D_2$ antagonists or $D_2$ inverse agonists.

As was discussed earlier, this combined activity ($M_1$ and $M_4$ agonism, dopaminergic $D_2$ antagonism) is an attractive method of treating an array of mental disorders. Consequently, a further important aspect of the present invention relates to a method of treating or preventing a mental disorder in a mammal, such as a human, comprising the administration of an effective amount of a compound of Formula I.

Disorders considered to be suitable for treatment by either $M_1$ and/or $M_4$ agonism, or combined $M_1/M_4$ agonism and dopaminergic $D_2$ antagonism are selected from the group consisting of cognitive impairment, forgetfulness, confusion, memory loss, attentional deficits, deficits in visual perception, depression, pain, sleep disorders, psychosis, and increased intraocular pressure.

Further, suitable disorders considered to be suitable and particularly attractive may be selected from the group consisting of neurodegenerative diseases, Alzheimer's disease, Parkinson's disease, schizophrenia, Huntington's chorea, Friederich's ataxia, Gilles de la Tourette's Syndrome, Down Syndrome, Pick disease, dementia, clinical depression, age-related cognitive decline, attention-deficit disorder, sudden infant death syndrome, and glaucoma.

Furthermore the compounds of this invention are useful in the treatment of mania, bipolar disorder, unipolar disorder, schizoaffective disorder, schizophreniform disorder and anxiety. It should be noted that other non-schizophrenic causes of psychosis, including drug induced, those associated with dementia and other neurodegenerative disorders (such as Huntington's) are also anticipated to be suitable.

The Tic disorders also include a spectrum of disorders including Tourettes and OCD.

The affective disorder spectrum, including unipolar, bipolar are also anticipated to be suitable for treatment using compounds of Formula I.

An important aspect of the invention therefore relates to the use of a compound according or a pharmaceutically acceptable salt thereof, or a pharmaceutical composition containing either entity, for the preparation of a medicament for the prophylactic or curative treatment of psychosis or alleviation of symptoms associated with psychosis.

The medicament acts, at least in part, as an $M_1$ agonist or as $M_1$ and $M_4$ agonist. The compound according to Formula I may further act as a $D_2$ antagonist. Thus, an important aspect of the invention relates to a use of compounds of Formula I as $M_1$ and $M_4$ agonist, as well as $D_2$ antagonists. Illustrative examples of compounds with this combined activity are tabulated in Example 1.

Compounds 61KS19, 45NK70, 45NK71, 45NK110, 61KS12 and 61KS13 have high binding efficacy for the $M_1$ and $M_4$ receptor subtypes. Moreover, compounds of Formula I have high selectivity for the $M_1$ and $M_4$ receptor subtypes over $M_2$, $M_3$, $M_5$ receptor subtypes. Further, compounds of Formula I have $D_2$ antagonistic activity.

As discussed in Felder et al (*J. Med. Chem.* 2000), muscarinic receptors may be implicated in the control of amyloid precursor processing, in particular by activation of the $M_1$ receptor. Thus, a further aspect of the present invention relates to a method of modulating or preventing the progression or formation of amyloid plaques in an individual susceptible to or affected by Alzheimer's Disease by administering an effective amount of a compound of Formula I, said effective amount sufficient to modulate amyloid precursor protein processing.

EXAMPLES

Embodiments of the present invention is disclosed in further detail in the following examples, which are not in any way intended to limit the scope of the invention as claimed.

Example 1

Screening Assay

In the present example, methods for R-SAT and radioligand binding are described. In addition, screening of test compounds in assays using muscarinic receptor subtypes $M_1$ and $M_4$ and dopamine receptor subtype $D_2$ are described.

Methods

The $M_1$ and $M_4$ muscarinic receptor subtypes were cloned substantially as described by Bonner et al., (1987) *Science* 273 p. 527 and Bonner et al, (1988) *Neuron* 1, p. 403. R-SAT assays were carried out substantially as described in U.S. Pat. No. 5,707,798 and by Braüner-Osborne, H. B. and Brann, M. R. (1995), *Eur. J. Pharmacol.* 295:93-102. NIH-3T3 cells (available from the American Type Culture Collection as ATCC CRL 1658) were transfected with plasmid DNA encoding the m1 and m4 receptors and plasmid DNA encoding β-galactosidase. Transfected cells were grown in the presence of between 1 nM and 40 µM of the test compound for 5 days. On day 5, the cells were lysed using 0.5% nonidet-P and β-galactosidase expression was quantified using the chromogenic substrate o-nitrophenyl-β-D-galactoside (ONGP).

Data were normalized relative to the maximum response of the cells to the muscarinic agonist carbachol, and the following equation was fitted to the data:

response=minimum+(maximum−minimum)/(1+ ([ligand]/$EC_{50}$))

% Efficacy was defined as (maximum−minimum)/(maximum response of cells to carbachol). $pEC_{50}$=−log ($EC_{50}$). Where data gave a bell-shaped curve, "maximum" was defined as the highest observed response.

The $D_2$ dopamine receptor subtype was cloned substantially as described by Stormann, Gdula, Weiner and Brann, 1990 [*Mol Pharmacol* 37, 1-6]. Cell membranes expressing the $D_2$ receptor were prepared by transfecting tSA cells (Chahine, M., Bennet, P. B., George, A. L., Horn, R. (1994) *Pfluegers Arch.* 427, 136-142) with 10 µg plasmid DNA encoding the human dopamine $D_2$ receptor and 40 µl Superfect (Qiagen). The cells were harvested 48 hours and transfection and membranes were prepared by homogenizing the cells using a Polytron harvester in 20 mM Hepes, 10 mM EDTA, pH 7.4. The homogenate was centrifuged for 30 minutes at 37,000 g. The pellet was homogenized again in 60 ml 20 mM Hepes, 5 mM EDTA. The homogenate was centrifuged for 30 minutes at 37,000 g. The supernatant was discarded. The pellet was homogenized again in 10 ml 20 mM Hepes, 1 mM EDTA. The resultant membranes were frozen at −80° C.

The membranes were combined with 150 pM [$^3$H]-Spiperone (Amersham-Pharmacia, 107 Ci/mmol) and ligand concentrations between 1 nM and 10 µM, or haloperidol concentrations between 0.1 nM and 1 µM in 460 µl 20 mM Hepes, 1 mM EDTA, 0.1% (w/v) bovine serum albumin. Nonspecific binding was defined as binding in the presence of 1 µM haloperidol. The membranes were incubated for 4 hours at 37° C., and then filtered onto Packard GFB Filterplates using a Packard harvester. The membranes were dried and 50 µl Microscint (Packard) was added to each well. The amount of bound radioligand was quantified using a Packard Topcount scintillation counter.

Data were normalized relative to the maximum inhibition of [$^3$H]-Spiperone binding by 1 µM haloperidol, and the following equation was fitted to the data:

% inhibition=minimum+(maximum−minimum)/(1+ ([ligand]/[$IC_{50}$]))

% inhibition was defined as (maximum−minimum)/(maximum response of cells to haloperidol). $pIC_{50}$=−log ($IC_{50}$). NT=not tested.

Results

| | R-SAT | | | | $D_2$ |
|---|---|---|---|---|---|
| | $M_1$ | | $M_4$ | | |
| Compound | % Efficacy | $pEC_{50}$ | % Efficacy | $pEC_{50}$ | [$^3$H]Spiperone $pIC_{50}$ |
| 61KS-19 | 115 | 7.6 | 141 | 7.5 | 6.1 |
| 61KS-12 | 107 | 7.5 | 164 | 7.1 | 6.0 |
| 45NK-71 | 71 | 7.0 | 49 | 6.6 | 6.4 |
| 61KS-13 | 106 | 7.4 | 100 | 7.4 | 6.4 |
| 45NK-70 | 70 | 7.3 | 40 | 7.1 | 6.2 |
| 45NK-110 | 89 | 7.0 | 61 | 5.9 | 5.5 |
| 62KK040d | 83 | 7.6 | 93 | 6.4 | 7.1 |
| 61KK69 | 94 | 7.2 | 78 | 6.3 | 6.7 |
| 61KS70-1 | 96 | 7.1 | 112 | 6.1 | 6.5 |
| 61KS91 | 106 | 7.9 | 88 | 7.6 | 6.7 |
| 85LM14 | 104 | 7.5 | 94 | 5.8 | 7.1 |
| 85LM49B | 98 | 7.6 | NT | NT | 6.3 |

-continued

| | R-SAT | | | |
|---|---|---|---|---|
| | $M_1$ | | $M_4$ | | $D_2$ |
| Compound | % Efficacy | $pEC_{50}$ | % Efficacy | $pEC_{50}$ | [³H]Spiperone $pIC_{50}$ |
| 85LM91-78R | 99 | 7.5 | 141 | 6.1 | 7.3 |
| 86KK25-a | 73 | 7.0 | 36 | 2 | 6.2 |
| 86KKM25-d | 84 | 7.0 | 63 | 6.1 | 6.3 |
| 86KK22-K | 75 | 6.7 | 56 | 5.9 | 6.2 |
| 97KK28 | 71 | 6.7 | NT | NT | 6.6 |
| 85LM12 | 78 | 6.9 | NT | NT | 6.4 |
| 97KS96-2 | 63 | 7.3 | 50 | 2 | 7.0 |
| 79KS97 | 70 | 8.2 | NT | NT | 7.0 |

Example 2

Behavioral Studies

Methods

Animals

Male Non-Swiss Albino mice (Harlan Sprague-Dawley) were housed (4 mice/cage) in rooms with temperature and humidity controlled and water and food (Harlan Teklad) freely available. Mice were kept on a 12-hr light:dark cycle.

Procedure

Locomotor Activity

Plastic 20×20×30 cm activity cages were equipped with photocell beams (AccuScan Instruments). For spontaneous activity, 61KS19 (1, 3 and 10 mg/kg) was administered alone i.p. 30 min before the session. For hyperactivity experiments, mice were treated with 0.3 mg/kg dizocilpine, 3.0 mg/kg d-amphetamine or 3.0 mg/kg scopolamine i.p. 15 min before the session (15 min after 61KS19). Locomotor data were collected during a 15 min session without habituation in a lit room. Each dose combination was tested in a separate group of animals (n=8). Distance traveled (cm) was calculated and averaged followed by ANOVA and post-hoc Dunnett's t-test comparisons.

Catalepsy

A custom-built 8-mm rod that is raised 3.5 cm from the lab benchtop was used. 61KS19 (10 mg/kg) or haloperidol (1 mg/kg) were administered i.p. 60 min before the start of the session. The forepaws of each animal is placed on the rod and the time to step down is measured. If the animal steps off immediately, another attempt is made until the animal stays on for more than 10 sec or 10 attempts have been made. A maximum of 2 min is allowed at which time the animal is taken away from the rod and returned to the homecage. Each dose or dose combination was tested in a separate group of animals (n=6). Averages and standard errors were calculated and compared using an ANOVA and post-hoc Dunnett's t-tests.

Example 3

Synthetic Procedures 3.1 General Preparative LC-MS Procedure

Preparative purification was performed on a Waters auto purification system (600 pumps, 2700 sample manager, 996 PDA detector, ZMD massspectrometer).

The columns used were YMC C18 J'sphere ODS H80. Buffer A was 0.15% TFA in water, buffer B was 0.15% TFA in acetonitrile/water 95/5. The columns were operated at 17 ml/min. Following an initial hold of 2.5 min at 30% buffer B, compounds were separated using a gradient af 30-100% buffer B in 8.5 min. A dual column setup with two pumps was used to equilibrate one column, while running on the other.

3.2 3-Trifluorosulfonyl-8-tertButyloxycarbonyl-8-azabicyclo[3.2.1]-oct-2-ene (N-Boc-nortropanone enol triflate) (104KS22)

LDA was generated by adding BuLi (20 mL, 1.68M, 32.6 mmol) to a solution of diisopropylamine (2.38 g, 32.6 mmol) in dry THF (10 mL) at −78° C. under argon. The mixture was kept at that temperature for 30 min followed by the addition of a solution of N-Bocnortropinone (5.27 g, 23.4 mmol) in dry THF (20 mL). The mixture was then left stirring for 1 h while maintaining the temperature at 78° C. Then a solution of 2-[N,N -Bis(trifluoromethylsulfonyl) amino]-5-chloropyridine (10.08 g, 25.7 mmol) in dry THF (20 mL) and the mixture was slowly allowed to reach room temperature overnight and subsequently concentrated and exposed to column chromatography (SiO$_2$; EtOAc/heptane 1:6, R$_f$(product)=0.31) to give the title compound (104KS22) (6.68 g, 80%) which on prolonged standing crystallised into a white solid. $^1$H NMR (CDCl$_3$) δ 1.43 (s, 9H, Boc-C$\underline{H}_3$), 1.72 (m, 1H), 1.93-2.03 (m, 2H), 2.07 (d, J=16.6 Hz, 1H), 2.23 (broad m, 1H), 3.05 (broad s, 1H), 4.42 (broad m, 2H, H1+H5), 6.10 (broad s, 1H, H2). $^{13}$C NMR (CDCl$_3$) δ 28.4 (Boc C$\underline{H}_3$), 30.1 and 29.2 (rotameric), 34.7 and 34.9 (rotameric), 36.5 and 37.1 (rotameric), 51.9, (broad s), 80.5 ((CH$_3$)$_3$$\underline{C}$—), 118.7 (—$\underline{C}$F$_3$, q, J=300 Hz), 124.0 (broad s, C2), 148.0 (broad s, C3), 153.9 (Boc C=O).

3.3 General Procedure 1 (GP1)

To a mixture of 3-Trifluorosulfonyl-8-tertButyloxycarbonyl-8-azabicyclo[3.2.1]-oct-2-ene (104KS22) (0.107 g, 0.3 mmol, 1.0 equiv), CuI (0.011 g, 0.05 moles, 0.20 equiv), dimethylethylamine (0.219 g, 3.0 mmol, 10 equiv) and the alkyne (2.0 equiv) in dry THF (3 mL) was added (PPh$_3$)$_4$Pd (0.10 equiv) at room temperature under argon. The mixture was shaken for 2 h followed by filtration and concentration. The residual syrup was taken up in DCM (2 mL) followed by careful addition of TFA (0.5 mL). The mixture was shaken for 10 min before it was concentrated, basified with NaOH (2M, 3 mL), extracted (EtOAc), concentrated and put on an ionexchange column (Varian BondElut®-SCX, H$^+$). Elution with 2.5% NH$_4$OH in MeOH and concentration gave the desired product.

3.4 3-Pent-1-ynyl-8-azabicyclo[3.2.1]oct-2-ene (79KS36-5)

3-Trifluorosulfonyl-8-tertButyloxycarbonyl-8-azabicyclo [3.2.1]-oct-2-ene (104KS22) (0.107 g, 0.3 mmol) and Pent-1-yne (0.041 g, 0.6 mmol) were reacted according to GP1 to give the title compound (79KS36-5) (0.033 g, 62%). HPLC-MS (ammonium acetate): [M+H]$^+$=176.23

3.5 3-Hex-1-ynyl-8-azabicyclo[3.2.1]oct-2-ene (79KS36-6)

3-Trifluorosulfonyl-8-tertButyloxycarbonyl-8-azabicyclo [3.2.1]-oct-2-ene (104KS22) (0.107 g, 0.3 mmol) and Hex-1-yne (0.049 g, 0.6 mmol) were reacted according to GP1 to give the title compound (79KS36-6) (0.049 g, 86%). HPLC-MS (ammonium acetate): [M+H]$^+$=190.26

3.6 3-Hept-1-ynyl-8-azabicyclo[3.2.1]oct-2-ene (79KS36-7)

3-Trifluorosulfonyl-8-tertButyloxycarbonyl-8-azabicyclo [3.2.1]-oct-2-ene (104KS22) (0.107 g, 0.3 mmol) and Hept- 1-yne (0.058 g, 0.6 mmol) were reacted according to GP1 to give the title compound (79KS36-7) (0.051 g, 84%). HPLC-MS (ammonium acetate): [M+H]$^+$=204.28

3.7 4-(8-Azabicyclo[3.2.1]oct-2-en-3-yl)-but-3-yn-1-ol (79KS36-2)

3-Trifluorosulfonyl-8-tertButyloxycarbonyl-8-azabicyclo[3.2.1]-oct-2-ene (104KS22) (0.107 g, 0.3 mmol) and But-3-yn-1-ol (0.042 g, 0.6 mmol) were reacted according to GP1 to give the title compound (79KS36-2) (0.018 g, 34%). HPLC-MS (ammonium acetate): [M+H]$^+$=178.21

3.8 5-(8-Azabicyclo[3.2.1]oct-2-en-3-yl)-pent-4-yn-1-ol (79KS36-3)

3-Trifluorosulfonyl-8-tertButyloxycarbonyl-8-azabicyclo[3.2.1]-oct-2-ene (104KS22) (0.107 g, 0.3 mmol) and Pent-3-yn-1-ol (0.050 g, 0.6 mmol) were reacted according to GP1 to give the title compound (79KS36-3) (0.045 g, 79%). HPLC-MS (ammonium acetate): [M+H]$^+$=192.23

3.9 General Method 2 (GP2)

To a slurry of CuI (2.0 equiv) in dry THF (5 mL) was added R-M (R=alkyl, M=Li or MgX) (4.0 equiv) at −25° C. and stirred at that temperature for 30 min before adding a solution of 3-Trifluorosulfonyl-8-tertButyloxycarbonyl-8-azabicyclo[3.2.1]-oct-2-ene (104KS22) (1.0 equiv) in dry THF (5 mL). The reaction mixture was kept stirring at −25° C. for 2 h before the cooling was removed. The reaction was then quenched by firstly addition of water (20 mL) and secondly addition of a saturated aqeuous solution of NH$_4$Cl (20 mL) before extraction with DCM. The combined organic phase was washed with a saturated aqeuous solution of NH$_4$Cl, dried (Na$_2$SO$_4$), filtered and concentrated in vacuo to give the crude product. This was then purified by column chromatography (SiO$_2$; EtOAc/heptane 1:10 which gave the desired products

3.10 8-tertButyloxycarbonyl-3-propyl-8-aza-bicyclo[3.2.1]oct-2-ene (79KS74)

CuI (0.234 g, 1.23 mmol), PrMgBr (1.3 mL, 2.0M, 2.46 mmol) 3-Trifluorosulfonyl-8-tertButyloxycarbonyl-8-azabicyclo[3.2.1]-oct-2-ene (104KS22) (0.220 g, 0.616 mmol) were reacted according to GP2 to give the title compound (79KS74) (0.083 g, 54%). $^1$H NMR (CDCl$_3$) δ 0.84 (t, 3H, J=7.1 Hz, —CH$_2$CH$_2$CH$_3$), 1.36 (sixt, 2H, J=7.1 Hz, —CH$_2$CH$_2$CH$_3$), 1.43 (s, 9H, Boc-CH$_3$), 1.56 (dt, 1H, J=7.0 Hz, 13.2 Hz), 1.64 (d, 1H, J=17.0 Hz), 1.76-1.96 (m, 4H), 2.11 (m, 1H), 2.67 (d, 1H, J=17.0 Hz), 4.18-4.34 (m, 2H), 5.68 (d, 1H, J=4.8 Hz, H2); $^3$C NMR (CDCl$_3$) δ 13.7 (—CH$_2$CH$_2$CH$_3$), 20.7 (—CH$_2$CH$_2$CH$_3$), 28.6 (Boc-CH$_3$), 30.0, 34.9, 37.4, 38.5 (—CH$_2$CH$_2$CH$_3$), 52.3, 53.3, 79.2 (—C(CH$_3$)$_3$), 126.6, 135.4 (C2, C3), 154.4 (C=O).

3.11 8-tertButyloxycarbonyl-3-butyl-8-aza-bicyclo[3.2.1]oct-2-ene (79KS61)

CuI (0.289 g, 1.52 mmol), BuLi (1.9 mL, 1.6 M, 3.03 mmol) 3-Trifluorosulfonyl-8-tertButyloxycarbonyl-8-azabicyclo[3.2.1]-oct-2-ene (104KS22) (0.271 g, 0.758 mmol) were reacted according to GP2 to give the title compound (79KS61) (0.104 g, 52%). $^1$H NMR (CDCl$_3$) δ 0.82 (t, 3H, J=7.2 Hz, —CH$_2$CH$_2$CH$_2$CH$_3$), 1.14-1.34 (m, 4H), 1.40 (s, 9H, Boc-CH$_3$), 1.53 (dt, 1H, J=7.6 Hz, 13.3 Hz), 1.61 (d, 1H, J=17.1 Hz), 1.72-1.92 (m, 4H), 2.07 (m, 1H), 2.64 (d, 1H, J=17.1 Hz), 4.14 (m, 2H), 5.64 (d, 1H, J=4.6H, H2); $^{13}$C NMR (CDCl$_3$) δ 14.1 (—CH$_2$CH$_2$CH$_2$CH$_3$), 22.3 (—CH$_2$CH$_2$CH$_2$CH$_3$), 28.6 (Boc-CH$_3$), 29.7 (—CH$_2$CH$_2$CH$_2$CH$_3$), 30.0, 34.8, 36.1 (—CH$_2$CH$_2$CH$_2$CH$_3$), 37.5, 52.3, 53,3 79.1 (—C(CH$_3$)$_3$), 126.4, 135.6 (C2, C3), 154.4 (C=O).

3.12 8-tertButyloxycarbonyl-3-pentyl-8-aza-bicyclo[3.2.1]oct-2-ene (79KS94)

CuI (0.712 g, 3.74 mmol), pentyl-MgBr (3.8 mL, 2.0 M, 7.48 mmol) 3-Trifluorosulfonyl-8-tertButyloxycarbonyl-8-azabicyclo[3.2.1]-oct-2-ene (104KS22) (0.669 g, 1.87 mmol) were reacted according to GP2 to give the title compound (79KS94) (0.238 g, 46%). $^1$H NMR (CDCl$_3$) δ 0.87 (t, 3H, J=7.2 Hz, —CH$_2$CH$_2$CH$_2$CH$_2$CH$_3$), 1.15-1.38 (m, 6H), 1.44 (s, 9H, Boc-CH$_3$), 1.57 (dt, 1H, J=8.0 Hz, J=12.0 Hz), 1.65 (d, 1H, J=17.1 Hz), 1.76-1.96 (m, 4H), 2.06-2.17 (m, 1H), 2.68 (d, 1H, J=17.1 Hz), 4.22-4.32 (m, 2H), 5.68 (d, 1H, J=5.0 Hz, H2); $^{13}$C NMR (CDCl$_3$) δ 14.2 (—CH$_2$CH$_2$CH$_2$CH$_2$CH$_3$), 22.7 (—CH$_2$CH$_2$CH$_2$CH$_2$CH$_3$), 27.2 (—CH$_2$CH$_2$CH$_2$CH$_2$CH$_3$), 28.6 (Boc-CH$_3$), 22.7 (—CH$_2$CH$_2$CH$_2$CH$_2$CH$_3$), 34.9, 36.4 (—CH$_2$CH$_2$CH$_2$CH$_2$CH$_3$), 37.5, 52.3, 53.3, 79.2 (—C(CH$_3$)$_3$), 126.4, 135.7 (C2, C3), 154.4 (C=O).

3.13 8-tertButyloxycarbonyl-3-hexyl-8-aza-bicyclo[3.2.1]oct-2-ene (79KS79)

CuI (0.234 g, 1.23 mmol), hexyl-MgBr (1.23 mL, 2.0 M, 7.48 mmol) 3-Trifluorosulfonyl-8-tertButyloxycarbonyl-8-azabicyclo[3.2.1]-oct-2-ene (104KS22) (0.220 g, 0.616 mmol) were reacted according to GP2 to give the title compound (79KS79) (0.073 g, 40%). $^1$H NMR (CDCl$_3$) δ 0.85 (t, 3H, J=6.7 Hz, —CH$_2$CH$_2$CH$_2$CH$_2$CH$_2$CH$_3$), 1.14-1.38 (m, 8H), 1.42 (s, 9H, Boc-CH$_3$), 1.50-1.60 (m, 1H), 1.63 (d, 1H, J=16.8 Hz), 1.74-1.94 (m, 4H), 2.03-2.17 (m, 1H), 2.65 (br s, 1H), 4.25 (br s, 2H), 5.65 (br s, 1H, H2), $^{13}$C NMR (CDCl$_3$) δ 14.2 (—CH$_2$CH$_2$CH$_2$CH$_2$CH$_2$CH$_3$), 22.8 (—CH$_2$CH$_2$CH$_2$CH$_2$CH$_3$), 27.5 (—CH$_2$CH$_2$CH$_2$CH$_2$CH$_2$CH$_3$), 28.6 (Boc-CH$_3$), 28.9 (—CH$_2$CH$_2$CH$_2$CH$_2$CH$_3$), 30.1, 31.9 (—CH$_2$CH$_2$CH$_2$CH$_2$CH$_2$CH$_3$), 34.8, 36.4 (—CH$_2$CH$_2$CH$_2$CH$_2$CH$_2$CH$_3$), 37.6, 52.3, 53.2, 79.2 (—C(CH$_3$)$_3$), 126.3, 135.9 (C2, C3), 154.4 (C=O).

3.14 General Procedure 3 (GP3)

The alkene (1.0 equiv) was dissolved in MeOH (3 mL) and Pd(10%)/C (tip of a spatula) was added. H$_2$ (1 atm., balloon) was applied under stirring. The reaction mixture was left stirring for 2.5 h before it was filtered through a pad of celite and concentrated in vacuo to give the desired products which was pure enough for further reaction.

3.15 8-tertButyloxycarbonyl-3-propyl-8-aza-bicyclo[3.2.1]octane (79KS75)

8-tertButyloxycarbonyl-3-propyl-8-aza-bicyclo[3.2.1]oct-2-ene (79KS74) (0.039 g, 0.155 mmol) was reacted according to GP3 to give the title compound (79KS75) (0.030 g, 76%). $^1$H NMR (CDCl$_3$) δ 0.86 (t, 3H, J=7.5 Hz, —CH$_2$CH$_2$CH$_3$), 1.08-1.17 (m 2H), 1.20-1.36 (m, 4H), 1.44 (s, 9H, Boc-CH$_3$), 1.52 (m, 2H, J=13.8 Hz), 1.56-1.64 (m, 2H), 1.70-1.82 (m, 1H), 1.86-1.94 (m, 2H), 4.05 (br s, 2H, H2); $^{13}$C NMR (CDCl$_3$) δ 14.4 (—CH$_2$CH$_2$CH$_3$), 20.0 (—CH$_2$CH$_2$CH$_3$), 28.2, 28.4, 28.7 (Boc-CH$_3$), 38.0, 39.5, 53,8, 79.0 (—C(CH$_3$)$_3$), 153.7 (C=O).

3.16 8-tertButyloxycarbonyl-3-butyl-8-aza-bicyclo[3.2.1]octane (79KS92)

8-tertButyloxycarbonyl-3-butyl-8-aza-bicyclo[3.2.1]oct-2-ene (79KS61) (0.047 g, 0.177 mmol) was reacted according to GP3 to give the title compound (79KS92) (0.045 g, 95%). $^1$H NMR (CDCl$_3$) δ 0.86 (t, 3H, J=6.6 Hz, —CH$_2$CH$_2$CH$_2$CH$_3$), 1.10-1.40 )m, 8H), 1.45 (s, 9H, Boc-CH$_3$), 1.47-1.56 (m, 2H, J=13.2), 1.56-1.64 (m, 2H), 1.68-1.82 (m, 1H), 1.85-1.98 (m, 2H), 4.18 (m, 2H); $^{13}$C NMR (CDCl$_3$) δ 14.5 (—CH$_2$CH$_2$CH$_2$CH$_3$), 23.3 (—CH$_2$CH$_2$CH$_2$CH$_3$), 28.4, 28.7 (Boc-CH$_3$), 29.0, 29.4 (—CH$_2$ CH$_2$CH$_2$CH$_3$), 37.1 (—CH$_2$CH$_2$CH$_2$CH$_3$), 37.9, 38.7, 53.6, 54.4, 79.2 (—C(CH$_3$)$_3$), 153.9 (C=O).

3.17 3-Pentyl-8-aza-bicyclo[3.2.1]octane (79KS95)

8-tert-Butyloxycarbonyl-3-pentyl-8-aza-bicyclo[3.2.1]oct-2-ene (79KS94) (0.199 g, 0.712 mmol) was dissolved in CHCl$_3$ (3 mL) and TFA (1 mL) was added and the mixture was left stirring for 30 min. The mixture was then basified (2M NaOH), extracted (CHCl$_3$), dried (Na$_2$SO$_4$), filtered and concentrated. The resultant syrup was reacted according to GP3 to give the title compound (79KS95) (0.126 g, 98%). $^1$H NMR (CDCl$_3$) δ 0.84 (t, 3H, J=7.1 Hz, —CH$_2$CH$_2$CH$_2$CH$_2$CH$_3$), 1.13-1.46 (m, 8H), 1.65-1.77 (m, 3H), 1.88-2.00 (m, 2H), 2.16 (ddd, 2H, J=5.3 Hz, 8.3 Hz, 13.5 Hz), 3.62 (br s, 2H), 5.80 (br s, 1H, NH); $^{13}$C NMR (CDCl$_3$) δ 14.2 (—CH$_2$CH$_2$CH$_2$CH$_2$CH$_3$), 22.8 (—CH$_2$CH$_2$CH$_2$CH$_3$), 28.0, 28.3, 28.7, 28.8, 32.0, 35.1, 37.6, 54.0 (C2+C5).

3.18 8-tert-Butyloxycarbonyl-3-hexyl-8-aza-bicyclo[3.2.1] octane (79KS81)

8-tert-Butyloxycarbonyl-3-hexyl-8-aza-bicyclo[3.2.1]oct-2-ene (79KS79) (0.035 g, 0.119 mmol) was reacted according to GP3 to give the title compound (79KS81) (0.027 g, 77%). $^1$H NMR (CDCl$_3$) δ 0.85 (m, 3H, —CH$_2$CH$_2$CH$_2$CH$_2$CH$_2$CH$_3$), 1.10-1.40 (m, 11H), 1.45 (s, 9H, Boc-CH$_3$), 1.51-1.55 (m, 2H), 1.58-1.63 (m, 2H), 1.69-1.82 (m, 1H), 1.85-1.95 (m, 2H), 4.05-4.25 (m, 2H); $^{13}$C NMR (CDCl$_3$) δ 14.2 (—CH$_2$CH$_2$CH$_2$CH$_2$CH$_2$CH$_3$), 22.8 (—CH$_2$CH$_2$CH$_2$CH$_2$CH$_3$), 26.9, 28.2, 28.5, 28.8 (Boc-CH$_3$), 29.7, 32.1, 37.2, 37.7, 38.5, 53.5, 54.2, 79.0 (—C(CH$_3$)$_3$), 153.7 (C=O).

3.19 General Method 4 (GP4)

NaH (55% in mineral oil, 5 equiv) was washed with heptane (2-10 mL) and covered with dry THF (5-20 mL). This was then stirred vigorously followed by the addition of a solution of 1-tert-Butyloxycarbonylpiperidin-4-ol (1.0 equiv) in dry THF (5-20 mL) was carefully added. The stirring was continued for 30 min before adding an alkylhalide (1.2 equiv) in small portions. The stirring was continued for another 18 h before quenching the reaction with water (10-100 mL). Then the mixture was extracted (EtOAc) followed by drying (Na$_2$SO$_4$) of the combined organic phase. Filtration and concentration in vacuo gave a syrup which was purified by column chromatography (SiO$_2$; EtOAc/heptane 1:6 which gave the desired products.

3.20 1-tert-Butyloxycarbonyl-4-(prop-2-ene-1-oxy)-piperidine (104KS20)

NaH (16.4 g, 55% in mineral oil, 375 mmol), 1-tert-Butyloxycarbonylpiperidin-4-ol (15.1 g, 75.0 mmol) and allyl bromide (10.9 g, 90.0 mmol) were reacted according to GP4 to give the title compound (104KS20) (14.8 g, 82%). $^1$H NMR (CDCl$_3$) δ 1.45 (s, 9H, Boc-CH$_3$), 1.45-1.60 (m, 2H), 1.76-1.86 (m, 2H), 3.08 (ddd, 2H, J=4.1 Hz, 9.5 Hz, 13.4 Hz), 3.45-3.54 (m, 1H), 3.70-3.84 (m, 2H), 3.98-4.07 (m, 2H), 5.16 (m, 1H, J=10.8 Hz, —OCH$_2$CH=CH$_c$H$_t$), 5.27 (m, 1H, J=16.7 Hz, —OCH$_2$CH=CH$_c$H$_t$), 5.85-5.98 (m, 1H, —OCH$_2$CH=CH$_c$H$_t$); $^{13}$C NMR (CDCl$_3$) δ 28.7 (Boc-CH$_3$), 31.3, 41.6, 69.1, 74.2, 79.6 (—C(CH$_3$)$_3$), 116.8 (—OCH$_2$CH=CH$_2$), 135.4 (—OCH$_2$CH=CH$_2$), 155.1 (C=O).

3.21 1-tertButyloxycarbonyl-4-(cyclobutylmethoxy)-piperidine (61KS51)

NaH (0.398 g, 55% in mineral oil, 9.94 mmol), 1-tertButyloxycarbonylpiperidin-4-ol (2.00 g, 9.94 mmol) and (Bromomethyl)cyclobutane (1.35 g, 9.04 mmol) were reacted according to GP4 to give the title compound (61KS51) (0.212 g, 9%). $^1$H NMR (CDCl$_3$) δ 1.40-1.58 (m, 11H), 1.68-1.96 (m, 6H), 2.00-2.15 (m, 2H), 2.55 (m, 1H), 3.10 (ddd, 2H, J=3.0 Hz, 8.3 Hz, 13.3 Hz), 3.35-3.50 (m, 3H), 3.70-3.83 (m, 2H); $^{13}$C NMR (CDCl$_3$) δ 18.8, 25.3, 28.7 (Boc-CH$_3$), 31.4, 35.6, 41.5, 72.9, 74.7, 79.6 (—C(CH$_3$)$_3$), 155.1 (C=O).

3.22 1-tertButyloxycarbonyl-4-hydroxymethyl-piperidine (61KS81)

4-(Hydroxymethyl)piperidine (0.953 g, 8.27 mmol) was dissolved in dioxane/water (1:1, 50 mL) followed by the addition of Boc$_2$O (2.17 g, 9.92 mmol) and NaHCO$_3$ (8.77 g, 82.7 mmol). The mixture was stirred at room temperature for 24 h before extraction with DCM was performed. The combined organic phase was washed consecutively with citric acid (5% sol.) and aqueous NaHCO$_3$ followed by drying (Na$_2$SO$_4$), filtration and evaporation of the solvent to give the title compound (61KS81) (1.75 g, 98%). $^1$H NMR (CDCl$_3$) δ 1.15 (dq, 2H, J=4.8 Hz, 12.4 Hz), 1.45 (s, 9H, Boc-CH$_3$), 1.58-1.75 (m 3H), 2.70 (t, 2H, J=12.0 Hz), 3.49 (d, 2H, J=6.0 Hz, —CH$_2$OH), 4.00-4.23 (m, 2H); $^{13}$C NMR (CDCl$_3$) δ 28.7 (Boc-CH$_3$), 30.3, 39.0, 43.7, 67.3, 67.8, 79.5 (—C(CH$_3$)$_3$), 155.1 (C=O).

3.23 1-tertButyloxycarbonyl-4-methoxymethyl-piperidine (61KS83)

MeI (0.094 g, 0.659 mmol, 1.1 eq), 1-tertButyloxycarbonyl-4-hydroxymethyl-piperidine (61KS81) (0.129 g, 0.599 mmol, 1.0 eq) and NaH (0.029 g, 55% in mineral oil, 0.719 mmol, 1.2 eq) were reacted according to GP4 to give the title compound (61KS83) (0.076 g, 56%). $^1$H NMR (CDCl$_3$) δ 1.10 (dq, 2H, J=4.7 Hz, 12.2 Hz), 1.40 (s, 9H, Boc-CH$_3$), 1.60-1.75 (m, 3H), 2.63 (t, 2H, J=12.7 Hz), 3.18 (d, 2H, J=6.0 Hz, —CH$_2$OCH$_3$), 3.29 (s, 3H, —CH$_2$OCH$_3$), 3.94-4.15 (m, 2H); $^{13}$C NMR (CDCl$_3$) δ 28.6 (Boc-CH$_3$), 29.2, 36.7, 43.9, 59.0, 77.8, 79.4 (—C(CH$_3$)$_3$), 155.0 (C=O).

3.24 1-tertButyloxycarbonyl-4-ethoxymethyl-piperidine (61KS90)

1-tertButyloxycarbonyl-4-hydroxymethyl-piperidine (61KS81) (0.100 g, 0.464 mmol), NaH (0.093 g, 55% in mineral oil, 2.32 mmol) and EtOMs (0.345 g, 2.78 mmol) were reacted according to GP4 to give the title compound (61KS90) (0.071 g, 63%). $^1$H NMR (CDCl$_3$) δ 1.08 (dq, 2H, J=4.1 Hz, 12.9 Hz), 1.14 (t, 3H, 6.8 Hz, —CH$_2$OCH$_2$CH$_3$), 1.42 (s, 9H, Boc-CH$_3$), 1.63-1.75 (m, 3H), 2.65 (t, 2H, 12.8 Hz), 3.21 (d, 2H, J=6.1 Hz, —CH$_2$OCH$_2$CH$_3$), 3.42 (q, 2H, J=6.8 Hz, —CH$_2$OCH$_2$CH$_3$), 3.96-4.14 (m, 2H); $^{13}$C NMR (CDCl$_3$) δ 15.3 (—CH$_2$OCH$_2$CH$_3$), 28.6 (Boc-CH$_3$), 29.3, 36.8, 66.6, 75.6, 79.4 (—C(CH$_3$)$_3$), 155.1 (C=O).

3.25 1-tertButyloxycarbonyl-4-hydroxyethyl-piperidine (61KS82)

4-Piperidineethanol (1.05 g, 8.13 mmol) was dissolved in dioxane/water (1:1, 50 mL) followed by the addition of Boc$_2$O (2.13 g, 9.76 mmol) and NaHCO$_3$ (8.62 g, 81.3 mmol). The mixture was stirred at room temperature for 24 h before extraction with DCM was performed. The combined organic phase was washed consecutively with citric acid (5% sol.) and aqueous NaHCO$_3$ followed by drying (Na$_2$SO$_4$), filtration and evaporation of the solvent to give the title compound (61KS82) (1.77 g, 95%). $^1$H NMR (CDCl$_3$) δ 1.12 (dq, 2H, J=4.6 Hz, 11.8 Hz), 1.35-1.55 (m, 14H), 2.70 (t, 2H, J=12.8 Hz), 3.70 (t, 2H, J=6.3 Hz, —CH$_2$CH$_2$OH), 3.95-4.20 (m, 2H); $^{13}$C NMR (CDCl$_3$) δ 28.7 (Boc-CH$_3$), 32.8, 39.5, 44.2, 60.5, 67.3, 79.4 (—C(CH$_3$)$_3$), 155.1 (C=O).

3.26 1-tertButyloxycarbonyl-4-(2-methoxyethyl)-piperidine (61KS86)

MeI (3.72 g, 2.62 mmol), 1-tertButyloxycarbonyl-4-hydroxyethyl-piperidine (61KS82) (1.00 g, 4.36 mmol) and NaH (0.872 g, 55% in mineral oil, 21.8 mmol) were reacted according to GP4 to give the title compound (61KS86) (0.447 g, 42%). $^1$H NMR (CDCl$_3$) δ 1.10 (dq, 2H, J=4.2 Hz, 12.2 Hz), 1.38-1.70 (m, 14H), 2.68 (t, 2H, 12.6 Hz), 3.32 (s, 3H, —CH$_2$CH$_2$OCH$_3$), 3.40 (t, 2H, J=6.0 Hz, —CH$_2$CH$_2$OCH$_3$), 4.00-4.15 (m, 2H); $^{13}$C NMR (CDCl$_3$) δ 28.7 (Boc-CH$_3$), 32.4, 33.1, 36.4, 44.1, 58.8 (—CH$_2$CH$_2$OCH$_3$), 70.4 (—CH$_2$CH$_2$OCH$_3$), 79.4 (—C(CH$_3$)$_3$), 155.1 (C=O).

3.27 General Procedure 5 (GP5)

The alkene (1.0 equiv) was dissolved in MeOH (10-50 mL) and ammonium formate (10 equiv) was added. The reaction flask was then flushed with argon before adding Pd(10%)/C (30-700 mg). The reaction mixture was stirred for 4 h before the catalyst was filtered off using celite as filter aid. After concentration the product was taken up in DCM (5-30 mL) and filtered through cotton wool and concentrated to give the desired products.

3.28 1-tertButyloxycarbonyl-4-propoxy-piperidine (104KS21)

1-tertButyloxycarbonyl-4-(prop-2-ene-1-oxy)-piperidine (104KS20) (7.60 g, 31.5 mmol), ammonium formate (20 g, 315 mmol) and Pd(10%)/C (0.500 g) were reacted according to GP5 to give the title compound (104KS21) (5.61 g, 73%). $^1$H NMR (CDCl$_3$) δ 0.90 (m, 3H), 1.42 (s, 9H, Boc-CH$_3$), 1.35-1.60 (m, 4H), 1.70-1.85 (m, 2H), 3.00-3.15 (m, 2H), 3.30-3.44 (m, 3H), 3.65-3.70 (2H); $^{13}$C NMR (CDCl$_3$) δ 10.8 (—OCH$_2$CH$_2$CH$_3$), 23.5 (—OCH$_2$CH$_2$CH$_3$), 28.6 (Boc-CH$_3$), 31.3, 41.5 (C2 and C3), 69.9, 74.5 (C4 and —OCH$_2$CH$_2$CH$_3$), 79.5 (—C(CH$_3$)$_3$), 155.0 (C=O).

3.29 1-tertButyloxycarbonyl-4-(isobutoxy)-piperidine (61KS66)

3-Bromo-2-methylpropen (0.578 g, 4.28 mmol), NaH (0.189 g, 55% in mineral oil, 4.71 mmol), 1-tertButyloxycarbonylpiperidin-4-ol (0.948 g, 4.71 mmol), Pd(10%)/C (0.700 g), ammonium formate (1.84 g, 2.91 mmol) were reacted according to GP4 and GP5 to give the title compound (61KS66) (0.740 g, 67% over 2 steps). $^1$H NMR (CDCl$_3$) δ 0.90 (d, 6H, J=6.7 Hz, —OCH$_2$CH(CH$_3$)$_2$), 1.44 (s, 9H, Boc-CH$_3$), 1.46-1.56 (m, 2H), 1.73-1.87 (m, 3H), 3.15 (ddd, 2H, J=3.2 Hz, 8.5 Hz, 13.1 Hz), 3.19 (d, 2H, J=6.7 Hz, —OCH$_2$CH(CH$_3$)$_2$), 3.39 (tt, 1H, J=3.2 Hz, 8.0 Hz), 3.65-3.76 (m, 2H); $^{13}$C NMR (CDCl$_3$) δ 19.6, 28.6, 28.7 (Boc-CH$_3$), 31.2, 41.4, 74.6 (C4), 75.2 (—OCH$_2$CH(CH$_3$)$_3$), 155.1 (C=O).

3.30 4-Propyloxypiperidine (79KS66)

To solution of the Boc-protected piperidine 1-t-butyloxycarbonyl-4-propyloxypiperidine (104KS21) (12.6 g, 51.8 mmol) in DCM (30 mL) was carefully added TFA (25 mL) under stirring. The mixture was left stirring for 18 h and concentrated in vacuo. To the remaining syrup was added 2M NaOH (20 mL) and this mixture was extracted with DCM. The combined organic phase was dried (Na$_2$SO$_4$), filtered and concentrated to give the title compound (79KS66) (7.4 g, quant.) as a yellow oil. The material was used for the next reaction step without further purification. $^1$H NMR (CDCl$_3$): δ 0.89 (t, 3H, J=7.4 Hz, —OCH$_2$CH$_2$CH$_3$), 1.40-1.50 (m, 2H), 1.55 (sixt, 2H, J=7.4 Hz, —OCH$_2$CH$_2$CH$_3$), 1.84-1.94 (m, 2H), 2.64 (ddd, 2H, J=3.0 Hz, 9.8 Hz, 12.7 Hz), 3.35 (dt, 2H, J=1.5 Hz, 12.7 Hz), 3.21 (br s, 1H, NH), 3.30-3.37 (m, 1H, H4), 3.35 (td, 2H, J=1.2 Hz, 7.4 Hz, —OCH$_2$CH$_3$); $^{13}$C NMR (CDCl$_3$): δ 10.8 (—OCH$_2$CH$_2$CH$_3$), 23.5 (—OCH$_2$CH$_2$CH$_3$), 32.5, 44.1 (C2 and C3), 69.7 (—OCH$_2$CH$_2$CH$_3$), 74.8 (C4).

3.31 4-Cyclohexylmethyl-piperidine (56NK128)

Platinium dioxide (200 mg) was added to 4-benzylpiperidine (1.75 g, 10 mmol) in EtOH (20 ml) and HCl in dioxan (20 ml, 4 M). The flask was evacuated, flooded with hydrogen and this procedure was repeated twice. The reaction was stirred vigorously at r.t. for 72 h then platinium oxide (200 mg) was added and the reaction was stirred at r.t. for 18 h. The reaction mixture was filtered through Celite eluting with EtOAc and the solute concentrated in vacuo. Ether (50 ml) was added and the reaction concentrated in vacuo. Water (50 ml) and ether (50 ml) were added then sodium hydroxide (2 M) was added until pH 12. The phases were separated and the aqueous phase was extracted with ether (2×50 ml). The organic phases were combined, washed with brine (20 ml), dried (K$_2$CO$_3$), filtered and carefully concentrated in vacuo to give the crude title compound (56NK128) as a pale yellow oil (1.42 g, 78%). $^1$H NMR (CDCl$_3$) δ 3.04 (m, 2H), 2.56 (m, 2H), 1.72-1.55 (m, 9H), 1.45 (m, 1H), 1.32 (m, 1H), 1.18 (m, 2H), 1.05 (m, 4H), 0.83 (m, 2H); HPLC-MS (ammonium acetate) [M+H]$^+$=182.3 (calc. 182.2).

3.32 4-(2-Ethoxyethyl)piperidine (56NK129)

4-(2-Ethoxyethyl)pyridine (0.151 g, 1.0 mmol) was dissolved in EtOH (4 ml) and acetic acid (0.5 ml) and the flask was evacuated, flooded with hydrogen and this procedure was repeated twice. Platinum oxide (0.040 g) was added and the reaction was stirred vigorously at r.t. for 18 h. The reaction mixture was filtered through Celite eluting with EtOAc and the solute concentrated in vacuo. Ether (20 ml) was added and the reaction concentrated in vacuo. Sodium hydroxide (2 ml, 2 M) was added and the product was extracted into ether (2×20 ml). The organic phases were dried (K$_2$CO$_3$), filtered and carefully concentrated in vacuo to give the crude title compound (56NK129) as a yellow oil (0.154 g, 98%). $^1$H NMR (CDCl$_3$) δ 3.45 (m, 4H), 3.03 (m, 2H), 2.58 (m, 2H), 1.76 (br. S, 1H), 1.66 (m, 2H), 1.51 (m, 3H), 1.18 (t, J=7.5 Hz, 3H), 1.11 (m, 2H); HPLC-MS (ammonium acetate) [M+H]$^+$=158.2 (calc. 158.2).

3.33 4-Cyclohexylpiperidine (75NK45)

Platinium dioxide (0.200 g) was added to 4-phenylpiperidine (1.55 g, 10 mmol) in EtOH (40 ml) and HCl in dioxan (5 ml, 4 M). The flask was evacuated, flooded with hydrogen and this procedure was repeated twice. The reaction was stirred vigorously at r.t. for 72 h then filtered through Celite eluting with EtOAc and the solute was concentrated in vacuo to give a white solid. Water (30 ml) was added followed by sodium hydroxide (20 ml, 2 M) and the product was extracted into EtOAc (3×50 ml). The organic phase was washed with brine (20 ml), dried (K$_2$CO$_3$), filtered and carefully concentrated in vacuo to give the crude title compound (75NK45) as a pale yellow oil (1.38 g, 82%). $^1$H NMR (CDCl$_3$) δ 3.07 (m, 2H), 2.58 (m, 2H), 1.93 (br. s, 1H), 1.71 (m, 4H), 1.64 (m, 4H), 1.16 (m, 6H), 0.95 (m, 2H); HPLC-MS (ammonium acetate) [M+H]= 168.2 (calc. 168.3).

3.35 General Procedure 6 (GP6)

A 4 ml vial was charged with Aniline (1 equiv) and carbonyldiimidazole (1.3 equiv) in DMF (1 ml) and shaken at 60° for 4 h. The reaction was cooled to r.t. and 4 M HCl added (1 ml). The product was extracted into ethyl acetate (2×1 ml) and the combined org. layer filtered through a WHATMAM FT 5.0 μm PTFE column. The solute was concentrated in vacuo and used without further purification.

3.36 4-Methyl-3H-benzooxazol-2-one (86KK20a)

2-Hydroxy-6-methylanilin (0.154 g, 1.25 mmol) and carbonyldiimidazole (0.250 g, 1.54 mmol) were reacted according to GP6 to give the crude title compound (86KK20a).

3.37 5,7-Dimethyl-3H-benzooxazol-2-one (86KK20b)

2-Hydroxy-3,5-dimethylanilin (0.66 g, 1.21 mmol) and carbonyldiimidazole (0.250 g, 1.54 mmol) were reacted according to GP6 to give the crude title compound (86KK20b).

3.38 6-Methyl-3H-benzooxazol-2-one (86KK20c)

2-Hydroxy-4-methylanilin (0.145 g, 1.17 mmol) and carbonyldiimidazole (0.250 g, 1.54 mmol) were reacted according to GP6 to give the crude title compound (86KK20d).

3.39 5-Methyl-3H-benzooxazol-2-one (86KK20d)

2-Hydroxy-5-methylanilin (0.147 g, 1.19 mmol) and carbonyldiimidazole (0.250 g, 1.54 mmol) were reacted according to GP6 to give the crude title compound (86KK20d).

3.40 5-t-Butyl-3H-benzooxazol-2-one (86KK20e)

2-Hydroxy-5-t-butylanilin (0.203 g, 1.23 mmol) and carbonyldiimidazole (0.250 g, 1.54 mmol) were reacted according to GP6 to give the crude title compound (86KK20e).

3.41 6-Chloro-3H-benzooxazol-2-one (86KK20f)

4-Chloro-2-hydroxyanilin (0.179 g, 1.25 mmol) and carbonyldiimidazole (0.250 g, 1.54 mmol) were reacted according to GP6 to give the crude title compound (86KK20f).

3.42 5-Methoxy-3H-benzooxazol-2-one (86KK20i)

2-Hydroxy-5-methoxyanilin (0.175 g, 1.26 mmol) and carbonyldiimidazole (0.250 g, 1.54 mmol) were reacted according to GP6 to give the crude title compound (86KK20i).

3.43 6-Fluoro-3H-benzooxazol-2-one (86KK20j)

4-Fluoro-2-hydroxyanilin (0.154 g, 1.21 mmol) and carbonyldiimidazole (0.250 g, 1.54 mmol) were reacted according to GP6 to give the crude title compound (86KK20j).

3.44 5-Fluoro-3H-benzooxazol-2-one (86KK20k)

5-Fluoro-2-hydroxyanilin (0.117 g, 0.92 mmol) and carbonyldiimidazole (0.250 g, 1.54 mmol) were reacted according to GP6 to give the crude title compound (86KK20k).

3.45 General Procedure 7 (GP7)

A 4 ml vial was charged with hydroxybenzoic acid (1 equiv) and carbonyldiimidazole (1.2 equiv) in THF (1 ml) and shaken at 60° for 20 h. The reaction was cooled to r.t., 4 M HCl added (1 ml), and the product was extracted into EtOAc (2×1 ml). The combined org. layer was dried over $Na_2SO_4$ and concentrated in vacuo before being purified by flash column chromatography (CC) give of the product.

3.46 5,7-Dichloro-6-ethyl-3H-benzooxazol-2-one (97KK10)

3,5-Dichloro-4-ethyl-2-hydroxybenzoic acid (0.288 g, 1.40 mmol) and carbonyldiimidazole (0.275 g, 1.70 mmol) were reacted according to GP7. Purified by flash CC ($SiO_2$; DCM/MeOH 40:1) to give the title compound (97KK10) (0.269 g, 83%). $^1$H-NMR (MeOH) δ 1.14 (t, J=7.4 Hz, $CH_3$), 2.92 (q, J=7.4 Hz, $CH_2$), 7.04 (s, 1H); $^{13}$C (MeOH) δ 13.2, 24.9, 110.4, 116.4, 130.2, 130.9, 134.4, 141.2, 155.8.

3.47 7-Fluoro-3H-benzooxazol-2-one (97KK09a)

3-Fluoro-2-hydroxybenzoic acid (0.265 g, 2.08 mmol) and carbonyldiimidazole (0.352 g, 2.17 mmol) were reacted according to GP7. Purified by flash CC ($SiO_2$; DCM/MeOH 20:1) to give the title compound (97KK09a) (0.189 g, 59%). $^1$H-NMR ($CDCl_3$) δ 6.90-6.85 (m, 1 H), 7.38-7.33 (m, 1H), 7.86-7.83 (m, 1H), 10.38 (br. s, 1H).

3.48 5-Bromo-7-fluoro-3H-benzooxazol-2-one (97KK09b)

5-Bromo-3-fluoro-2-hydroxybenzoic acid (0.080 g, 0.39 mmol) and carbonyldiimidazole (0.075 g, 0.46 mmol) was reacted according to GP7. Purified by flash CC ($SiO_2$; DCM/MeOH 20:1) to give the title compound (97KK09b) (0.055 g, 61%). $^1$H-NMR (MeOD) δ 6.90-6.85 (m, 1H), 7.10-7.03 (m, 1H).

3.49 5,7-Dichloro-6-methyl-3H-benzooxazol-2-one (97KK09c)

3,5-Dichloro-2-hydroxy-4-methylbenzoic acid (0.331 g, 1.72 mmol) and carbonyldiimidazole (0.285 g, 1.76 mmol) were reacted according to GP7. Purified by flash CC ($SiO_2$; DCM/MeOH 20:1) to give the title compound (97KK09c) (0.240 g, 64%). $^1$H-NMR (MeOD) δ 2.43 (s, $CH_3$), 7.05 (s, 1H).

3.50 6,7-Difluoro-3H-benzooxazol-2-one (97KK11)

3,4-Difluoro-2-hydroxybenzoic acid (0.329 g, 2.27 mmol) and carbonyldiimidazole (0.390 g, 2.41 mmol) were reacted according to GP7. Purified by flash CC ($SiO_2$; DCM/MeOH 40:1) to give the title compound (97KK11) (0.139 g, 36%). $^1$H-NMR (MeOD) δ 6.83-6.80 (m, 1 H), 7.08-7.01 (m, 1 H); $^{13}$C-NMR (MeOD) δ 105.6 (J=4.5 Hz, J=7.8 Hz), 112.6 (J=20.3 Hz), 129.6, 133.1 (J=4.5 Hz, J=10.3 Hz), 136.7 (J=17.8 Hz, J=250.3 Hz), 148.1 (J=10.0 Hz, J=240.0 Hz), 156.3.

3.51 General Procedure 8 (GP8)

A 4 ml vial was charged with carboxylic acid (1 equiv), diphenylphosphoryl azide (1 equiv), triethylamine (1 equiv), and toluene (4 ml). The mixture was shaken at 110° under an Argon atmosphere for 20 h. The reaction mixture was cooled to r.t., water added (1 ml), and the product was extracted into ethyl acetate (2×1 ml). The combined org. layer was concentrated in vacuo before being purified by using an Isco CombiFlasch Sq 16× to give the product.

3.52 7-Methyl-3H-benzooxazol-2-one (86KK37a)

2-Hydroxy-3-methylbenzoic acid (0.303 g, 1.99 mmol), diphenylphosphoryl azide (0.548 g, 1.99 mmol), and $Et_3N$ (0.201 g, 1.99 mmol) were reacted according to GP8. Purified by using an Isco CombiFlash Sq 16× [10 g silica column, eluting 0-50% EtOAc in n-heptane (31 min) then 50% EtOAc in n-heptane (20 min)] to give the title compound (86KK37a) (0.204 g, 69%). $^1$H-NMR ($CDCl_3$) δ 2.39 (s, $CH_3$), 7.08-7.04 (m, 1 H), 6.94-6.92 (m, 2 H), 9.29 (br. s, 1 H); $^{13}$C-NMR ($CDCl_3$) δ 14.7, 107.7, 121.0, 124.1, 124.5, 129.1, 142.9, 156.2.

3.53 7-Isopropyl-3H-benzooxazol-2-one (86KK37b)

2-Hydroxy-3-isopropylbenzoic acid (0.342 g, 1.90 mmol), diphenylphosphoryl azide (0.523 g, 1.90 mmol), and $Et_3N$ (0.192 g, 1.90 mmol) were reacted according to GP8. Purified by using an Isco CombiFlash Sq 16× [10 g silica column, eluting 0-50% EtOAc in n-heptane (31 min) then 50% EtOAc in n-heptane (20 min)] to give the title compound (97KK37b) (0.263 g, 78%). $^1$H-NMR ($CDCl_3$) δ 1.33 (d, J=7.0, 2 $CH_3$), 3.24 (p, J=7.0, CH), 7.00-6.94 (m, 2 H), 7.12-7.10 (m, 1 H), 9.58 (br. S, 1 H); $^{13}$C-NMR ($CDCl_3$) δ 22.5, 28.9, 107.8, 120.6, 124.4, 129.3, 131.9, 141.8, 156.5.

3.54 5,7-Diisopropyl-3H-benzooxazol-2-one (86KK39a)

2-Hydroxy-3,5-diisopropylbenzoic acid (0.378 g, 1.70 mmol), diphenylphosphoryl azide (0.468 g, 1.70 mmol), and $Et_3N$ (0.172 g, 1.70 mmol) were reacted according to GP8. Purified by using an Isco CombiFlash Sq 16× [10 g silica column, eluting 0-50% EtOAc in n-heptane (41 min) then 50% EtOAc in n-heptane (10 min)] to give the title compound (86KK39a) (0.234 g, 63%). $^1$H-NMR (CDCl$_3$) δ 1.25 (d, J=7.0, CH$_3$), 1.25, (d, J=6.8, CH$_3$), 1.34 (d, J=6.8, CH$_3$), 1.34 (d, J=7.0, CH$_3$), 2.94-2.87 (m, CH), 3.24-3.17 (m, CH), 6.89-6.83 (m, 2 H), 10.23 (br. S, 1 H); $^{13}$C-NMR (CDCl$_3$) δ 22.6, 24.5, 29.4, 34.6, 105.9, 118.9, 129.6, 131.2, 140.1, 145.7, 157.3.

3.55 5-7-Dibromo-3H-benzooxazol-2-one (86KK39c)

3,5-Dibromo-2-hydroxybenzoic acid (0.477 g, 1.61 mmol), diphenylphosphoryl azide (0.443 g, 1.61 mmol), and Et$_3$N (0.163 g, 1.61 mmol) were reacted according to GP8. Purified by using an Isco CombiFlash Sq 16× [(10 g silica column, eluting 0-50% EtOAc in n-heptane (31 min) then 50% EtOAc in n-heptane (20 min)] to give the title compound (86KK39d) (0.345 g, 73%). $^1$H-NMR (MeOD+CDCl$_3$) δ 7.17 (s, 1 H), 7.38 (s, 1 H); $^{13}$C-NMR (MeOD+CDCl$_3$) δ 103.2, 113.0, 117.4, 128.3, 133.3, 142.4, 155.2.

3.56 6-Methoxy-3H-benzooxazol-2-one (86KK39d)

2-Hydroxy-4-methoxybenzoic acid (0.433 g, 2.58 mmol), diphenylphosphoryl azide (0.548 g, 2.58 mmol), and Et$_3$N (0.261 g, 2.58 mmol) were reacted according to GP8. Purified by using an Isco CombiFlash Sq 16× [(10 g silica column, eluting 0-50% EtOAc in n-heptane (31 min) then 50% EtOAc in n-heptane (20 min)] to give the title compound (86KK39d) (0.216 g, 50%). $^1$H-NMR (DMSO) δ 3.70 (s, OCH$_3$), 6.70-6.68 (m, 1 H), 6.97-6.94 (m, 2 H), 11.36 (br. s, 1 H); $^{13}$C-NMR (DMSO) δ 56.5, 97.7, 109.9, 110.6, 124.3, 144.7, 155.5, 155.9.

3.57 4,6-Dimethoxy-3H-benzooxazol-2-one (86KK39e)

2-Hydroxy-4,6-dimethoxybenzoic acid (0.456 g, 2.30 mmol), diphenylphosphoryl azide (0.633 g, 2.30 mmol), and Et$_3$N (0.233 g, 2.30 mmol) were reacted according to GP8. Purified by using an Isco CombiFlash Sq 16× [10 g silica column, eluting 0-50% EtOAc in n-heptane (31 min) then 50% EtOAc in n-heptane (20 min)] to give the title compound (86KK39e) (0.050 g, 11%). $^1$H-NMR (DMSO) δ 3.71 (s, OCH$_3$), 3.81 (s, OCH$_3$), 6.41 (d, J=2.2, 1 H), 6.56 (d, J=2.2 Hz, 1H), 11.50 (br. s, 1 H); $^{13}$C-NMR (DMSO) δ 56.5, 56.6, 89.8, 95.6, 113.0, 144.9, 145.0, 155.4, 156.7.

3.58 4,5,7-Trichloro-3H-benxooxazol-2-one (97KK26)

3,5,6-Trichloro-2-hydroxybenzoic acid (0.498 g, 2.06 mmol), diphenylphosphoryl azide (0.567 g, 2.06 mmol), and Et$_3$N (0.208 g, 2.06 mmol) were reacted according to GP8. Purified by using an Isco CombiFlash Sq 16× [10 g silica column, eluting 0-30% EtOAc in n-heptane (43 min) then 30% EtOAc in n-heptane (10 min)] to give the title compound (97KK26) (0.344 g, 70%). $^1$H-NMR (MeOD) δ 7.24 (s, 1 H); $^{13}$C-NMR (MeOD) δ 113.3, 114.8, 123.8, 128.8, 132.3, 140.4, 155.0.

3.59 5,7-Diiodo-3H-benzooxazol-2one (92LH49)

A 4 ml vial was charged with 2-hydroxy-3,5-diiodobenzoic acid (0.780 g, 2.00 mmol), diphenylphosphoryl azide (0.202 g, 1.99 mmol), triethylamine (0.550 g, 2.00 mmol), and toluene (4 ml). The mixture was shaken at 110° under an Argon atmosphere for 20 h. The reaction mixture was cooled to r.t., water added (1 ml), and the product was extracted into ethyl acetate (2×1 ml). The combined org. layer was concentrated in vacuo before being purified twice by flash CC (SiO$_2$; DCM/MeOH 9:1 and then n-heptan/ EtOAc 1:1) to give the title compound (92LH49) (0.205 g, 26%). $^1$-NMR (DMSO) δ 7.34-7.32 (m, 1 H), 7.71-7.70 (m, 1 H), 11.96 (br. s, 1 H); $^{13}$C-NMR (DMSO) δ 75.3, 88.0, 117.7, 131.6, 136.8, 144.9, 152.6.

3.60 4-methoxy-3H-benzooxazol-2-one (92LH58)

A 4 ml vial was charged with 2-hydroxy-6-methoxybenzoic acid (0.336 g, 2.00 mmol), diphenylphosphoryl azide (0.202 g, 1.99 mmol), triethylamine (0.550 g, 2.00 mmol), and toluene (4 ml). The mixture was shaken at 110° under an Argon atmosphere for 20 h. The reaction mixture was cooled to r.t., water added (1 ml), and the product was extracted into ethyl acetate (2×1 ml). The combined org. layer was concentrated in vacuo give the crude title compound (92LH58) (0.345 g)

3.61 7-Nitro-3H-benzooxazol-2-one (92LH59)

A 4 ml vial was charged with 2-hydroxy-3-nitrobenzoic acid (0.66 g, 2.00 mmol), diphenylphosphoryl azide (0.202 g, 1.99 mmol), triethylamine (0.550 g, 2.00 mmol), and toluene (4 ml). The mixture was shaken at 110° under an Argon atmosphere for 20 h. The reaction mixture was cooled to r.t., water added (1 ml), and was extracted with ethyl acetate (2×1 ml). The water phase was added SiO$_2$ and concentrated in vacuo. The product was purified by flash CC (SiO$_2$; EtOAc) to give the title compound (92LH59) (0.230 g, 64%). $^1$H-NMR (DMSO) δ 7.42 7.30 (m, 2 H), 7.86-7.84 (m, 1 H).

3.62 4-Methyl-7-isopropyl-3H-benzooxazol-2-one (92LH71)

A 4 ml vial was charged with 2-hydroxy-3-isopropyl-6-methylbenzoic acid (0.389 g, 2.00 mmol), diphenylphosphoryl azide (0.202 g, 1.99 mmol), triethylamine (0.550 g, 2.00 mmol), and toluene (4 ml). The mixture was shaken at 110° under an Argon atmosphere for 20 h. The reaction mixture was cooled to r.t., water added (1 ml), and the product was extracted into ethyl acetate (2×1 ml). The combined org. layer was concentrated in vacuo before being purified by prep. RP-HPLC [conditions: stationary phase, Luna 15 um C18; column, 250×21.2 mm; mobile phase, 20 ml/min, H$_2$O/CH$_3$CN, ammoniumacetate buffer (25 nM)] to give the title compound (92LH71) (0.100 g, 26%). $^1$H-NMR (CDCl$_3$) δ 1.34-1.29 (m, 6 H), 2.37-2.35 (m, 3 H), 3.22-3.17 (m, 1 H), 6.94-6.87 (m, 2 H9, 10.70 (br. s, 1 H); $^{13}$C-NMR (CDCl$_3$) δ 15.8, 22.5, 28.8, 118.0, 120.2, 125.4, 128.6, 129.0, 141.4, 157.4.

3.63 7-Methyl-4-isopropyl-3H-benzooxazol-2-one (92LH76)

A 4 ml vial was charged with 2-hydroxy-3-methyl-6-isopropylbenzoic acid (0.389 g, 2.00 mmol), diphenylphosphoryl azide (0.202 g, 1.99 mmol), triethylamine (0.550 g, 2.00 mmol), and toluene (4 ml). The mixture was shaken at 110° under an Argon atmosphere for 20 h. The reaction mixture was cooled to r.t., water added (1 ml), and the product was extracted into ethyl acetate (2×1 ml). The combined org. layer was concentrated in vacuo before being purified by prep. RP-HPLC [conditions: stationary phase, Luna 15 um C18; column, 250×21.2 mm; mobile phase, 20 ml/min, H$_2$O/CH$_3$CN, ammoniumacetate buffer (25 nM)] to give the title compound (92LH76) (0.066 g, 17%). $^1$H-NMR (MeOD) δ 1.25 (d, J=6.9 Hz, CH$_3$), 1.26 (d, J=7.0 Hz, CH$_3$), 2.30 (s, CH$_3$), 3.01 (quint, J=6.9 Hz, CH), 6.95-6.86 (m, 2 H); $^{13}$C-NMR (CDCl$_3$) δ 14.2, 22.9, 30.1, 118.5, 121.4, 124.8, 128.6, 129.9, 143.6, 157.6.

3.64 General Procedure 9 (GP9)

A reaction flask was charged with benzothiazol-2-one (1 equiv), chloroiodoalkane (1 equiv), and base (1.5 equiv) in MeCH (3 ml) and stirred at r.t. for 24 h. The reaction was added water and the product extracted into CH$_2$Cl$_2$. The combined org. layer was dried over Na$_2$SO$_4$ and concentrated in vacuo before being purified by flash column chromatography (CC).

3.65 3-(2-Chloroethyl)-3H-benzothiazol-2-one (62KK38)

2-Hydroxybenzothiazol (0.508 g, 3.29 mmol), 2-chloro-1-iodoethane (0.499 g, 2.52 mmol), and $K_2CO_3$ (0.547 g, 3.96 mmol) in MeCN (10 ml) were reacted according to GP9. Purified by CC ($Al_2O_3$; DCM/n.heptane 1:2) to give the title compound (62KK38) (0.292 g, 54%).

3.66 3-(3-Chloropropyl)-3H-benzothiazol-2-one (62KK21)

2-Hydroxybenzothiazol (1.003 g, 6.50 mmol), 3-chloro-1-iodopropane (1.361 g, 6.66 mmol), and $K_2CO_3$ (1.021 g, 7.39 mmol) in MeCN (20 ml) were reacted according to GP9. Purified by CC ($SiO_2$; DCM/n.heptane 1:1) to give the title compound (62KK21) (0.847 g, 57%).

3.67 3-(4-Chlorobutyl)-3H-benzothiazol-2-one (62KK29)

2-Hydroxybenzothiazol (0.496 g, 3.22 mmol), 4-chloro-1-iodobutane (0.722 g, 3.24 mmol), and $K_2CO_3$ (0.576 g, 4.17 mmol) in MeCN (13 ml) were reacted according to GP9. Purified by CC ($SiO_2$; DCM/n.heptane 1:1) to give the title compound (62KK30) (0.487 g, 63%).

3.68 3-(2-Chloroethyl)-3H-benzooxazol-2-one (62KK39)

3H-benzooxazol-2-one (0.425 g, 3.05 mmol), 2-chloro-1-iodoethane (0.563 g, 2.84 mmol), and $K_2CO_3$ (0.647 g, 4.68 mmol) in MeCN (10 ml) were reacted according to GP9. Purified by CC ($Al_2O_3$; DCM/n.heptane 1:2) to give the title compound (62KK39) (0.158 g, 28%).

3.69 3-(3-Chloropropyl)-3H-benzooxazol-2-one (62KK30)

3H-benzooxazol-2-one (0.580 g, 4.16 mmol), 3-chloro-1-iodopropane (0.854 g, 4.18 mmol), and $K_2CO_3$ (0.691 g, 5.00 mmol) in MeCN (10 ml) were reacted according to GP9. Purified by CC ($SiO_2$; DCM/n.heptane 1:1, DCM) to give the title compound (62KK30) (0.133 g, 14%).

3.70 3-(4-Chlorobutyl)-3H-benzooxazol-2-one (62KK28)

3H-benzooxazol-2-one (0.419 g, 3.01 mmol), 4-chloro-1-iodobutane (0.677 g, 3.04 mmol), and $K_2CO_3$ (0.500 g, 3.62 mmol) in MeCN (12 ml) were reacted according to GP9. Purified by CC ($SiO_2$; DCM/n.heptane 1:1, DCM) to give the title compound (62KK28) (0.309 g, 45%).

3.71 3-(5-Chloropentyl)-3H-benzothiazol-2-one (107LH01)

2-Hydroxybenzothiazol (0.302 g, 2.0 mmol), 5-chloro-1-iodopentane (0.370 g, 2.0 mmol), and $Cs_2CO_3$ (0.977 g, 3.0 mmol) were reacted according to GP9. Purified by flash CC ($SiO_2$; DCM) to give the title compound (107LH01) (0.461 g, 90%). $^1$H NMR ($CDCl_3$) δ 1.59-1.53 (m, 2 H), 1.87-1.75 (m, 4 H), 3.53 (t, J=6.6 Hz, $CH_2$), 3.96 (t, J=7.2 Hz, $CH_2$), 7.44-7.03 (m, 4 H); $^{13}$C NMR ($CDCl_3$) δ 24.2, 27.0, 32.2, 42.6, 44.7, 110.6, 122.8, 123.0, 123.2, 126.4, 137.2, 170.0.

3.72 3-(6-Chlorohexyl)-3H-benzothiazol-2-one (107LH02)

2-Hydroxybenzothiazol (0.302 g, 2.0 mmol), 6-chloro-1-iodohexane (0.398 g, 2.0 mmol), and $Cs_2CO_3$ (0.977 g, 3.0 mmol) were reacted according to GP9. Purified by flash CC ($SiO_2$; DCM) to give the title compound (107LH02) (0.491 g, 91%). $^1$H NMR ($CDCl_3$) δ 1.53-1.40 (m, 4 H), 1.80-1.73 (m, 4 H), 3.52 (t, J=6.6 Hz, $CH_2$), 3.95 (t, J=7.2 Hz, $CH_2$), 7.44-7.03 (m, 4H); $^{13}$C NMR ($CDCl_3$) δ 26.2, 26.6, 27.6, 32.5, 42.7, 45.0, 110.6, 122.8, 123.0, 123.1, 126.4, 137.2, 170.0.

3.73 General Procedure 10 (GP10)

A 4 ml vial was charged with benzooxazol-2-one (1 equiv), 3-chloro-1-iodopropane (1.2 equiv), and $Cs_2CO_3$ (1.2 equiv) in $CH_3CN$ (1 ml) and shaken at r.t. for 20 h. The reaction mixture was added water (1 ml) and the product extracted into EtOAc (2×1 ml). The combined organic layer filtered through a WHATMAM FT 5.0 μm PTFE column and concentrated in vacuo before being purified by using an Isco CombiFlasch Sq 16× to give the product.

3.74 3-(3-Chloropropyl)-4-methyl-3H-benzooxazol-2-one (86KK21a)

Crude 4-methyl-3H-benzooxazol-2-one (86KK20a) DMF solution, 3-chloro-1-iodopropane (0.480 g, 1.47 mmol), and $Cs_2CO_3$ (0.299 g, 1.46 mmol) were reacted according to GP10. Purified by using an Isco CombiFlash Sq 16× [10 g silica column, eluting 0-25% EtOAc in n-heptane (33 min) then 25% EtOAc in n-heptane (10 min)] to give the title compound (86KK21a) (0.111 g). $^1$H-NMR ($CDCl_3$) δ 2.37-2.21 (m, $CH_2$), 2.55 (s, $CH_3$), 3.65 (t, J=6.1 Hz, $CH_2$), 4.14 (t, J=6.8 Hz, $CH_2$), 7.03-6.90 (m, 3 H); $^{13}$C-NMR ($CDCl_3$) δ 17.7, 32.6, 41.6, 41.9, 108.3, 120.0, 122.6, 127.2, 128.9, 143.1, 155.2.

3.75 3-(3-Chloropropyl)-5,7-dimethyl-3H-benzooxazol-2-one (86KK21b)

Crude 5,7-dimethyl-3H-benzooxazol-2-one (86KK20b) DMF solution, 3-chloro-1-iodopropane (0.480 g, 1.47 mmol), and $Cs_2CO_3$ (0.299 g, 1.46 mmol) were reacted according to GP10. Purified by using an Isco CombiFlash Sq 16× [10 g silica column, eluting 0-25% EtOAc in n-heptane (33 min) then 25% EtOAc in n-heptane (10 min)] to give the title compound (86KK21b) (0.094 g). $^1$H-NMR ($CDCl_3$) δ 2.28-2.21 (m, $CH_2$), 2.32 (s, $CH_3$), 2.35 (s, $CH_3$), 3.59 (t, J=5.9 Hz, $CH_2$), 3.94 (t, J=6.7 Hz, $CH_2$), 6.68 (s, 1H), 6.73 (s, 1 H); $^{13}$C-NMR ($CDCl_3$) δ 14.6, 21.7, 30.9, 39.7, 42.0, 106.4, 120.4, 124.9, 130.9, 133.9, 139.5, 155.1.

3.76 3-(3-Chloropropyl)-6-methyl-3H-benzooxazol-2-one (86KK21c)

Crude 6-methyl-3H-benzooxazol-2-one (86KK20c) DMF solution, 3-chloro-1-iodopropane (0.480 g, 1.47 mmol), and $Cs_2CO_3$ (0.299 g, 1.46 mmol) were reacted according to GP10. Purified by using an Isco CombiFlash Sq 16× [10 g silica column, eluting 0-25% EtOAc in n-heptane (33 min) then 25% EtOAc in n-heptane (3 min)] to give the title compound (86KK21c) (0.092 g). $^1$H-NMR ($CDCl_3$) δ 2.28-2.21 (m, $CH_2$), 2.38 (s, $CH_3$), 3.58 (t, J=6.5 Hz, $CH_2$), 3.97 (t, J=6.7 Hz, $CH_2$), 7.01-6.92 (m, 3 H); $^{13}$C-NMR ($CDCl_3$) δ 21.6, 30.9, 39.7, 41.9, 108.0, 111.0, 124.5, 129.0, 133.0, 143.0, 154.8.

3.77 3-(3-Chloropropyl)-5-methyl-3H-benzooxazol-2-one (86KK21d)

Crude 5-methyl-3H-benzooxazol-2-one (86KK20d) DMF solution, 3-chloro-1-iodopropane (0.480 g, 1.47 mmol), and $Cs_2CO_3$ (0.299 g, 1.46 mmol) were reacted according to GP10. Purified by using an Isco CombiFlash Sq 16× [10 g silica column, eluting 0-25% EtOAc in n-heptane (33 min) then 25% EtOAc in n-heptane (3 min)] to give the title compound (86KK21d) (0.062 g). $^1$H-NMR ($CDCl_3$) δ 2.29-2.22 (m, $CH_2$), 2.40 (s, $CH_3$), 3.60 (t, J=5.9 Hz, $CH_2$), 3.97 (t, J=6.7 Hz, $CH_2$), 6.91-6.87 (m, 2 H), 7.07-7.05 (m, 1 H); $^{13}$C-NMR ($CDCl_3$) δ 21.7, 30.9, 39.7, 41.9, 109.0, 109.9, 123.1, 131.3, 134.2, 140.9, 155.0.

3.78 5-t-Butyl-3-(3-Chloropropyl)-3H-benzooxazol-2-one (86KK21e)

Crude 5-t-butyl-3H-benzooxazol-2-one (86KK20e) DMF solution, 3-chloro-1-iodopropane (0.480 g, 1.47 mmol), and $Cs_2CO_3$ (0.299 g, 1.46 mmol) were reacted according to GP10. Purified by using an Isco CombiFlash Sq 16× [10 g silica column, eluting 0-25% EtOAc in n-heptane (33 min) then 25% EtOAc in n-heptane (3 min)] to give the title compound (86KK21e) (0.102 g). $^1$H-NMR ($CDCl_3$) δ 1.35 (br. s, C($CH_3$)$_3$), 2.31-2.25 (m, $CH_2$), 3.61 (t, J=5.9 Hz, CH$_2$), 4.02 (t, J=6.7, CH$_2$), 7.14-7.10 (m, 3 H). $^{13}$C-NMR (CDCl$_3$) δ 31.1, 31.9, 35.2, 39.4, 42.0, 105.7, 109.6, 119.6, 131.2, 140.8, 148.0, 155.1.

3.79  3-(3-Chloropropyl)-6-chloro-3H-benzooxazol-2-one (86KK21f)

Crude 6-Chloro-3H-benzooxazol-2-one (86KK20f) DMF solution, 3-chloro-1-iodopropane (0.480 g, 1.47 mmol), and Cs$_2$CO$_3$ (0.299 g, 1.46 mmol) were reacted according to GP10. Purified by using an Isco CombiFlash Sq 16× [10 g silica column, eluting 0-20% EtOAc in n-heptane (33 min) then 20% EtOAc in n-heptane (3 min)] to give the title compound (86KK21f) (0.200 g). $^1$H-NMR (CDCl$_3$) δ 2.22-2.16 (m, CH$_2$), 3.52 (t, J=5.9 Hz, CH$_2$), 3.93 (t, J=6.6 HZ, CH$_2$), 6.94-6.92 (m, 1 H), 7.19-7.11 (m, 2 H); $^{13}$C-NMR (CDl$_3$) δ 30.2, 39.3, 41.2, 108.4, 110.8, 123.8, 127.8, 129.6, 142.6, 153.8.

3.80  3-(3-Chloropropyl)-5-methoxy-3H-benzooxazol-2-one (86KK21i)

Crude 5-methoxy-3H-benzooxazol-2-one (86KK20i) DMF solution, 3-chloro-1-iodopropane (0.480 g, 1.47 mmol), and Cs$_2$CO$_3$ (0.299 g, 1.46 mmol) were reacted according to GP10. Purified by using an Isco CombiFlash Sq 16× [10 g silica column, eluting 0-20% EtOAc in n-heptane (33 min) then 20% EtOAc in n-heptane (3 min)] to give the title compound (86KK21i) (0.079 g). $^1$H-NMR (CDCl$_3$) δ 2.25-2.22 (m, CH$_2$), 3.60-3.57 (m, CH$_2$), 3.97-3.93 (m, CH$_2$), 3.80 (s, OCH$_3$), 6.65-6.58 (m, 2 H), 7.07-7.04 (m, 1 H); $^{13}$C-NMR (CDCl$_3$) δ 30.7, 39.5, 41.8, 56.1, 95.6, 107.1, 110.4, 132.0, 136.7, 155.1, 156.9.

3.81  3-(3-Chloropropyl)-6-fluoro-3H-benzooxazol-2-one (86KK21i)

Crude 6-fluoro-3H-benzooxazol-2-one (86KK20j) DMF solution, 3-chloro-1-iodopropane (0.480 g, 1.47 mmol), and Cs$_2$CO$_3$ (0.299 g, 1.46 mmol) were reacted according to GP10. Purified by using an Isco CombiFlash Sq 16× [10 g silica column, eluting 0-20% EtOAc in n-heptane (33 min) then 20% EtOAc in n-heptane (3 min)] to give the title compound (86KK21j) (0.157 g). $^1$H-NMR (CDCl$_3$) δ 2.22-2.15 (m, CH$_2$), 3.53 (t, J=6.1 Hz, CH$_2$), 3.92 (t, J=6.6 Hz, CH$_2$), 6.95-6.82 (m, 3H); $^{13}$C (CDCl$_3$) δ 30.6, 39.7, 41.7, 99.5 (J=28.7 Hz), 108.3 (J=9.4 Hz), 110.5 (J=24.2 Hz), 127.5 (J=1.9 Hz), 142.7 (J=13.6 Hz), 154.5, 158.8 (J=241.6).

3.82  3-(3-Chloropropyl)-5-fluoro-3H-benzooxazol-2-one (86KK21k)

Crude 5-fluoro-3H-benzooxazol-2-one (86KK20k) DMF solution, 3-chloro-1-iodopropane (0.480 g, 1.47 mmol), and Cs$_2$CO$_3$ (0.299 g, 1.46 mmol) were reacted according to GP10. Purified by using an Isco CombiFlash Sq 16× [10 g silica column, eluting 0-20% EtOAc in n-heptane (35 min) then 20% EtOAc in n-heptane (3 min)] to give the title compound (86KK21k) (0.078 g). $^1$H-NMR (CDCl$_3$) δ 2.28 (quint, J=6.3 Hz, CH$_2$), 3.62 (t, J=6.1 Hz, CH$_2$), 4.00 (t, J=6.7 Hz, CH$_2$), 6.87-6.80 (m, 2 H), 7.16-7.13 (m, 1 H); $^{13}$C-NMR (CDCl$_3$) δ 30.6, 39.9, 41.7, 97.0 (J=29.7), 108.8 (J=24.8), 110.8 (J=9.7), 132.1 (J=12.6), 138.6, 154.8, 159.7 (J=242.0 Hz).

3.83 General Procedure 11 (GP11)

A 4 ml vial was charged with 3-H-benzooxazol-2-one (1 equiv), 3-bromopropanol (1.2 equiv), diethyl azodicarboxylate (1.2 equiv), and triphenylphosphine (1.2 equiv) in THF (2 ml). The mixture was stirred at r.t under an Argon atmosphere for 20 h. The reaction mixture was concentrated in vacuo before being purified by using an Isco CombiFlasch Sq 16× to give the product.

3.84  3-(3-Bromopropyl)-6-methoxy-3H-benzooxazol-2-one (97KK01a)

6-Methoxy-3H-benzooxazol-2-one (86KK39d) (0.093 g, 0.56 mmol), 3-bromopropan-1-ol (0.093 g, 0.67 mmol), diethyl azodicarboxylate (0.117 g, 0.67 mmol), and PPh$_3$ (0.176 g, 0.67 mmol) in THF (4 ml) were reacted according to GP11. Purified by using an Isco CombiFlash Sq 16× [4 g silica column, eluting 0-80% DCM in n-heptane (37 min) then 80% DCM in n-heptane (10 min)] to give the title compound (97KK01a) (0.114 g, 71%). $^1$H-NMR (MeOD+CDCl$_3$) δ 2.30 (m, CH$_2$), 3.44 (t, J=6.5, CH$_2$), 3.95 (t, J=6.9, CH$_2$), 6.78-6.75 (m, 1 H), 6.85-6.84 (m, 1 H), 7.05-7.03 (m, 1 H); $^{13}$C-NMR (MeOD+CDCl$_3$) δ 30.2, 31.5, 41.4, 56.4, 98.3, 109.5, 110.3, 125.3, 144.1, 156.1, 157.3.

3.85  3-(3-Bromopropyl)-5,7-dibromo-3H-benzooxazol-2-one (97KK01b)

5,7-Dibromo-3H-benzooxazol-2-one (86KK39c) (0.138 g, 0.47 mmol), 3-bromopropan-1-ol (0.078 g, 0.56 mmol), diethyl azodicarboxylate (0.098 g, 0.56 mmol), and PPh$_3$ (0.148 g, 0.56 mmol) in THF (4 ml) was reacted according to GP11. Purified by using an Isco CombiFlash Sq 16× [4 g silica column, eluting 0-60% DCM in n-heptane (36 min) then 60% DCM in n-heptane (15 min)] to give the title compound (97KK09b) (0.152 g, 87%). $^1$H-NMR (MeOD+CDCl$_3$) δ 2.35-2.30 (m, CH$_2$), 3.44 (t, J=6.3, CH$_2$), 3.96 (t, J=6.8 Hz, CH$_2$), 7.25 (s, 1 H), 7.41 (s, 1 H); $^{13}$C-NMR (MeOD+CDCl$_3$) δ 29.7, 30.8, 41.8, 103.6, 111.4, 117.4, 128.5, 133.3, 140.4, 153.9.

3.86  3-(3-Bromopropyl)-7-methyl-3H-benzooxazol-2-one (97KK03a)

7-Methyl-3H-benzooxazol-2-one (86KK37a) (0.100 g, 0.67 mmol), 3-bromopropan-1-ol (0.112 g, 0.80 mmol), diethyl azodicarboxylate (0.140 g, 0.80 mmol), and PPh$_3$ (0.211 g, 0.80 mmol) in THF (4 ml) was reacted according to GP11. Purified by using an Isco CombiFlash Sq 16× [4 g silica column, eluting 0-60% DCM in n-heptane (36 min) then 60% DCM in n-heptane (15 min)] to give the crude title compound (97KK03a) (0.072 g). $^1$H-NMR (MeOD) δ 2.31-2.26 (m, CH$_2$), 3.46 (t, J=6.5 Hz, CH$_2$), 3.94 (t, J=6.6, CH$_2$), 7.10-6.91 (m, 3 H).

3.87  3-(3-Bromopropyl)-7-isopropyl-3H-benzooxazol-2-one (97KK03b)

7-Isopropyl-3H-benzooxazol-2-one (86KK37b) (0.131 g, 0.74 mmol), 3-bromopropan-1-ol (0.123 g, 0.89 mmol), diethyl azodicarboxylate (0.155 g, 0.89 mmol), and PPh$_3$ (0.233 g, 0.89 mmol) in THF (4 ml) was reacted according to GP11. Purified by using an Isco CombiFlash Sq 16× [4 g silica column, eluting 0-60% DCM in n-heptane (35 min) then 60% DCM in n-heptane (15 min)] to give the crude title compound (97KK03b) (0.089 g). $^1$H-NMR (MeOD) δ 1.29 (d, J=7.0, 2 CH$_3$), 2.29 (quint, J=6.7 Hz, CH$_2$), 3.18 (sept, J=6.9 Hz, CH), 3.47 (t, J=6.5 Hz, CH$_2$), 3.97 (t, J=6.9, CH$_2$), 7.04-7.00 (m, 2 H), 7.17-7.13 (m, 1H).

3.88  3-(3-Bromopropyl)-5,7-diisopropyl-3H-benzooxazol-2-one (97KK03c)

5,7-Diisopropyl-3H-benzooxazol-2-one (86KK39a) (0.110 g, 0.50 mmol), 3-bromopropan-1-ol (0.083 g, 0.60 mmol), diethyl azodicarboxylate (0.104 g, 0.60 mmol), and PPh$_3$ (0.157 g, 0.60 mmol) in THF (4 ml) was reacted according to GP11. Purified by using an Isco CombiFlash Sq 16× [4 g silica column, eluting 0-60% DCM in n-heptane (35 min) then 60% DCM in n-heptane (15 min)] to give the crude title compound (97KK03c) (0.078 g). $^1$H-NMR (MeOD) δ 1.25 (d, J=6.8 Hz, 2 CH$_3$), 1.30 (d, J=7.0 Hz, 2 CH$_3$), 2.30 (quint, 6.7 Hz, CH$_2$), 2.93 (sept, J=6.8 Hz, CH), 3.15 (sept, J=6.9 Hz, CH), 3.49 (t, J=6.5 Hz, CH$_2$), 3.98 (t, J=6.7 Hz, CH$_2$), 6.88 (s, 1 H), 6.96 (s, 1 H).

3.89 3-(3-Bromopropyl)-4,6-dimethoxy-3H-benzooxazol-2-one (97KK05b)

4,6-Dimethoxy-3H-benzooxazol-2-one (86KK39e) (0.050 g, 0.26 mmol), 3-bromopropan-1-ol (0.043 g, 0.31 mmol), diethyl azodicarboxylate (0.54 g, 0.31 mmol), and PPh$_3$ (0.82 g, 0.31 mmol) in THF (4 ml) was reacted according to GP11. Purified by using an Isco CombiFlash Sq 16× [4 g silica column, eluting 0-60% DCM in n-heptane (35 min) then 60% DCM in n-heptane (15 min)] to give the title compound (97KK05b) (0.035 g, 43%). $^1$H-NMR (MeOD) δ 2.30 (quint, J=6.7 Hz, CH$_2$), 3.43 (t, J=6.6 Hz, CH$_2$), 3.77 (s, OCH$_3$), 3.88 (s, OCH$_3$), 4.07 (t, J=6.8 Hz, CH$_2$), 6.47-6.37 (m, 2 H).

3.90 3-(3-Bromopropyl)-7-fluoro-3H-benzooxazol-2-one (97KK12a)

7-Fluoro-3H-benzooxazol-2-one (97KK09a) (0.186 g g, 1.21 mmol), 3-bromopropan-1-ol (0.202 g, 1.45 mmol), diethyl azodicarboxylate (0.253 g, 1.45 mmol), and PPh$_3$ (0.381 g, 1.45 mmol) in THF (4 ml) was reacted according to GP11. Purified by using an Isco CombiFlash Sq 16× [4 g silica column, eluting 0-50% DCM in n-heptane (46 min) then 50% DCM in n-heptane (10 min)] to give the title compound (97KK12a) (0.100 g, 30%). $^1$H-NMR (CDCl$_3$) δ 2.32-2.26 (m, CH$_2$), 3.38 (t, J=6.1 Hz, CH$_2$), 3.94 (t, J=6.9 Hz, CH$_2$), 6.87-6.82 (m, 1 H), 7.10-7.05 (m, 2 H); $^{13}$C-NMR (CDCl$_3$') δ 2.98, 30.8, 41.4, 104.4 (J=3.9 Hz), 110.8 (J=16.8 Hz), 124.8 (J=7.1 Hz), 139.8 (J=14.5 Hz), 133.8 (J=4.8 Hz), 146.2 (J=250.3 Hz), 154.0

3.91 3-(3-Bromopropyl)-5,7-dichloro-6-methyl-3H-benzooxazol-2-one (97KK12b)

5,7-Dichloro-6-methyl-3H-benzooxazol-2-one (97KK09c) (0.239 g g, 1.10 mmol), 3-bromopropan-1-ol (0.183 g, 1.32 mmol), diethyl azodicarboxylate (0.230 g, 1.32 mmol), and PPh$_3$ (0.346 g, 1.32 mmol) in THF (4 ml) was reacted according to GP11. Purified by using an Isco CombiFlash Sq 16× [4 g silica column, eluting 0-50% DCM in n-heptane (46 min) then 50% DCM in n-heptane (10 min)] to give the crude title compound (97KK12b) (0.051 g).

3.92 General Procedure 12 (GP12)

The heterocycle (1 equiv) and NaI (2 equiv) in acetone (1 ml per mmol) were heated to 50° C. for 72 h then cooled to r.t. Aqueous sodium thiosulphate solution (10-20 ml) was added and the product was extracted into EtOAc (2×20-100 ml). The organic layer was dried (K$_2$CO$_3$), filtered and concentrated in vacuo before being purified.

3.93 1-(2-Iodoethyl)-1,3-dihydrobenzoimidazol-2-one (56NK93)

1-(2-Chloroethyl)-1,3-dihydrobenzoimidazol-2-one (178 mg, 0.905 mmol) was used according to GP12. The crude product was purified using an Isco CombiFlash Sq 16× [4.1 g silica column, eluting heptane (5 min), 0-40% EtOAc in heptane (20 min), 40% EtOAc in heptane (10 min)] to give the title compound (56NK93) as a pale yellow oil (204 mg, 78%). $^1$H NMR (CDCl$_3$) δ 9.26 (br. s, 1H), 7.10 (m, 3H), 7.04 (m, 1H), 4.28 (t, J=7.6 Hz, 2H), 3.44 (t, J=7.6 Hz, 2H); HPLC-MS (ammonium acetate) [M+H]$^+$=289.0.

3.94 1-(4-Iodobutyl)-1,3-dihydrobenzoimidazol-2-one (56NK94)

1-(4-Chlorobutyl)-1,3-dihydrobenzoimidazol-2-one (456 mg, 2.03 mmol) was used according to GP12. The crude product was purified using an Isco CombiFlash Sq 16× [10 g silica column, eluting heptane (2 min), 0-40% EtOAc in heptane (31 min), 40% EtOAc in heptane (15 min)] to give the title compound (56NK94) as a pale yellow oil (491 mg, 77%). $^1$H NMR (CDCl$_3$) δ 9.28 (br. s, 1H), 7.10 (m, 3H), 7.02 (m, 1H), 3.92 (m, 2H), 3.25 (m, 2H), 1.92 (m, 4H); HPLC-MS (ammonium acetate) [M+H]$^+$=317.0.

3.95 1-(3-Iodopropyl)-1,3-dihydrobenzoimidazol-2-one (56NK36)

1-(3-Chloropropyl)-1,3-dihydrobenzoimidazol-2-one (10.5 g, 50 mmol) was used according to GP12. The crude product was recrystallised from EtOAc to give the title compound (56NK36) as a while powder (12.15 g, 80%). $^1$H NMR (CDCl$_3$) δ 9.93 (br. s, 1H), 7.11 (m, 1H), 4.00 (t, J=6.2 Hz, 2H), 3.22 (t, J=6.8 Hz, 2H), 2.34 (pent, J=6.8 Hz, 2H); HPLC-MS (ammonium acetate) [M+H]$^+$=302.1.

3.96 1-(3-Iodopropyl)-3-methyl-1,3-dihydrobenzoimidazol-2-one (56NK85)

1-(3-Chloropropyl)-3-methyl-1,3-dihydrobenzoimidazol-2-one (852 mg, 3.79 mmol) was used according to GP12. The crude product was purified using an Isco CombiFlash Sq 16× [10 g silica column, eluting heptane (1 min), 0-40% EtOAc in heptane (25 min), 40% EtOAc in heptane (10 min)] to give the title compound (56NK85) as a pale yellow oil (1.02 g, 86%). $^1$H NMR (CDCl$_3$) δ 7.10 (m, 3H), 6.98 (m, 1H), 3.98 (t, J=6.8 Hz, 2H), 3.42 (s, 3H), 3.20 (t, J=6.8 Hz, 2H), 2.31 (pent, J=6.8 Hz, 2H); $^{13}$C NMR (CDCl$_3$) 6154.30, 130.01, 129.23, 121.28, 107.48, 107.47, 41.59, 32.40, 27.06, 2.17; HPLC-MS (ammonium acetate) [M+H]$^+$=317.0.

3.97 1-(2-Chloroethyl)-1,3-dihydrobenzoimidazol-2-one (56NK91)

Sodium hydride (400 mg, 10 mmol, 60% in oil) was washed with dry DMF (10 ml) under an argon atmosphere then DMF (10 ml) was added. The slurry of NaH in DMF was added slowly to 2-hydroxybenzimidazole (1.34 g, 10 mmol) in DMF (10 ml) at 0° C. under argon. The reaction was stirred at 0° C. for 20 min then 1-chloro-2-iodoethane (1.90 g, 10 mmol) in DMF (5 ml) was added slowly. The reaction was stirred at r.t. for 1.5 h then water (10 ml) was added and the reaction acidified with HCl (2M, few drops) then made basic with aqueous sodium hydrogen carbonate solution. The product was extracted with EtOAc (3×30 ml) and the organic layer was washed with aqueous sodium thiosulphate solution (10 ml), aqueous magnesium sulphate solution (4%, 2×10 ml), brine (10 ml), dried (K$_2$CO$_3$), filtered and concentrated in vacuo before being purified by using an Isco CombiFlash Sq 16× [10 g silica column, eluting heptane (5 min), 0-40% EtOAc in heptane (35 min), 40% EtOAc in heptane (20 min)] to give the title compound (56NK91) as a pale yellow oil (162 mg, 8%). $^1$H NMR (CDCl$_3$) δ 8.70 (br. s, 1H), 7.09 (m, 4H), 4.22 (t, J=6.5 Hz, 2H), 3.84 (t, J=6.5 Hz, 2H); $^{13}$C NMR (CDCl$_3$) δ 155.11, 130.28, 127.74, 121.91, 121.60, 109.63, 108.45, 42.75, 41.16.

3.98 1-(4-Chlorobutyl)-1,3-dihydrobenzoimidazol-2-one (56NK92)

Sodium hydride (400 mg, 10 mmol, 60% in oil) was washed with dry DMF (10 ml) under an argon atmosphere then DMF (10 ml) was added. The slurry of NaH in DMF was added slowly to 2-hydroxybenzimidazole (1.34 g, 10 mmol) in DMF (10 ml) at 0° C. under argon. The reaction was stirred at 0° C. for 20 min then 1-chloro-4-iodobutane (2.18 g, 10 mmol) in DMF (5 ml) was added slowly. The reaction was stirred at r.t. for 1.5 h then water (10 ml) was added and the reaction acidified with HCl (2M, few drops) then made basic with aqueous sodium hydrogen carbonate solution. The product was extracted with EtOAc (3×30 ml) and the organic layer was washed with aqueous sodium thiosulphate solution (10 ml), aqueous magnesium sulphate solution (4%, 2×10 ml), brine (10 ml), dried ($K_2CO_3$), filtered and concentrated in vacuo before being purified by using an Isco CombiFlash Sq 16× [10 g silica column, eluting heptane (5 min), 0-40% EtOAc in heptane (35 min), 40% EtOAc in heptane (20 min)] to give the title compound (56NK92) as a pale yellow oil (416 mg, 19%). $^1$H NMR ($CDCl_3$) δ 10.48 (br. s, 1H), 7.26-7.00 (m, 4H), 3.95 (t, J=6.8 Hz, 2H), 3.59 (t, J=6.3 Hz, 2H), 1.97 (m, 2H), 1.87 (m, 2H); $^{13}$C NMR ($CDCl_3$) δ 158.88, 130.08, 128.14, 121.56, 121.25, 109.82, 107.74, 44.32, 39.88, 29.53, 25.66; HPLC-MS (ammonium acetate) [M+H]$^+$=225.2.

3.99 1-(3-Chloropropyl)-3-methyl-1,3-dihydrobenzoimidazol-2-one (56NK01)

1-(3-Chloropropyl)-1,3-dihydrobenzoimidazol-2-one (2.10 g, 10 mmol), methyl iodide (1.5 ml, 25 mmol), sodium hydroxide (2 M, 5 ml, 10 mmol) and MeCN (10 ml) were stirred at r.t. 18 h. Water (10 ml) was added and the product was extracted into EtOAc (2×30 ml). The organic layer was washed with aqueous sodium thiosulphate solution (5 ml), brine (10 ml), dried ($K_2CO_3$), filtered and concentrated in vacuo before being purified by using an Isco CombiFlash Sq 16× [35 g silica column, eluting heptane (1 min), 0-50% EtOAc in heptane (40 min), 50% EtOAc in heptane (40 min)] to give the title compound (56NK01) as a pale yellow oil (1.93 g, 86%). $^1$H NMR ($CDCl_3$) δ 7.10 (m, 3H), 6.98 (m, 1H), 4.06 (t, J=6.6 Hz, 2H), 3.85 (t, J=6.6 Hz, 2H), 3.42 (s, 3H), 2.25 (pent, J=6.6 Hz, 2H); HPLC-MS (ammonium acetate) [M+H]$^+$=225.1.

3.100 3-(4-Chlorobutyl)-3H-benzooxazole-2-thione (56NK132)

Iodine (127 mg, 0.5 mmol) in DMF (2 ml) was added to 2-(4-chlorobutylsulfanyl)-benzooxazole (697 mg, 2.88 mmol) and the reaction was heated to 125° C. for 24 h then cooled to r.t. Aqueous sodium thiosulplate solution (5 ml) was added and the product was extracted with ether (3×30 ml). The organic phase was washed with aqueous magnesium sulphate solution (4%, 2×10 ml), brine (10 ml), dried ($K_2CO_3$), filtered and concentrated in vacuo. The crude product was purified using an Isco CombiFlash Sq 16× [4.1 g silica column, eluting heptane (3 min), 0-10% EtOAc in heptane (25 min), 10% EtOAc in heptane (2 min)] to give the title compound (56NK132) as a white powder (68 mg, 10%). $^1$H NMR ($CDCl_3$) δ 7.36 (m, 1H), 7.28 (m, 2H), 7.13 (m, 1H), 4.25 (t, J=7.2 Hz, 2H), 3.62 (t, J=6.2 Hz, 2H), 2.06 (m, 2H), 1.92 (m, 2H).

3.101 1-(3-Chloropropyl)-1H-indol-2,3-dione (85LM02).

A 500 ml flask was charged with 1H-indol-2,3-dione (isatin) (3.62 g, 25 mmol), 1-chloro-3-iodopropan (2.8 ml, 27 mmol) and $Cs_2CO_3$ (18 g, 55 mmol) in MeCN (200 ml). The mixture was stirred 40° C. for 48 hours. Water (50 ml) and EtOAc (50 ml) were added and the phases were separated. The aqueous phase was re-extracted with EtOAc (50 ml). The combined org. layer were dried ($Na_2SO_4$) and evaporated to dryness. The crude product was purified by to column chromatography ($SiO_2$; EtOAc/n-heptane 1:4) to give the title compound (85LM02) (4.2 g, 80%). $^1$H NMR ($CDCl_3$) δ 2.20 (qv, 2H), 3.60 (t, 2H), 3.90 (t, 2H), 7.00 (d, 1H), 7.15 (t, 1H), 7.55-7.65 (m, 2H); HPLC-MS (ammonium acetate) [M+H]$^+$=224.2.

3.102 1-(3-Iodopropyl)-1H-indol-2,3-dione (85LM05).

A 50 ml flask, charged with compound 1-(3-chloropropyl)-1H-indol-2,3-dione (85LM02) (0.232 g, 1 mmol) and NaI (0.327 g, 2.2 mmol) in acetone (10 ml), was stirred at 50° C. for 24 hours. Water (10 ml) was added and the phases were separated. The aqueous phase was re-extracted with acetone (10 ml). The combined organic phases were dried ($Na_2SO_4$) and evaporated to dryness to give the crude title compound (85LM05) (0.294 g). $^1$H NMR ($CDCl_3$) δ 2.20 (qv, 2H), 3.20 (t, 2H), 3.80 (t, 2H), 7.0 (d, 1H), 7.15 (t, 1H), 7.55-7.65 (m, 2H).

3.103 3-(1H-Indol-3-yl)propan-1-ol (85LM16B).

A suspension of $LiAlH_4$ (2.48 g, 65 mmol) in dry THF (140 ml) was stirred in a 500 ml flask. 3-(1H-indol-3-yl) propionic acid (5.38 g, 28 mmol) was dissolved in dry THF (20 ml) and added slowly. The mixture was heated to 35° C. Stirring was continued for 2 hours at 35° C. and overnight at room temperature. Water (20 ml) was added drop wise and very slowly, followed by addition of $H_2O/H_2SO_4$ (1:1) (50 ml). To the resulting mixture NaOH was added (until pH 7) and the two phases were separated. The organic phase was dried ($Na_2SO_4$) and evaporated to dryness to give the crude title compound (85LM16B) (5.0 g). The material was used for the next reaction step without further purification. $^1$H NMR ($CD_3OD$) δ 1.92 (qv, 2H), 2.80 (t, 2H), 3.61 (t, 2H), 7.00 (t, 1H), 7.05 (t, 1H), 7.33 (d, 1H), 7.55 (d, 1H).

3.104 Toluene-4-sulfonic acid 3-(1H-indol-3-yl)propyl ester (85LM17).

Crude 3-(1H-indol-3-yl)propan-1-ol (85LM16B) (5.0 g, 29 mmol) and pyridine (10 ml, 160 mmol) was dissolved in dry THF (140 ml) in a 100 ml flask. The mixture was cooled to −78° C. and p-toluenesulfonyl chloride (10.9 g, 57 mmol) dissolved in dry THF (10 ml) was slowly added followed by stirring at −78° C. for 1 hour and then heating to room temperature over a period of 20 minutes. The solution was washed with $H_2SO_4$ (10 ml, 1M) then saturated aqueous sodium bicarbonate (10 ml) and finally water (10 ml). The organic phase was dried ($Na_2SO_4$) and evaporated to dryness to give the crude title compound (85LM17) (4.0 g). The material was used for the next reaction step without further purification.

3.105 3-(3-Bromo-2-hydroxypropyl)-3H-benzothiazol-2-one (85LM04).

A 50 ml flask, charged with 2-hydroxybenzothiazol (0.650 g, 4.3 mmol), 1,3-dibromo-2-propanol (0.22 ml, 2.2 mmol) and $Cs_2CO_3$ (3.0 g, 9.2 mmol) in MeCN (20 ml), was stirred at 40° C. for 24 hours. Water (10 ml) and EtOAc (10 ml) were added and the phases were separated. The aqueous phase was re-extracted with EtOAc (10 ml). The combined organic phases were dried ($Na_2SO_4$) and evaporated to dryness to give the crude title compound (85LM04) (0.308 g). The material was used for the next reaction step without further purification.

3.106 3-(3-Chloro-2-methyl-propyl)-3H-benzothiazol-2-one (85LM13).

A 50 ml flask, charged with 2-hydroxybenzothiazol (0.603 g, 4.0 mmol), 1-bromo-3-chloro-2-methylpropan (0.56 ml, 4.8 mmol) and $Cs_2CO_3$ (2.86 g, 8.8 mmol) in $CH_3CN$ (20 ml), was stirred at 40° C. for 24 hours. Water (10 ml) and EtOAc (10 ml) were added and the phases were separated. The aqueous phase was re-extracted with EtOAc (10 ml). The combined organic phases were dried ($Na_2SO_4$) and evaporated to dryness. The crude product was subjected to column chromatography ($SiO_2$; EtOAc/n-heptane 1:8) to give the title compound (85LM13) (0.769 g, 80%). $^1$H NMR ($CDCl_3$) δ 1.10 (d, 3H), 2.45 (octet, 1H), 3.55 (d, 2H), 3.90 (dd, 1H), 4.05 (dd, 1H), 7.10-7.20 (m, 2H), 7.35 (t, 1H, 7.40 (d, 1H); HPLC-MS (ammonium acetate) [M+H]$^+$=242.1.

3.107 General Procedure 13 (GP13)

A 100 ml flask, charged with either (R)- or (S)-3-bromo-2-methyl-propanol (1 equiv), 2-hydroxybenzothiazol (1 equiv) mmol), and $Cs_2CO_3$ (1 equiv) in MeCN (30 ml), was stirred at 50° C. for 48 hours. Water (20 ml) and EtOAc (20 ml) were added and the phases were separated. The aqueous phase was re-extracted with EtOAc (20 ml). The combined org. layer was dried ($Na_2SO_4$) and concentrated in vacuo to give the crude product. The material was used for the next reaction step without further purification.

3.108 3-((R)-3-Hydroxy-2-methylpropyl)-3H-benzothiazol-2-one (85LM72-60)

(S)-3-Bromo-2-methylpropanol (0.760 g, 5.0 mmol), 2-hydroxybenzothiazol (0.751 g, 5.0 mmol), and $Cs_2CO_3$ (1.6 g, 5.0 mmol) in MeCN (30 ml) were reacted according to GP13 to give the title crude compound (85LM72-60) (1.3 g).

3.109 3-((S)-3-Hydroxy-2-methylpropyl)-3H-benzothiazol-2-one (85LM89-76).

(R)-3-Bromo-2-methylpropanol (0.760 g, 5.0 mmol), 2-hydroxybenzothiazol (0.751 g, 5.0 mmol), and $Cs_2CO_3$ (1.6 g, 5.0 mmol) in MeCN (30 ml) were reacted according to GP13 to give the title crude compound (85LM89-76) (1.3 g).

3.110 General Procedure 14 (GP14)

3-Hydroxyalkyl-3H-benzothiazol-2-one (1 equiv) and pyridine (4 equiv) was dissolved in dry DCM (50 ml) in a 100 ml flask. The mixture was stirred and cooled to −78° C. followed by slow addition of p-toluenesulfonyl chloride (5 equiv) dissolved in dry DCM (10 ml). Stirring was continued at −78° C. for 1 hour and at room temperature for 2 hours. The solution was washed with hydrochloric acid (10 ml, 1M) then saturated aqueous sodium bicarbonate (10 ml) and finally water (10 ml). The organic phase was dried ($Na_2SO_4$) and evaporated to dryness. The crude product was purified by column chromatography ($SiO_2$; DCM).

3.111 Toluene-4-sulfonic acid (R)-2-methyl-3-(2-oxobenzothiazol-3-yl)-propyl ester (85LM73-61).

3-((R)-3-Hydroxy-2-methylpropyl)-3H-benzothiazol-2-one (85LM72-60) (1.3 g, 2.8 mmol), pyridine (0.900 g, 11.4 mmol), and p-toluenesulfonyl chloride (2.7 g, 14.2 mmol) were reacted according to GP14 to give the title compound (85LM73-61) (0.90 g, 48%-2 steps). $^1$H NMR ($CDCl_3$) δ 1.0 (d, 3H), 2.45 (m, 4H), 3.80-3.90 (m, 2H), 3.90-4.00 (m, 2H), 7.0 (d, 1H), 7.15 (t, 1H), 7.25-7.35 (m, 3H), 7.40 (d, 1H), 7.75 (d, 2H).

3.112 Toluene-4-sulfonic acid (S)-2-methyl-3-(2-oxo-benzothiazol-3-yl)-propyl ester (85LM90-77).

3-((S)-3-Hydroxy-2-methylpropyl)-3H-benzothiazol-2-one (85LM89-76) (1.3 g, 2.8 mmol), pyridine (0.900 g, 11.4 mmol), and p-toluenesulfonyl chloride (2.7 g, 14.2 mmol) were reacted according to GP14 to give the title compound (85LM90-77) (0.90 g, 46%-2 steps). $^1$H NMR ($CDCl_3$) δ 1.0 (d, 3H), 2.45 (m, 4H), 3.80-3.90 (m, 2H), 3.90-4.00 (m, 2H), 7.0 (d, 1H), 7.15 (t, 1H), 7.25-7.35 (m, 3H), 7.40 (d, 1H), 7.75 (d, 2H).

3.113 3-(3-Iodopropyl)-3H-benzothiazol-2-one (61KS80).

3-(3-Chloropropyl)-3H-benzothiazol-2-one (62KK21) (1.58 g, 6.94 mmol) was dissolved in acetone (10 mL) and NaI (2.08 g, 13.9 mmol) was added. The mixture was heated to 50° C. under stirring for 18 h. A saturated aq. solution of $Na_2S_2O_3$ (5 mL) was added followed by extraction (EtOAc). The combined organic phase was dried ($Na_2SO_4$), filtered and concentrated in vacuo which gave the title compound (61KS80) (2.17 g, 98%) as a colourless oil which on prolonged standing crystallised to a white powder. This was sufficiently pure for further reaction. $^1$H NMR ($CDCl_3$) □ 2.25 (q, 2H, J=7.0 Hz, —$CH_2CH_2CH_2I$), 3.22 (t, 2H, J=7.0 Hz, —$CH_2CH_2CH_2I$), 4.04 (t, 2H, J=7.0 Hz, —$CH_2CH_2CH_2I$), 7.13-7.46 (m, 4H, Ar); $^{13}$C NMR ($CDCl_3$) □ 0.0 (—$CH_2CH_2CH_2I$), 29.8 (—$CH_2CH_2CH_2I$), 41.7 (—$CH_2CH_2CH_2I$), 108.8, 121.1, 121.1, 121.6, 124.8, 135.2 (Ar), 168.3 (C═O).

3.114 General Procedure 15 (GP15)

A 4 ml vial was charged with 3-chloroalkyl-3H-benzooxazol-2-one (1 equiv), 4-butylpiperidine (1 equiv), NaI (0.100 g, 0.67 mmol), and $K_2CO_3$ (0.075 g, 0.54 mmol) in MeCN (1 ml) and shaken at 50° C. for 20 h. The reaction mixture was cooled to r.t. and DCM was added (2 ml). Isocyanate resin (ca. 3 equiv, 1.1 mmol/g) was added and the mixture left at r.t. for 24 h. The mixture was filtered through cotton onto an acidic ion-exchange column. The column was washed with MeOH (2 column volumes) then the product was eluded of the column using 10% ammonium hydroxide in MeOH (2 column volumes) and concentrated in vacuo.

3.115 3-[2-(4-Butylpiperidin-1-yl)ethyl]-3H-benzothiazol-2-one (67KK20a)

3-(2-Chloroethyl)-3H-benzothiazol-2-one (62KK38) (0.043 g, 0.2 mmol) and 4-butylpiperidine (0.028 g, 0.2 mmol) were reacted according to GP15 to give the title compound (67KK20a) (0.008 g, 13%). HPLC-MS (ammonium acetate) $[M+H]^+$=319.4.

3.116 3-[2-(2-Ethylpiperidin-1-yl)ethyl]-3H-benzothiazol-2-one (67KK17f)

3-(2-Chloroethyl)-3H-benzothiazol-2-one (62KK38) (0.032 g, 0.15 mmol) and 2-ethylpiperidine (0.017 g, 0.15 mmol) were reacted according to GP15 to give the title compound (67KK17f) (0.003 g, 7%). HPLC-MS (ammonium acetate) $[M+H]^+$=291.3.

3.117 3-[2-(4-Methylpiperidin-1-yl)ethyl]-3H-benzothiazol-2-one (67KK20c)

3-(2-Chloroethyl)-3H-benzothiazol-2-one (62KK38) (0.043 g, 0.2 mmol) and 4-methylpiperidine (0.020 g, 0.2 mmol) were reacted according to GP15 to give the title compound (67KK20c) (0.008 g, 14%). HPLC-MS (ammonium acetate) $[M+H]^+$=277.3.

3.118 3-[3-(4-Butylpiperidin-1-yl)propyl]-3H-benzothiazol-2-one (62KK40d)

3-(3-Chloropropyl)-3H-benzothiazol-2-one (62KK21) (0.046 g, 0.2 mmol) and 4-butylpiperidine (0.028 g, 0.2 mmol) were reacted according to GP15 to give the title compound (62KK40d) (0.042 g, 63%). HPLC-MS (ammonium acetate) $[M+H]^+$=333.1.

3.119 3-[3-(2-Ethylpiperidin-1-yl)propyl]-3H-benzothiazol-2-one (67KK01f)

3-(3-Chloropropyl)-3H-benzothiazol-2-one (62KK21) (0.048 g, 0.21 mmol) and 2-ethylpiperidine (0.022 g, 0.19 mmol) were reacted according to GP15 to give the title compound (67KK01f) (0.015 g, 26%). HPLC-MS (ammonium acetate) $[M+H]^+$=305.1.

3.120 3-[3-(4-Methylpiperidin-1-yl)propyl]-3H-benzothiazol-2-one (67KK01 g)

3-(3-Chloropropyl)-3H-benzothiazol-2-one (62KK21) (0.048 g, 0.21 mmol) and 4-methylpiperidine (0.020 g, 0.20 mmol) were reacted according to GP15 to give the title compound (67KK01 g) (0.024 g, 41%). HPLC-MS (ammonium acetate) $[M+H]^+$=291.0.

3.121 3-[4-(4-Butylpiperidin-1-yl)butyl]-3H-benzothiazol-2-one (62KK40e)

3-(4-Chlorobutyl)-3H-benzothiazol-2-one (62KK29) (0.049 g, 0.20 mmol) and 4-butylpiperidine (0.028 g, 0.20 mmol) were reacted according to GP15 to give the title compound (62KK40e) (0.032 g, 46%). HPLC-MS (ammonium acetate) [M+H]$^+$=347.1.

3.122 3-[4-(2-Ethylpiperidin-1-yl)butyl]-3H-benzothiazol-2-one (67KK04f)

3-(4-Chlorobutyl)-3H-benzothiazol-2-one (62KK29) (0.025 g, 0.10 mmol) and 2-ethylpiperidine (0.011 g, 0.10 mmol) were reacted according to GP15 to give the title compound (67KK04f) (0.015 g, 47%). HPLC-MS (ammonium acetate) [M+H]$^+$=319.1.

3.123 3-[4-(4-Methylpiperidin-1-yl)butyl]-3H-benzothiazol-2-one (67KK40 g)

3-(4-Chlorobutyl)-3H-benzothiazol-2-one (62KK29) (0.025 g, 0.10 mmol) and 4-methylpiperidine (0.010 g, 0.10 mmol) were reacted according to GP15 to give the title compound (67KK04 g) (0.019 g, 62%). HPLC-MS (ammonium acetate) [M+H]$^+$=305.1.

3.124 3-[2-(4-Butylpiperidin-1-yl)ethyl]-3H-benzooxazol-2-one (62KK40f)

3-(2-Chloroethyl)-3H-benzooxazol-2-one (62KK39) (0.039 g, 0.20 mmol) and 4-butylpiperidine (0.028 g, 0.20 mmol) were reacted according to GP15 to give the title compound (62KK40f) (0.014 g, 23%). HPLC-MS (ammonium acetate) [M+H]$^+$=303.1.

3.125 3-[2-(2-Ethylpiperidin-1-yl)ethyl]-3H-benzooxazol-2-one (67KK16-f)

3-(2-Chloroethyl)-3H-benzooxazol-2-one (62KK39) (0.032 g, 0.16 mmol) and 2-ethylpiperidine (0.017 g, 0.15 mmol) were reacted according to GP15 to give the title compound (67KK16-f) (0.006 g, 15%). HPLC-MS (ammonium acetate) [M+H]$^+$=275.4.

3.126 3-[2-(4-Methylpiperidin-1-yl)ethyl]-3H-benzooxazol-2-one (67KK16-g)

3-(2-Chloroethyl)-3H-benzooxazol-2-one (62KK39) (0.032 g, 0.16 mmol) and 4-methylpiperidine (0.015 g, 0.15 mmol) were reacted according to GP15 to give the title compound (67KK16-g) (0.015 g, 38%). HPLC-MS (ammonium acetate) [M+H]$^+$=261.3.

3.127 3-[3-(4-Butylpiperidin-1-yl)propyl]-3H-benzooxazol-2-one (62KK40 g)

3-(3-Chloropropyl)-3H-benzooxazol-2-one (62KK30) (0.042 g, 0.20 mmol) and 4-butylpiperidine (0.028 g, 0.20 mmol) were reacted according to GP15 to give the title compound (62KK40 g) (0.033 g, 52%). HPLC-MS (ammonium acetate) [M+H]$^+$=317.3.

3.128 3-[3-(2-Ethylpiperidin-1-yl)propyl]-3H-benzooxazol-2-one (67KK07-f)

3-(3-Chloropropyl)-3H-benzooxazol-2-one (62KK30) (0.021 g, 0.10 mmol) and 2-ethylpiperidine (0.011 g, 0.10 mmol) were reacted according to GP15 to give the title compound (67KK07-f) (0.013 g, 45%). HPLC-MS (ammonium acetate) [M+H]$^+$=289.1.

3.129 3-[3-(4-Methylpiperidin-1-yl)propyl]-3H-benzooxazol-2-one (67KK07-g)

3-(3-Chloropropyl)-3H-benzooxazol-2-one (62KK30) (0.021 g, 0.10 mmol) and 4-methylpiperidine (0.010 g, 0.10 mmol) were reacted according to GP15 to give the title compound (67KK07-g) (0.016 g, 58%). HPLC-MS (ammonium acetate) [M+H]$^+$=275.1.

3.130 3-[4-(4-Butylpiperidin-1-yl)butyl]-3H-benzooxazol-2-one (62KK40 h)

3-(4-Chlorobutyl)-3H-benzooxazol-2-one (62KK28) (0.045 g, 0.20 mmol) and 4-butylpiperidine (0.028 g, 0.20 mmol) were reacted according to GP15 to give the title compound (62KK40 h) (0.031 g, 47%). HPLC-MS (ammonium acetate) [M+H]$^+$=331.2.

3.131 3-[4-(2-Ethylpiperidin-1-yl)butyl]-3H-benzooxazol-2-one (67KK06-f)

3-(4-Chlorobutyl)-3H-benzooxazol-2-one (62KK28) (0.023 g, 0.10 mmol) and 2-ethylpiperidine (0.011 g, 0.10 mmol) were reacted according to GP15 to give the title compound (67KK06-f) (0.007 g, 23%). HPLC-MS (ammonium acetate) [M+H]$^+$=303.1.

3.132 3-[4-(4-Methylpiperidin-1-yl)butyl]-3H-benzooxazol-2-one (67KK016-g)

3-(4-Chlorobutyl)-3H-benzooxazol-2-one (62KK28) (0.023 g, 0.10 mmol) and 4-methylpiperidine (0.010 g, 0.10 mmol) were reacted according to GP15 to give the title compound (67KK06-g) (0.009 g, 31%). HPLC-MS (ammonium acetate) [M+H]$^+$=289.1.

3.133 General Procedure 16 (GP16)

A 4 ml vial was charged with 3-(3-chloropropyl)-3H-benzooxazol-2-one (1 equiv), 4-butylpiperidine (1.2 equiv), NaI (0.100 g, 0.67 mmol), and K$_2$CO$_3$ (0.075 g, 0.54 mmol) in MeCN (1 ml) and shaken at 50° C. for 20 h. The reaction mixture was cooled to r.t., water added (1 ml), and the product was extracted into EtOAc (2×1 ml). The combined org. layer was added an acidic ion-exchange column. The column was washed with MeOH (2 column volumes) then the product was eluded of the column using 10% ammonium hydroxide in MeOH (2 column volumes) and concentrated in vacuo. The product was purified by flash CC and/or by prep. RP-HPLC [conditions: stationary phase, Luna 15 um C18; column, 250×21.2 mm; mobile phase, 20 ml/min, H$_2$O/MeCN, ammoniumacetate buffer (25 nM)].

3.134 3-[3-(4-butylpiperidin-1-yl]propyl)-4-methyl-3H-benzooxazol-2-one (86KK25a)

3-(3-Chloropropyl)-4-methyl-3H-benzooxazol-2-one (86KK21a) (0.063 g, 0.28 mmol) and 4-butylpiperidine (0.044 g, 0.31 mmol) were reacted according to GP16. Purified by prep. RP-HPLC to give the title compound (86KK25a) (0.039 g, 42%). $^1$H NMR (CD$_3$OD+CDCl$_3$) δ 0.87 (t, J=6.7 Hz, CH$_3$), 1.30-1.08 (m, 9 H), 1.62 (d, J=11.9 Hz, 2 H), 1.97-1.87 (m, 4 H), 2.42 (t. J=7.2 Hz, CH$_2$), 2.55 (s, CH$_3$), 2.86 (d, J=11.7 Hz, 2 H), 4.03 (t J=7.0, CH$_2$), 7.05-6.94 (m, 3 H); $^{13}$C NMR (CD$_3$OD+CDCl$_3$) δ 14.4, 17.6, 23.8, 27.8, 30.0, 33.0, 36.7, 37.2, 43.0, 55.0, 56.8, 108.7, 121.5, 123.4, 128.1, 129.9, 144.1, 156.8; HPLC-MS (ammonium acetate) [M+H]$^+$=331.3 (MH$^+$).

3.135 3-[3-(4-butylpiperidin-1-yl]propyl)-5,7-dimethyl-3H-benzooxazol-2-one (86KK25b)

3-(3-Chloropropyl)-5,7-dimethyl-3H-benzooxazol-2-one (86KK21b) (0.043 g, 0.18 mmol) and 4-butylpiperidine (0.028 g, 0.20 mmol) were reacted according to GP16. Purified by prep. RP-HPLC to give the title compound (86KK25b) (0.032 g, 52%). $^1$H NMR (CD$_3$OD+CDCl$_3$) δ 0.88 (t, J=6.5 Hz, CH$_3$), 1.27-1.11 (m, 9 H), 1.64 (d, J=12,1 Hz, 2 H), 1.98-1.87 (m, 4 H), 2.30 (s, CH$_3$), 2.35 (s, CH$_3$), 2.39-2.35 (m, 2 H), 2.84 (d, J=11.7 Hz, 2 H), 3.84 (t, J=6.7 Hz, CH$_2$), 6.75 (s, 1 H), 6.81 (s, 1 H); $^{13}$C NMR (CD$_3$OD+CDCl$_3$) δ 14.4, 14.4, 21.6, 23.8, 25.6, 29.9, 33.0, 36.6, 37.2, 41.5, 54.9, 56.7, 107.9, 120.8, 125.5, 131.8, 134.9, 140.3, 156.6; HPLC-MS (ammonium acetate) [M+H]$^+$=345.3.

3.136 3-[3-(4-butylpiperidin-1-yl]propyl)-6-methyl-3H-benzooxazol-2-one (86KK25c)

3-(3-chlorpropyl)-6-methyl-3H-benzooxazol-2-one (86KK21 c) (0.052 g, 0.23 mmol) and 4-butylpiperidine (0.035 g, 0.25 mmol) were reacted according to GP16. Purified by prep. RP-HPCL to give the title compound (86KK25c) (0.014 g, 18%). $^1$H NMR (CD$_3$OD+CDCl$_3$) δ 0.88 (t, J=7.0, CH$_3$), 1.29-1.12 (m, 9 H), 1.65 (d, J=11.1 Hz, 2 H), 2.00-1.89 (m, 4 H), 2.38 (s, CH$_3$), 2.41-2.38 (m, 2 H), 2.86 (d, J=11.9 Hz, 2 H), 3.87 (t, J=6.8, CH$_2$), 7.06-7.04 (m, 3 H); $^{13}$C NMR (CD$_3$OD+CDCl$_3$) δ 14.4, 21.4, 23.7, 25.6, 29.9, 32.9, 36.6, 37.1, 41.5, 54.8, 56.7, 109.5, 111.3, 125.4, 129.9, 133.9, 143.9, 156.4; HPLC-MS (ammonium acetate) [M+H]$^+$=331.3.

3.137 3-[3-(4-butylpiperidin-1-yl]propyl)-5-methyl-3H-benzooxazol-2-one (86KK25d)

3-(3-chlorpropyl)-5-methyl-3H-benzooxazol-2-one (86KK21d) (0.032 g, 0.14 mmol) and 4-butylpiperidine (0.021 g, 0.15 mmol) were reacted according to GP16. Purified by prep. RP-HPLC to give the title compound (86KK25d) (0.022 g, 48%). $^1$H NMR (CD$_3$OD+CDCl$_3$) δ 0.89 (t, J=7.0, CH$_3$), 1.29-1.15 (m, 9 H), 1.64 (d, J=10.6, 2 H), 1.98-1.67 (m, 4 H), 2.37-2.41 (m, 2 H), 2.39 (s, CH$_3$), 2.86 (d, J=11.9 Hz, 2 H), 3.87 (t, J=6.9, CH$_2$), 6.92-7.09 (m, 3 H); $^{13}$C NMR (CD$_3$OD+CDCl$_3$) δ 14.4, 21.6, 23.8, 25.7, 29.9, 33.0, 36.6, 37.2, 41.4, 54.9, 56.6, 110.3, 110.4, 123.9, 132.3, 135.2, 141.9, 156.6; HPLC-MS (ammonium acetate) [M+H]$^+$=331.3.

3.138 5-t-Butyl-3-[3-(4-butylpiperidin-1-yl)propyl]-3H-benzooxazol-2-one (86KK25e)

5-t-butyl-3-(3-chloropropyl)-3H-benzooxazol-2-one (86KK21e) (0.056 g, 0.21 mmol) and 4-butylpiperidine (0.032 g, 0.23 mmol) were reacted according to GP16. Purified by prep. RP-HPLC to give the title compound (86KK25e) (0.103 g, 50%). $^1$H NMR (CD$_3$OD+CDCl$_3$) δ 0.88 (t, J=6.6 Hz, CH$_3$), 1.34-1.11 (m, 18 H), 1.63 (d, J=11.3 Hz, 2 H), 1.88-1.99 (m, 4 H), 2.41 (t, J=7.2 Hz, CH$_2$), 2.86 (d, J=11.9 Hz, 2 H), 3.91 (t, J=6.8 Hz, CH$_2$), 7.19-7.11 (m, 3 H); $^{13}$C NMR (CD$_3$OD+CDCl$_3$) δ 14.4, 23.7, 25.7, 29.9, 32.0, 33.0, 35.7, 36.6, 37.1, 41.4, 54.9, 56.8, 107.0, 110.0, 120.4, 132.0, 141.7, 148.9, 156.7; HPLC-MS (ammonium acetate) [M+H]$^+$=373.3.

3.139 3-[3-(4-butylpiperidin-1-yl)propyl]-6-chloro-3H-benzooxazol-2-one (86KK25f)

3-(3-chloropropyl)-6-chloro-3H-benzooxazol-2-one (86KK21f) (0.138 g, 0.56 mmol) and 4-butylpiperidine (0.088 g, 0.62 mmol) were reacted according to GP16. Purified by prep. RP-HPLC to give the title compound (86KK25f) (0.103 g, 53%). $^1$H NMR (CD$_3$OD) δ 0.89 (t, J=6.9, CH$_3$), 1.31-1.08 (m, 9 H), 1.62 (d, J=11.9, 2 H), 1.84-1.98 (m, 4 H), 2.38 (t, J=7.0 Hz, CH$_2$), 2.83 (d, J=11.9 Hz, 2 H), 3.89 (t, J=6.7 Hz, CH$_2$), 7.28-7.17 (m, 3 H); $^{13}$C NMR (CD$_3$OD) δ 14.4, 23.9, 25.6, 30.1, 33.1, 36.8, 37.4, 41.9, 55.0, 56.8, 110.9, 111.5, 125.1, 128.7, 131.6, 144.3, 155.9; HPLC-MS (ammonium acetate) [M+H]$^+$=351.2.

3.140 3-[3-(4-butylpiperidin-1-yl)propyl]-5-methoxy-3H-benzooxazol-2-one (86KK22i)

3-(3-chloropropyl)-5-methoxy-3H-benzooxazol-2-one (86KK21i) (0.041 g, 0.17 mmol) and 4-butylpiperidine (0.027 g, 0.19 mmol) were reacted according to GP16. Purified by prep. RP-HPLC to give the title compound (86KK22i) (0.103 g, 36%). $^1$H NMR (CD$_3$OD+CDCl$_3$) δ 0.88 (t, J=6.9 Hz, CH$_3$), 1.28-1.13 (m, 9 H), 1.65 (d, J=12.1 Hz, 2 H), 1.98-1.89 (m, 4 H), 2.39 (t, J=7.2 Hz, CH$_2$), 2.86 (d, J=11.9 Hz, 2 H), 3.81 (s, OCH$_3$), 3.86 (t, J=6.9 Hz, CH$_2$), 6.67-6.65 (m, 1 H), 6.77-6.76 (m, 1 H), 7.11-7.09 (m, 1 H); $^{13}$C NMR (CD$_3$OD+CDCl$_3$) δ 14.3, 23.7, 25.6, 29.8, 32.9, 36.5, 37.1, 41.4, 54.8, 56.4, 56.6, 96.9, 108.1, 110.9, 132.9, 137.7, 156.8, 158.1; HPLC-MS (ammonium acetate) [M+H]$^+$=347.1.

3.141 3-[3-(4-butylpiperidin-1-yl)propyl]-5-fluoro-3H-benzooxazol-2-one (86KK22k)

3-(3-chloropropyl)-5-fluoro-3H-benzooxazol-2-one (86KK21k) (0.039 g, 0.17 mmol) and 4-butylpiperidine (0.027 g, 0.19 mmol) were reacted according to GP16. Purified by prep. RP-HPLC to give the title compound (86KK22k) (0.032 g, 56%). $^1$H NMR (CD$_3$OD) δ 0.89 (t, J=7.0 Hz, CH$_3$), 1.29-1.09 (m, 9H), 1.64 (, J=11.9 Hz, 2 H), 1.99-1.86 (m, 4 H), 2.38 (t, J=7.0 Hz, CH$_2$), 2.84 (d, J=11.7 Hz, CH$_2$), 3.89 (t, J=6.8 Hz, CH$_2$), 6.88-6.83 (m, 1 H), 7.22-7.09 (m, 2 H); $^{13}$C NMR (CD$_3$OD) δ 14.4, 23.9, 25.5, 30.1, 33.2, 36.8, 37.4, 41.9, 55.0, 56.8, 98.6 (J=30.3 Hz), 109.4 (J=25.2 Hz), 111.4 (J=9.7 Hz), 133.7 (J=13.2 Hz), 140.0 (J=2.3 Hz), 156.7, 161.1 (J=240.0 Hz); HPLC-MS (ammonium acetate) [M+H]$^+$=335.1

3.142 3-[3-(4-butylpiperidin-1-yl)propyl]-6-fluoro-3H-benzooxazol-2-one (97KK28)

3-(3-chloropropyl)-6-fluoro-3H-benzooxazol-2-one (86KK21j) (0.090 g, 0.39 mmol) and 4-butylpiperidine (0.070 g, 0.50 mmol) were reacted according to GP16. Purified by flash CC (SiO$_2$; DCM/MeOH 20:1) and prep. RP-HPLC to give the title compound (97KK28) (0.065 g, 50%). $^1$H NMR (CD$_3$OD) δ 0.89 (t, J=7.0, CH$_3$), 1.29-1.09 (m, 9 H), 1.64 (d, J=11.7, CH$_2$), 1.99-1.86 (m, 4 H), 2.38 (t, J=7.0 Hz, CH$_2$), 2.84 (d, J=11.9 Hz, 2 H), 3.90 (t, J=6.9 Hz, CH$_2$), 7.02-6.96 (m, 1 H), 7.21-7.10 (m, 2 H); $_{13}$C CD$_3$OD) δ 14.4, 23.9, 25.6, 30.1, 33.2, 36.8, 37.4, 41.8, 55.0, 56.9, 99.9 (J=29.4 Hz), 110.4 (J=9.4 Hz), 111.4 (J=24.2 Hz), 129.0 (J=1.9 Hz), 144.1 (J=13.6 Hz), 156.4, 160.2 (J=240.0 Hz); HPLC-MS (ammonium acetate) [M+H]$^+$=335.3

3.143 General Procedure 17 (GP17)

A 4 ml vial was charged with 3-(3-bromopropyl)-3H-benzooxazol-2-one (1 equiv), 4-butylpiperidine (1.4 equiv), and K$_2$CO$_3$ (0.075 g, 0.54 mmol) in MeCN (1 ml) and shaken at 60° C. for 20 h. The reaction mixture was cooled to r.t., water was added (1 ml), and the product extracted into ethyl acetate (2×1 ml). The combined org. layer was added an acidic ion-exchange column. The column was washed with MeOH (2 column volumes) then the product was eluded of the column using 10% ammonium hydroxide in MeOH (2 column volumes). The product was purified by flash CC and/or by prep. RP-HPLC [conditions: stationary phase, Luna 15 um C18; column, 250×21.2 mm; mobile phase, 20 ml/min, H$_2$O/MeCN, ammoniumacetate buffer (25 nM)].

3.144 3-[3-(4-butylpiperidin-1-yl)propyl]-6-methoxy-3H-benzooxazol-2-one (97KK02a)

3-(3-Bromopropyl)-6-methoxy-3H-benzooxazol-2-one (97KK01a) (0.093 g, 0.56 mmol) and 4-butylpiperidine (0.086 g, 0.61 mmol) were reacted according to GP17. Purified by prep. RP-HPLC to give the title compound (97KK02a) (0.114 g, 71%). $^1$H NMR (CD$_3$OD) δ 0.89 (t, J=6.1 Hz, CH$_3$), 1.27-1.12 (m, 9 H), 1.64 (d, J=11.7 Hz, 2 H), 1.99-1.88 (m, 4 H), 2.39 (t, J=7.2 Hz, CH$_2$), 2.86 (d, J=11.5 Hz, 2 H), 3.78 (s, OCH$_3$), 3.86 (t, J=6.6 Hz, CH$_2$), 7.10-6.78 (m, 3 H); $^{13}$C NMR (CD$_3$OD) δ 14.4, 23.9, 25.7, 30.1, 33.1, 36.8, 37.4, 41.6, 55.0, 56.5, 56.9, 98.3, 126.0, 144.7, 156.7, 157.8; HPLC-MS (ammonium acetate) [M+H]$^+$=347.3.

3.145 3-[3-(4-butylpiperidin-1-yl)propyl]-5,7-dibromo-3H-benzooxazol-2-one (97KK02b)

3-(3-Bromopropyl)-5,7-dibromo-3H-benzooxazol-2-one (97KK02b) (0.138 g, 0.47 mmol) and 4-butylpiperidine (0.069 g, 0.49 mmol) were reacted according to GP17. Purified by prep. RP-HPLC to give the title compound (97KK02b) (0.152 g, 78%). $^1$H NMR (CD$_3$OD+CDCl$_3$) δ 0.80 (t, J=6.6 Hz, CH$_3$), 1.18-1.06 (m, 9 H), 1.61 (d, J=12.1 Hz, 2 H), 1.95-1.89 (m, 4H), 2.38 (t, J=6.6 Hz, CH$_2$), 2.81 (d, J=11.7 Hz, 2H), 3.81 (t, J=6.6 Hz, CH$_2$), 7.34-7.28 (m, 2 H); $^{13}$C NMR (CD$_3$OD+CDCl$_3$) δ 14.3, 23.4, 24.8, 29.6, 32.4, 36.0, 36.7, 41.7, 54.4, 55.8, 103.5, 112.1, 117.6, 128.4, 134.0, 140.7, 154.5; HPLC-MS (ammonium acetate) [M+H]$^+$=473.0.

3.146 3-[3-(4-butylpiperidin-1-yl)propyl]-7-methyl-3H-benzooxazol-2-one (97KK06a)

Crude 3-(3-bromopropyl)-7-methyl-3H-benzooxazol-2-one (97KK03a) (0.074 g) and 4-butylpiperidine (0.052 g, 0.37 mmol) were reacted according to GP17. Purified by prep. RP-HPLC to give the title compound (97KK06a) (0.056 g). $^1$H NMR (CD$_3$OD+CDCl$_3$) δ 0.87 (t, J=6.1 Hz, CH$_3$), 1.26-1.17 (m, 9 H), 1.68 (d, J=12.1 Hz, 2 H), 2.10-1.97 (m, 4 H), 2.34 (s, CH$_3$), 2.53 (t, J=7.4 Hz, CH$_2$), 2.96 (d, J=11.3 Hz, 2 H), 3.88 (t, J=6.8 Hz), 6.97-6.93 (m, 2 H), 7.11-7.08 (m, 1 H); $^{13}$C NMR (CD$_3$OD+CDCl$_3$) δ 14.3, 14.4, 23.6, 23.8, 25.1, 29.7, 32.2, 36.0, 36.8, 41.2, 54.5, 56.2, 107.1, 121.2, 124.7, 125.0, 131.6, 142.1, 156.1; HPLC-MS (ammonium acetate) [M+H]$^+$=331.3.

3.147 3-[3-(4-butylpiperidin-1-yl)propyl]-7-isopropyl-3H-benzooxazol-2-one (97KK06b)

Crude 3-(3-bromopropyl)-7-isopropyl-3H-benzooxazol-2-one (97KK03b) (0.059 g) and 4-butylpiperidine (0.039 g, 0.28 mmol) were reacted according to GP17. Purified by prep. RP-HPLC. Purified by prep. RP-HPLC to give the title compound (97KK06b) (0.044 g). $^1$H NMR (CD$_3$OD) δ 0.88 (t, J=6.3 Hz, CH$_3$), 1.32-1.07 (m, 15 H), 1.61 (d, J=12.1 Hz, 2 H), 1.99-1.84 (m, 4 H), 2.39 (t, J=7.0 Hz, CH$_2$), 2.83 (d, J=11.3 Hz, 2 H), 3.19 (sept, J=6.8 Hz, CH), 3.89 (t, J=6.7 Hz, CH$_2$), 7.03-7.00 (m, 2 H), 7.17-7.13 (M, 1 H); $^{13}$C NMR (CD$_3$OD) δ 14.4, 22.8, 23.9, 25.7, 29.9, 30.1, 33.2, 36.9, 37.4, 41.8, 55.0, 57.0, 107.7, 121.3, 125.2, 132.3, 132.3, 141.4, 156.5; HPLC-MS (ammonium acetate) [M+H]$^+$= 359.3.

3.148 3-[3-(4-butylpiperidin-1-yl)propyl]-5,7-diisopropyl-3H-benzooxazol-2-one (97KK07a)

Crude 3-(3-bromopropyl)-5,7-diisopropyl-3H-benzooxazol-2-one (97KK03c) (0.077 g) and 4-butylpiperidine (0.040 g, 0.28 mmol) were reacted according to GP17. Purified by prep. RP-HPLC to give the title compound (97KK07a) (0.056 g). $^1$H NMR (CD$_3$OD) δ 0.88 (m, CH$_3$), 1.32-1.16 (m, 21 H), 1.69 (d, J=12.1 Hz, 2 H), 2.17-2.01 (m, 4 H), 2.60 (t, J=7.2 Hz, CH$_2$), 3.03-2.92 (m, 3 H), 3.15 (sept, J=6.9 Hz, CH), 3.90 (t, J=6.7 Hz, CH$_2$), 6.88 (s, 1 H), 6.92 (s, 1 H); $^{13}$C NMR (CD$_3$OD) δ 14.4, 22.8, 23.9, 24.8, 25.3, 30.0, 30.3, 32.5, 35.8, 36.3, 37.1, 41.3, 54.7, 56.5, 105.6, 119.5, 132.0, 132.3, 139.7, 146.9, 156.8; HPLC-MS (ammonium acetate) [M+H]$^+$=401.4.

3.149 3-[3-(4-butylpiperidin-1-yl)propyl]-4,6-dimethoxy-3H-benzooxazol-2-one (97KK07c)

3-(3-Bromopropyl)-4,6-dimethoxy-3H-benzooxazol-2-one (97KK05b) (0.033 g, 0.10 mmol) and 4-butylpiperidine (0.024 g, 0.17 mmol) were reacted according to GP17. Purified by prep. RP-HPLC to give the title compound (97KK07c) (0.023 g, 61%). $^1$H NMR (CD$_3$OD) δ 0.89 (m, CH$_3$), 1.27-1.13 (m, 9 H), 1.66 (d, J=11.9 Hz, 2 H), 2.03-1.95 (m, 4 H), 2.47 (t, J=6.8 Hz, CH$_2$), 2.94 (d, J=10.6 Hz, 2 H), 3.78 (s, OCH$_3$), 3.90 (s, OCH$_3$), 3.96 (t, J=6.8 Hz, CH$_2$), 6.54-6.46 (m, 2 H); $^{13}$C NMR (CD$_3$OD) δ 14.4, 23.8, 24.1, 29.9, 30.2, 35.0, 36.3, 53.8, 53.9, 54.1, 56.5, 115.3, 125.0, 129.6, 130.6, 131.1, 159.3, 161.1; HPLC-MS (ammonium acetate) [M+H]$^+$=377.3.

3.150 3-[3-(4-Butylpiperidin-1-yl)propyl]7-fluoro-3H-benzooxazol-2-one (97KK13)

3-(3-bromopropyl)-7-fluoro-3H-benzooxazol-2-one (97KK12a) (0.100 g, 0.36 mmol) and 4-butylpiperidine (0.095 g, 0.67 mmol) were reacted according to GP17. Purified by flash CC (SiO$_2$; DCM/MeOH 10:1) and prep. RP-HPLC to give the title compound (97KK13) (0.078 g, 65%). $^1$H NMR (CD$_3$OD) δ 0.88 (t, J=6.9 Hz, CH$_3$), 1.29-1.07 (m, 9 H), 1.61 (d, J=11.9 Hz, 2 H), 1.99-1.84 (m, 4 H), 2.39 (t, J=7.0 Hz, CH$_2$), 2.83 (d, J=11.7 Hz, 2 H), 3.91 (t, J=6.8 Hz, CH$_2$), 6.97-6.92 (m, 1 H), 7.06-7.03 (m, 1 H), 7.22-7.17 (m, 1 H); $^{13}$C NMR (CD$_3$OD) δ 14.4, 23.9, 25.5, 30.0, 33.1, 36.8, 37.4, 42.3, 55.0, 56.9, 106.3 (J=3.9 Hz), 111.0 (J=17.1 Hz), 125.8 (J=6.8 Hz), 130.7 (J=14.2 Hz), 135.3 (J=4.8 Hz), 147.1 (J=247.4), 155.6; HPLC-MS (ammonium acetate) [M+H]$^+$=335.3.

3.151 3-[3-(4-Butylpiperidin-1-yl)propyl]-5,7-dichloro-6-methyl-3H-benzooxazol-2-one (97KK16)

Crude 3-(3-bromopropyl)-5,7-dichloro-6-methyl-3H-benzooxazol-2-one (97KK12b) (0.051 g) and 4-butylpiperidine (0.041 g, 0.29 mmol) were reacted according to GP17. Purified by prep. RP-HPLC to give the title compound (97KK16) (0.016 g). $^1$H NMR (CD$_3$OD+CDCl$_3$) δ 0.88 (t, J=6.6 Hz, CH$_3$), 1.29-1.07 (m, 9 H), 1.63 (d, J=12.1 Hz, 2 H), 1.97-1.87 (m, 4 H), 2.38 (t, J=7.2 Hz, CH$_2$), 2.44 (s, CH$_3$), 2.83 (d, J=11.7 Hz, 2 H), 3.87 (t, J=6.7 Hz, CH$_2$), 7.27 (s, 1 H); $^{13}$C NMR (CD$_3$OD+CDCl$_3$) δ 14.4, 16.7, 23.8, 25.2, 29.9, 32.9, 36.5, 37.2, 42.0, 54.8, 56.4, 109.5, 117.0, 129.0, 130.8, 131.7, 139.5, 155.2; HPLC-MS (ammonium acetate) [M+H]$^+$=399.2.

3.152 General Procedure 18 (GP18)

A 4 ml vial was charged with 3H-benzooxazol-2-one (1 equiv), 3-(4-butylpiperidin-1-yl)propan-1-ol (1.2 equiv), diethyl azodicarboxylate (1.2 equiv), and triphenylphosphine (1.2 equiv) in THF (4 ml) and shaken at r.t. for 20 h. The reaction mixture was added water (1 ml), and the product extracted into EtOAc (2×1 ml). The combined org. layer was added an acidic ion-exchange column. The column was washed with MeOH (2 column volumes) then the product was eluded of the column using 10% ammonium hydroxide in MeOH (2 column volumes). The product was purified by flash CC and/or by prep. RP-HPLC [conditions: stationary phase, Luna 15 um C18; column, 250×21.2 mm; mobile phase, 20 ml/min, H$_2$O/MeCN, ammoniumacetate buffer (25 nM)].

3.153 3-(4-Butylpiperidin-1-yl)propan-1-ol (92LH52)

A vial was charged with 4-butylpiperidine (0.706 g, 5.0 mmol), 3-bromopropan-1-ol (0.694 g, 5.0 mmol), and K$_2$CO$_3$ (0.967 g, 7.0 mmol) in MeCN (4 ml) and was shaken at 50° for 72 h. The reaction mixture was added water and the product was extracted into EtOAc. The combined org. layer was dried over Na$_2$SO$_4$ and concentrated in vacuo. The material was used for the next reaction step without further purification.

3.154 3-[3-(4-butylpiperidin-1-yl)propyl]-5,7-dichloro-6-ethyl-3H-benzooxazol-2-one (97KK14)

5,7-Dichloro-6-ethyl-3H-benzooxazol-2-one (97KK10) (0.257 g, 1.11 mmol), 3-(4-butylpiperidin-1yl)propan-1-ol (0.272 g, 1.36 mmol), diethyl azodicarboxylate (0.232 g, 1.33 mmol), and PPh$_3$ (0.355 g, 1.35 mmol) in THF (4 ml) were reacted according to GP18. Purified by flash CC (SiO$_2$; DCM/MeOH 20:1) and prep. RP-HPLC to give the title compound (97KK14) (0.058 g, 13%). $^1$H NMR (CD$_3$OD+ CDCl$_3$) δ 0.87 (t, J=6.6 Hz, CH$_3$), 1.28-1.04 (m, 12 H), 1.61 (d, J=11.9 Hz, 2 H), 1.95-1.85 (m, 4 H), 2.38 (t, J=7.0 Hz, CH$_2$), 2.81 (d, J=11.7 Hz, 2 H), 2.93 (q, J=7.4 Hz, CH$_2$), 3.87 (t, J=6.6 Hz, CH$_2$), 7.23 (s, 1 H); $^{13}$C NMR (CD$_3$OD+ CDCl$_3$) δ 13.2, 14.4, 23.6, 24.8, 25.1, 29.8, 32.8, 36.4, 37.1, 42.0, 54.7, 56.3, 109.6, 116.6, 130.2, 131.6, 134.5, 139.4, 155.1.

3.155   5-Bromo-3-[3-(4-butylpiperidin-1-yl)propyl]-7-fluoro-3H-benzooxazol-2-one (97KK15-a)

5-Bromo-7-fluoro-3H-benzooxazol-2-one (97KK09b) (0.049 g, 0.21 mmol), 3-(4-butylpiperidin-1yl)propan-1-ol (0.066 g, 0.33 mmol), diethyl azodicarboxylate (0.044 g, 0.25 mmol), and PPh$_3$ (0.071 g, 0.27 mmol) in THF (2 ml) were reacted according to GP18. Purified by flash CC (SiO$_2$; DCM/MeOH 20:1) and prep. RP-HPLC to give the title compound (97KK15-a) (0.019 g, 22%). $^1$H NMR (CD$_3$OD+ CDCl$_3$) δ 0.80 (t, J=6.8 Hz, CH$_3$), 1.23-1.04 (m, 9 H), 1.58 (d J=13.3 Hz, 2 H), 1.90-1.81 (m, 4H), 2.30 (t, J=7.0 Hz, CH$_2$), 2.76 (d, J=11.7 Hz, 2 H), 3.81 (t, J=6.7 Hz, CH$_2$), 7.20-7.06 (m, 2 H); HPCL-MS (ammonium acetate) [M+H]$^+$=413.2.

3.156   3-[3-(Butylpiperidin-1-yl)propyl]-6,7-difluoro-3H-benzooxazol-2-one (97KK15-b)

6,7-Difluoro-3H-benzooxazol-2-one (97KK11) (0.136 g, 0.79 mmol), 3-(4-butylpiperidin-1yl)propan-1-ol (0.196 g, 0.98 mmol), diethyl azodicarboxylate (0.165 g, 0.95 mmol), and PPh$_3$ (0.389 g, 1.48 mmol) in THF (2 ml) was reacted according to GP18. Purified by flash CC (SiO$_2$; DCM/MeOH 20:1) and prep. RP-HPLC to give the title compound (97KK15-b) (0.063 g, 23%). $^1$H NMR (CD$_3$OD) δ 0.89 (m, CH$_3$), 1.31-1.05 (m, 9 H), 1.64 (d, J=12.5 Hz, 2 H), 2.00-1.87 (m, 4 H), 2.42 (t, J=7.2, CH$_2$), 2.86 (d, J=11.7 Hz, 2 H), 3.91 (t, J=6.6 Hz, CH$_2$), 7.03-6.99 (m, 1 H), 7.17-7.10 (m, 1 H); $^{13}$C NMR (CD$_3$OD) δ 14.4, 23.9, 25.3, 30.0, 33.0, 36.7, 37.3, 42.2, 55.0, 56.8, 105.0 (J=4.6 Hz, J=7.7 Hz), 112.7 (J=20.4 Hz), 130.7, 131.8 (J=4.6 Hz, J=10.8 Hz), 136.8 (J=18.5 Hz, J=251.4 Hz), 148.3 (J=10.0, J=240.6 Hz), 155.6; HPLC-MS (ammonium acetate) [M+H]$^+$=353.3.

3.157 3-[3-(Butylpiperidin-1-yl)propyl]-4,5,7-trichloro-3H-benzooxazol-2-one (97KK29)

4,5,7-Trichloro-3H-benzooxazol-2-one (97KK26) (0.342 g, 1.43 mmol), 3-(4-butylpiperidin-1yl)propan-1-ol (0.280 g, 1.40 mmol), diethyl azodicarboxylate (0.299 g, 1.72 mmol), and PPh$_3$ (0.516 g, 1.97 mmol) in THF (5 ml) was reacted according to GP18. Purified by flash CC (SiO$_2$; DCM/MeOH 20:1) and prep. RP-HPLC to give the title compound (97KK29) (0.085 g, 14%). $^1$H NMR (CD$_3$OD+ CDCl$_3$) δ 0.88 (t, J=6.7 Hz, CH$_3$), 1.29-0.90 (m, 9 H), 1.65 (d, J=13.5 Hz, 2 H), 2.11-1.89 (m, 4 H), 2.62 (t, J=7.0 Hz, CH$_2$), 2.96 (d, J=11.9 Hz, 2 H), 4.23 (t, J=6.8 Hz, CH$_2$), 7.40 (s, 1 H); $^{13}$C NMR (CD$_3$OD+CDCl$_3$) δ 14.3, 23.8, 26.8, 29.8, 32.4, 36.1, 37.0, 43.4, 54.7, 56.5, 113.6, 115.4, 124.4, 130.1, 131.3, 140.0, 155.1; HPLC-MS (ammonium acetate) [M+H]$^+$=419.1.

3.158   3-[3-(4-butylpiperidin-1-yl)propyl]-4-methoxy-3H-benzooxazol-2-one (92LH60-1A)

A 4 ml vial was charged with 4-methoxy-3H-benzooxazol-2-one (92LH58) (0.345 g, 0.73 mmol), 3-(4-butylpiperidin-1-yl)propan-1-ol (0.175 g, 0.88 mmol), diethyl azodicarboxylate (0.152 g, 0.88 mmol), and triphenylphosphine (0.230 g, 0.88 mmol) in THF (4 ml) and shaken at r.t. for 20 h. The reaction mixture was added was added an acidic ion-exchange column. The column was washed with MeOH (2 column volumes) then the product was eluded of the column using 10% ammonium hydroxide in MeOH (2 column volumes). The product was purified by flash CC (SiO$_2$; EtOAc) and by prep. RP-HPLC [conditions: stationary phase, Luna 15 um C18; column, 250×21.2 mm; mobile phase, 20 ml/min, H$_2$O/MeCN, ammoniumacetate buffer (25 nM)] to give the title compound (92LH60-1A) (0.135 g, 53%). $^1$H NMR (CD$_3$OD) δ 0.88 (t J=6.8 Hz, CH$_3$), 1.28-1.06 (m, 9 H), 160 (d, J=10.9 Hz, 2 H), 1.99-1.82 (m, 4 H), 2.38 (t, J=7.0 Hz, CH$_2$), 2.84 (d, J=11.9 Hz, 2 H), 3.92 (s, OCH$_3$), 3.98 (t, J=6.8 Hz, CH$_2$), 6.86-6.81 (m, 2 H), 7.07-7.03 (m, 1 H);$^{13}$C NMR (CD$_3$OD) δ 13.2, 23.7, 27.2, 29.8, 32.9, 36.6, 37.1, 43.5, 54.8, 56.5, 56.8, 103.8, 108.3, 120.1, 123.8, 144.6, 146.3, 156.0; HPLC-MS (ammonium acetate) [M+H]$^+$=347.

3.159   3-[3-(4-butylpiperidin-1-yl)propyl]-7-nitro-3H-benzooxazol-2-one (92LH60-2A)

A 4 ml vial was charged with 7-nitro-3H-benzooxazol-2-one (92LH59) (0.090 g, 0.5 mmol), 3-(4-butylpiperidin-1-yl)propan-1-ol (0.120 g, 0.60 mmol), diethyl azodicarboxylate (0.153 g, 0.60 mmol), and triphenylphosphine (0.230 g, 0.60 mmol) in THF (4 ml) and shaken at r.t. for 20 h. The reaction mixture was added was added an acidic ion-exchange column. The column was washed with MeOH (2 column volumes) then the product was eluded of the column using 10% ammonium hydroxide in MeOH (2 column volumes). The product was purified by flash CC (SiO$_2$; EtOAc) and by prep. RP-HPLC [conditions: stationary phase, Luna 15 um C18; column, 250×21.2 mm; mobile phase, 20 ml/min, H$_2$O/MeCN, ammoniumacetate buffer (25 nM)] to give the title compound (92LH60-2A (0.067 g, 37%). $^1$H NMR (CD$_3$OD) δ 0.88 (t, J=6.6 Hz, CH$_3$), 1.60-0.98 (m, 9 H), 1.81 (d, J=12.7 Hz, 2 H), 2.01-1.84 (m, 4 H), 2.41 (t, J=7.0 Hz, CH$_2$), 2.80 (d, J=11.7 Hz, 2 H), 4.00 (t, J=6.8 Hz, CH$_2$), 7.42-7.38 (m, 1 H), 7.62-7.59 (m, 1 H), 7.90-7.88 (m, 1 H); HPLC-MS (ammonium acetate) [M+H]$^+$=362.

3.160   3-[3-(4-butylpiperidin-1-yl)propyl]-5,7-diiodo-3H-benzooxazol-2-one (92LH66)

A 4 ml vial was charged with 5,7-diiodo-3H-benzooxazol-2-one (92LH49) (0.166 g, 0.40 mmol), 3-(4-butylpiperidin-1-yl)propan-1-ol (0.096 g, 0.48 mmol), diethyl azodicarboxylate (0.084 g, 0.48 mmol), and triphenylphosphine (0.126 g, 0.48 mmol) in THF (4 ml) and shaken at r.t. for 20 h. The reaction mixture was added was added an acidic ion-exchange column. The column was washed with MeOH (2 column volumes) then the product was eluded of the column using 10% ammonium hydroxide in MeOH (2 column volumes). The product was purified prep. RP-HPLC [conditions: stationary phase, Luna 15 um C18; column, 250×21.2 mm; mobile phase, 20 ml/min, H$_2$O/MeCN, ammoniumacetate buffer (25 nM)] to give the title compound (92LH66) (0.068 g, 30%). $^1$H NMR (CD$_3$OD) δ 0.80 (t, J=7.0 Hz, CH$_3$), 1.20-1.12 (m, 9 H), 1.53 (d, J=13.1 Hz, 2 H), 1.91-1.80 (m, 4 H), 2.33 (t, J=7.0 Hz, CH$_2$), 2.76 (d, J=11.7 Hz, 2 H), 3.78 (t, J=6.5 Hz, CH$_2$), 7.68-7.47 (m, 2 H); $^{13}$C NMR (CD$_3$OD) δ 14.4, 23.9, 25.0, 30.1, 33.1, 36.7, 37.4, 42.2, 55.0, 56.6, 74.6, 87.8, 118.9, 133.9, 139.6, 145.6, 154.7; HPLC-MS (ammonium acetate) [M+H]$^+$=569.

3.161   3-[3-(4-butylpiperidin-1-yl)propyl]-4-methyl-7-isopropyl-3H-benzooxazol-2-one (92LH75)

A 4 ml vial was charged with 4-methyl-7-isopropyl-3H-benzooxazol-2-one (92LH71) (0.100 g, 0.52 mmol), 3-(4- butylpiperidin-1-yl)propan-1-ol (0.124 g, 0.62 mmol), diethyl azodicarboxylate (0.109 g, 0.62 mmol), and triphenylphosphine (0.164 g, 0.62 mmol) in THF (4 ml) and shaken at r.t. for 20 h. The reaction mixture was added was added an acidic ion-exchange column. The column was washed with MeOH (2 column volumes) then the product was eluded of the column using 10% ammonium hydroxide in MeOH (2 column volumes). The product was purified by prep. RP-HPLC [conditions: stationary phase, Luna 15 um C18; column, 250×21.2 mm; mobile phase, 20 ml/min, H$_2$O/MeCN, ammoniumacetate buffer (25 nM)] to give the title compound (92LH75) (0.100 g, 52%). $^1$H NMR (CD$_3$OD) δ 0.90 (m, CH$_3$), 1.33-1.21 (m, 15 H), 1.76 (d, J=13.5 Hz, 2 H), 2.08 (quint, 7.8 Hz, CH$_2$), 2.40-2.34 (m, 2 H), 2.53 (s, CH$_3$), 2.82-2.78 (m, 2 H), 3.19-3.14 (m, 3 H), 4.08 (t, J=6.9 Hz, CH$_2$), 6.94-6.90 (m, 2 H); $^{13}$C NMR (CD$_3$OD) δ 14.4, 17.4, 22.7, 23.8, 27.0, 29.4, 29.9, 31.9, 35.8, 36.9, 42.4, 54.5, 56.1, 119.0, 121.1, 128.2, 129.6, 130.0, 141.6, 157.0; HPLC-MS (ammonium acetate) [M+H]$^+$=373.

3.162 3-[3-(4-butylpiperidin-1-yl)propyl]-7-methyl-4-isopropyl-3H-benzooxazol-2-one (92LH77)

A 4 ml vial was charged with 7-methyl-4-isopropyl-3H-benzooxazol-2-one (92LH76) (0.066 g, 0.35 mmol), 3-(4-butylpiperidin-1-yl)propan-1-ol (0.084 g, 0.42 mmol), diethyl azodicarboxylate (0.073 g, 0.42 mmol), and triphenylphosphine (0.110 g, 0.42 mmol) in THF (4 ml) and shaken at r.t. for 20 h. The reaction mixture was added was added an acidic ion-exchange column. The column was washed with MeOH (2 column volumes) then the product was eluded of the column using 10% ammonium hydroxide in MeOH (2 column volumes). The product was purified by prep. RP-HPLC [conditions: stationary phase, Luna 15 um C18; column, 250×21.2 mm; mobile phase, 20 ml/min, H$_2$O/MeCN, ammoniumacetate buffer (25 nM)] to give the title compound (92LH77) (0.035 g, 27%). $^1$H NMR (CD$_3$OD) δ 0.90 (t, J=6.3 Hz, CH$_3$), 1.33-1.13 (m, 15 H), 1.68 (d, J=12.7 Hz, 2 H), 2.11-1.94 (m, 4 H), 2.30 (s, CH$_3$), 2.58 (t, J=7.2 Hz, CH$_2$), 2.98 (d, J=11.5 Hz, 2 H), 3.36-3.31 (m, 1 H), 4.07 (t, J=7.0 Hz, CH$_2$), 7.10-6.93 (m, 2 H); $^{13}$C NMR (CD$_3$OD) δ 14.2, 14.4, 23.9, 24.4, 26.9, 28.1, 30.0, 32.7, 36.4, 37.2, 43.5, 55.0, 56.7, 118.8, 122.4, 125.5, 127.8, 130.6, 142.6, 157.3; HPLC-MS (ammonium acetate) [M+H]$^+$=373.

3.163 General Procedure 19 (GP19)

A 4 ml vial was charged with 3-chloroalkyl-3H-benzothiazol-2-one (1 equiv), piperidine (1 equiv), KI (1.3 equiv), and K$_2$CO$_3$ (1.3 equiv) in MeCN (2 ml) and shaken at 50° C. for 48 h. The reaction mixture was added water, the product extracted into EtOAc, and the combined org. layer was concentrated. The product was purified by flash CC (SiO$_2$; EtOAC, MeOH/EtOAc 1:4).

3.164 3-[5-(4-Butylpiperidin-1-yl)pentyl]-3H-benzothiazol-2-one (107LH03-1)

3-(5-Chloropentyl)-3H-benzothiazol-2-one (107LH01) (0.203 g, 0.9 mmol), 4-butylpiperidine (0.127 g, 0.9 mmol), KI (0.200 g, 1.2 mmol), and K$_2$CO$_3$ (0.166 g, 1.2 mmol) in MeCN (2 ml) were reacted according to GP19. Purified by flash CC (SiO$_2$; EtOAc, MeOH/EtOAc 1:4) to give the title compound (107LH03-1) (0.173 g, 53%). $^1$H NMR (CD$_3$OD) δ 0.88 (m, CH$_3$), 1.38-1.19 (m, 11H), 1.76-1.50 (m, 6H), 1.94-1.89 (m, 2 H), 2.28 (t, J=7.4 Hz, CH$_2$), 2.88 (d, J=10.8 Hz, 2 H), 3.96 (t, J=7.0 Hz, CH$_2$), 7.23-7.14 (m, 2 H), 7.36-7.32 (m, 1 H), 7.48-7.46 (m, 1 H); $^{13}$C NMR (CD$_3$OD) δ 14.5, 23.9, 25.7, 27.0, 28.5, 30.1, 32.9, 36.7, 37.3, 43.5, 54.9, 59.8, 112.3, 123.5, 123.7, 124.3, 127.7, 138.4, 171.4; HPLC-MS (ammonium acetate) [M+H]$^+$=361.3.

3.165 3-[5-(4-Propyloxypiperidin-1-yl)pentyl]-3H-benzothiazol-2-one (107LH03-2)

3-(5-Chloropentyl)-3H-benzothiazol-2-one (107LH01) (0.203 g, 0.9 mmol), 4-propyloxypiperidine (0.129 g, 0.9 mmol), KI (0.200 g, 1.2 mmol), and K$_2$CO$_3$ (0.166 g, 1.2 mmol) in MeCN (2 ml) were reacted according to GP19. Purified by flash CC (SiO$_2$; EtOAc, MeOH/EtOAc 1:4) to give the title compound (107LH03-2) (0.153 g, 47%). $^1$H NMR (CD$_3$OD) δ 0.90 (t, J=7.4 Hz, CH$_3$), 1.61-1.30(m, 9 H), 1.76-1.69 (m, 2 H), 1.90-1.84 (m, 2 H), 2.23-2.18 (m, 2 H), 2.35-2.31 (m, 2H), 2.76-2.74 (m, 2 H), 3.39-3.29 (m, 2 H), 3.95 (t, J=7.2 Hz, CH$_2$), 7.22-7.14 (m, 2 H), 7.36-7.32 (m, 1 H), 7.48-7.46 (m, 1 H); $^{13}$C NMR (CD$_3$OD) δ 11.0, 24.2, 25.6, 27.0, 28.4, 31.6, 43.5, 51.9, 59.2, 70.6, 112.3, 123.5, 123.7, 124.4, 127.7, 138.4, 171.5; HPLC-MS (ammonium acetate) [M+H]$^+$=363.3.

3.166 3-[6-(4-Butylpiperidin-1-yl)hexyl]-3H-benzothiazol-2-one (107LH04-1)

3-(6-Chlorohexyl)-3H-benzothiazol-2-one (107LH02) (0.243 g, 0.9 mmol), 4-butylpiperidine (0.127 g, 0.9 mmol), KI (0.200 g, 1.2 mmol), and K$_2$CO$_3$ (0.166 g, 1.2 mmol) in MeCN (2 ml) were reacted according to GP19. Purified by flash CC (SiO$_2$; EtOAc, MeOH/EtOAc 1:4) to give the title compound (107LH04-1) (0.186 g, 55%). $^1$H NMR (CD$_3$OD) δ 0.88 (m, CH$_3$), 1.47-1.19 (m, 15H), 1.72-1.63 (m, 4H), 1.94-1.89 (m, 2H), 2.28 (t, J=7.4 Hz, CH$_2$), 2.88 (d, J=11.0 Hz, 2 H), 3.94 (t, J=7.0 Hz, CH$_2$), 7.21-7.15 (m, 2 H), 7.35-7.31 (m, 1 H), 7.47-7.45 (m, 1 H); $^{13}$C NMR (CD$_3$OD) δ 14.5, 23.9, 27.2, 27.5, 28.3, 28.5, 30.1, 32.9, 36.7, 37.3, 43.6, 54.9, 59.9, 112.3, 123.5, 123.7, 124.3, 127.7, 138.4, 171.4; HPLC-MS (ammonium acetate) [M+H]$^+$=375.3.

3.167 3-[6-(4-Propyloxypiperidin-1-yl)hexyl]-3H-benzothiazol-2-one (107LH04-2)

3-(6-Chlorohexyl)-3H-benzothiazol-2-one (107LH02) (0.243 g, 0.9 mmol), 4-propyloxypiperidine (0.129 g, 0.9 mmol), KI (0.200 g, 1.2 mmol), and K$_2$CO$_3$ (0.166 g, 1.2 mmol) in MeCN (2 ml) were reacted according to GP19. Purified by flash CC (SiO$_2$; EtOAc, MeOH/EtOAc 1:4) to give the title compound (107LH04-1) (0.159 g, 47%). $^1$H NMR (CD$_3$OD) δ 0.90 (t, J=7.4 Hz, CH$_3$), 1.89-1.34 (m, 15 H), 2.32-2.17 (m, 4 H), 2.73 (br. s, 2 H), 3.39-3.30 (m, 2 H), 3.94 (t, J=6.7 Hz, CH$_2$), 7.22-7.14 (m, 2 H), 7.35-7.32 (m, 1 H), 7.48-7.46 (m, 1 H); $^{13}$C NMR (CD$_3$OD) δ 11.1, 24.3, 27.3, 27.5, 28.2, 28.5, 31.7, 43.5, 51.9, 59.4, 70.6, 112.3, 123.5, 123.7, 124.3, 127.7, 138.4, 171.4; HPLC-MS (ammonium acetate) [M+H]$^+$=377.3.

3.168 General Procedure 20 (GP20)

A 7 ml vial was charged with 1-(3-chloropropyl)-1,3-dihydrobenzoimidazol-2-one (210 mg, 1.0 mmol), amine (0.5 mmol), NaI (150 mg, 1.0 mmol), sodium carbonate (106 mg, 1.0 mmol) and MeCN (2 ml) and shaken at 60° C. for 18 h. The reaction was cooled to r.t. and water (1 ml) was added. The product was extracted into ethyl acetate (2×1 ml) and the organic layer loaded onto a Varian SCX ion exchange column. The column was washed with MeOH (2 column volumes) then the product was eluted off the column using 10% ammonium hydroxide in MeOH (2 column volumes). The solute was concentrated in vacuo, dissolved up in acetone, dried (K$_2$CO$_3$) and concentrated in vacuo before being purified further.

3.169 1-{3-[4-(2-Hydroxyethyl)piperidin-1-yl]propyl}-1,3-dihydrobenzoimidazol-2-one) (45NK-55)

The reaction was carried out according to the GP20 using 2-piperidin-4-ylethanol (65 mg, 0.5 mmol). The product was purified using an Isco CombiFlash Sq 16× (4.1 g silica column, eluting DCM (5 min), 0-20% MeOH in DCM (20 min), 20% MeOH in DCM (15 min)). MeOH (2 ml) and HCl in ether (2 M, 0.2 ml) were added, the solution concentrated to give the title compound (45NK-55) as the hydrochloride salt (4 mg). $^1$H NMR (CD$_3$OD) δ 1.44 (m, 2H), 1.52 (q, 2H), 1.74 (m, 1H), 1.95 (br. d, 2H), 2.17 (m, 2H), 2.86 (br. t, 2H), 3.08 (m, 2H), 3.45 (br. d, 2H), 3.61 (t, 2H), 4.01 (t, 2H), 7.14 (m, 3H), 7.19 (m, 1H); LC-MS [M+H]$^+$ 304.2.

3.170 1-[3-(3,5-Dimethylpiperidin-1-yl)propyl]-1,3-dihydrobenzoimidazol-2-one (45NK-56)

The reaction was carried out according to the GP20 using 3,5-dimethylpiperidine (57 mg, 0.5 mmol). MeOH (2 ml) and HCl in ether (2 M, 0.2 ml) were added, the solution concentrated and the product recrystallised from MeOH-ether to give the title compound (45NK-56) as the hydrochloride salt (17 mg). $^1$H NMR (CD$_3$OD) δ 0.95 (d, 1H), 0.97 (d, 4H), 1.21 (d, 1H), 1.41 (dt, 0.67H), 1.67 (br. d, 0.67H), 1.83-1.97 (m, 2H), 2.11 (m, 0.33H), 2.22 (m, 2H), 2.47 (m, 2H), 3.00 (dd, 09.33H), 3.17 (m, 2H), 3.36-3.45 (m, 2H), 3.96-4.08 (m, 2H), 7.16 (m, 3H), 7.21 (m, 1H); LC-MS [M+H]$^+$ 288.3 (2 peaks).

3.171 1-[3-(4-Methylpiperidin-1-yl)propyl]-1,3-dihydrobenzoimidazol-2-one (45NK-58)

The reaction was carried out according to the GP20 using 4-methylpiperidine (50 mg, 0.5 mmol). The product was purified using an Isco CombiFlash Sq 16× (4.1 g silica column, eluting DCM (5 min), 0-15% MeOH in DCM (20 min), 15% MeOH in DCM (15 min)). MeOH (2 ml) and HCl in ether (2 M, 0.2 ml) were added, the solution concentrated to give the title compound (45NK-58) as the hydrochloride salt (24 mg). $^1$H NMR (CDCl$_3$) δ 0.93 (d, 3H), 1.54 (m, 1H), 1.62-1.75 (m, 4H), 2.28 (tt, 2H), 2.53 (br. t, 2H), 2.94 (dd, 2H), 3.31 (br. d, 2H), 3.94 (t, 2H), 6.99 (m, 3H), 7.09 (m, 1H), 10.2 (br. s, 1H); LC-MS [M+H]$^+$ 274.2.

3.172 1-[3-(4-(Hydroxymethyl)piperidin-1-yl)propyl]-1,3-dihydrobenzoimidazol-2-one (45NK-60)

The reaction was carried out according to the GP20 using piperidin-4-ylMeOH (58 mg, 0.5 mmol). The product was purified using an Isco CombiFlash Sq 16× (4.1 g silica column, eluting DCM (5 min), 0-15% MeOH in DCM (20 min), 15% MeOH in DCM (15 min)). MeOH (2 ml) and HCl in ether (2 M, 0.2 ml) were added, the solution concentrated to give the title compound (45NK-60) as the hydrochloride salt (28 mg). $^1$H NMR (CD$_3$OD) δ 1.46 (dq, 2H), 1.69 (m, 1H), 1.92 (br. d, 2H), 2.16 (tt, 2H), 2.76 (br. t, 2H), 3.01 (dd, 2H), 3.40 (m, 2H), 3.43 (d, 2H), 4.00 (t, 2H), 7.08 (m, 3H), 7.20 (m, 1H); LC-MS [M+H]$^+$ 290.2.

3.173 1-{3-[4-(3-Methylbutylidene)piperidin-1-yl]propyl}-1,3-dihydrobenzoimidazol-2-one (45NK70)

The reaction was carried out according to the GP20 using 4-(3-methylbutylidene)piperidine hydrochloride (95 mg, 0.5 mmol). The product was purified using an Isco CombiFlash Sq 16× (4.1 g silica column, eluting DCM (5 min), 0-15% MeOH in DCM (20 min), 15% MeOH in DCM (15 min)). MeOH (2 ml) and HCl in ether (2 M, 0.2 ml) were added, the solution concentrated to give the title compound (45NK70) as the hydrochloride salt (10 mg). $^1$H NMR (CD$_3$OD) δ 0.86 (d, 6H), 1.55 (sept, 1H), 1.86 (t, 2H), 1.96 (tt, 2H), 2.18 (t, 2H), 2.22 (t, 2H), 2.40 (m, 6H), 3.93 (t, 2H), 5.15 (t, 1H), 7.06 (m, 3H), 7.16 (m, 1H); $^{13}$C NMR (CD$_3$OD) δ 22.7, 26.6, 28.8, 30.1, 36.6, 37.2, 39.9, 55.7, 56.6, 109.3, 110.4, 122.4, 122.7, 123.0, 129.6, 131.6, 137.1, 156.9; LC-MS [M+H]$^+$ 328.

3.174 1-[3-(4-Pentylpiperidin-1-yl)propyl]-1,3-dihydrobenzoimidazol-2-one (45NK71)

The reaction was carried out according to the GP20 using 4-pentylpiperidine hydrochloride trifluoroacetate (199 mg, 0.5 mmol). The product was purified using an Isco CombiFlash Sq 16× (4.1 g silica column, eluting DCM (5 min), 0-15% MeOH in DCM (20 min), 15% MeOH in DCM (15 min)). MeOH (2 ml) and HCl in ether (2 M, 0.2 ml) were added, the solution concentrated to give the title compound (45NK71) as the hydrochloride salt (4 mg). $^1$H NMR (CD$_3$OD) δ 0.88 (t, 3H), 1.14-1.35 (m, 11H), 1.66 (br. d, 2H), 1.95 (m, 4H), 2.42 (dd, 2H), 2.90 (br. d, 2H), 3.92 (t, 2H), 7.06 (m, 3H), 7.18 (m, 1H); LC-MS [M+H]$^+$ 330.3.

3.175 1-[3-(4-Butylpiperidin-1-yl)propyl]-3-methyl-1,3-dihydrobenzoimidazol-2-one (45NK110)

1-(3-Chloro-propyl)-3-methyl-1,3-dihydro-benzoimidazol-2-one (450 mg, 2.0 mmol), 4-butyl-piperidine (282 mg, 2.0 mmol), NaI (300 mg, 2.0 mmol) and sodium carbonate (212 mg, 2.0 mmol) were shaken in MeCN (5 ml) at 80° C. for 18 h. The reaction was cooled to r.t., water (5 ml) was added and the product extracted with ethyl acetate (2×20 ml). The organic layer was dried (K$_2$CO$_3$), filtered and concentrated in vacuo before being purified by using an Isco CombiFlash Sq 16× (10 g silica column, eluting 0-15% MeOH in DCM (33 min) then 15% MeOH in DCM (13 min)) to give the title compound (45NK110) (50 mg). The hydrochloride salt was formed by addition of HCl (4M in dioxane) and recrystallised from MeOH-Et$_2$O to give a white precipitate which was filtered and dried. $^1$H NMR (CD$_3$OD) δ 0.91 (t, 3H), 1.31 (m, 6H), 1.44 (m, 2H), 1.54 (m, 1H), 1.95 (br. s, 2H), 2.22 (m, 2H), 2.92 (br. t, 2H), 3.15 (m, 2H), 3.43 (s, 3H), 3.55 (m, 2H), 4.04 (t, 2H), 7.17 (m, 3H), 7.23 (m, 1H); m.p. 157.7-158.4° C.

3.176 General Procedure 21 (GP21)

The amine (0.10 mmol) in DCM (0.3 ml) and iodide (0.12 mmol) in DMF (0.2 ml) were added to a reaction vessel and DCM (1 ml) was added. The reactions were shaken at r.t. for 72 h then isocyanate resin (ca. 50 mg, 1.1 mmol/g) was added and the reactions were shaken at r.t. for 24 h. The reactions were filtered, washing with MeOH (1 ml) onto a SCX ion exchange column which had been prewashed with MeOH (2 column volumes). The column was washed with MeOH (2 column volumes) then the product was eluted off the column using 5% aqueous NH$_3$ in MeOH (1 column volume) and concentrated in vacuo. The product was purified by the general prep. LC-MS procedure and the desired fractions were concentrated in vacuo to give the desired product.

3.177 1-(4-[4-Cyclohexylmethyl-piperidin-1-yl]butyl)-1,3-dihydrobenzimidazol-2-one (56NK118B-cpd2)

4-(1-Cyclohexylmethyl)piperidine (18 mg, 0.10 mmol) and 1-(4-iodobutyl)-1,3-dihydrobenzoimidazol-2-one (38 mg, 0.12 mmol) were used according to general GP21 to give the trifluoroacetate salt of the title compound (56NK118-cpd2) (1.5 mg). HPLC-MS (ammonium acetate) [M+H]$^+$=370.5.

3.178 1-(3-[4-Cyclohexylmethyl-piperidin-1-yl]propyl)-1,3-dihydrobenzoimidazol-2-one (56NK138-A1)

4-(1-Cyclohexylmethyl)piperidine (18 mg, 0.10 mmol) and 1-(3-iodopropyl)-1,3-dihydrobenzoimidazol-2-one (36 mg, 0.12 mmol) were used according to GP21 to give the 3.179 1-(3-[4-(2-Ethoxyethyl)piperidin-1-yl]propyl)-1,3-dihydrobenzimidazol-2-one (56NK138-A2)

4-(2-Ethoxyethyl)piperidine (16 mg, 0.10 mmol) and 1-(3-iodopropyl)-1,3-dihydrobenzoimidazol-2-one (36 mg, 0.12 mmol) were used according to GP21 to give the trifluoroacetate salt of the title compound (56NK138-A2) (3.7 mg). HPLC-MS (ammonium acetate) [M+H]$^+$=332.4.

3.180 1-(3-[4-Cyclohexylmethyl-piperidin-1-yl]propyl)-3-methyl-1,3-dihydrobenzimidazol-2-one (56NK138-B1)

4-(1-Cyclohexylmethyl)piperidine (18 mg, 0.10 mmol) and 1-(3-iodopropyl)-3-methyl-1,3-dihydrobenzoimidazol-2-one (38 mg, 0.12 mmol) were used according to GP21 to give the trifluoroacetate salt of the title compound (56NK138-B1) (1.3 mg). HPLC-MS (ammonium acetate) [M+H]$^+$=370.5.

3.181 1-(3-[4-(2-Ethoxyethyl)piperidin-1-yl]propyl)-3-methyl-1,3-dihydrobenzimidazol-2-one (56NK138-B2)

4-(2-Ethoxyethyl)piperidine (16 mg, 0.10 mmol) and 1-(3-iodopropyl)-3-methyl-1,3-dihydrobenzoimidazol-2-one (38 mg, 0.12 mmol) were used according to GP21 to give the trifluoroacetate salt of the title compound (56NK138-B2) (7.3 mg). HPLC-MS (ammonium acetate) [M+H]$^+$=346.5.

3.182 3-(3-[4-Cyclohexylmethyl-piperidin-1-yl]propyl)-3H-benzothiazol-2-one (56NK138-C1)

4-(1-Cyclohexylmethyl)piperidine (18 mg, 0.10 mmol) and 1-(3-iodopropyl)-3H-benzothiazol-2-one (38 mg, 0.12 mmol) were used according to GP21 to give the trifluoroacetate salt of the title compound (56NK138-C1) (2.2 mg). HPLC-MS (ammonium acetate) [M+H]$^+$=373.4.

3.183 3-(3-[4-(2-Ethoxyethyl)piperidin-1-yl]propyl)-3H-benzothiazol-2-one (56NK138-C2)

4-(2-Ethoxyethyl)piperidine (16 mg, 0.10 mmol) and 1-(3-iodopropyl)-3H-benzothiazol-2-one (38 mg, 0.12 mmol) were used according to GP21 to give the trifluoroacetate salt of the title compound (56NK138-C2) (2.5 mg). HPLC-MS (ammonium acetate) [M+H]$^+$=349.4.

3.184 1-(3-[4-Allyloxy-piperidin-1-yl]propyl)-1,3-dihydrobenzimidazol-2-one (56NK136-A4)

4-(1-Cyclohexylmethyl)piperidine (18 mg, 0.10 mmol) and 1-(3-iodopropyl)-1,3-dihydrobenzoimidazol-2-one (36 mg, 0.12 mmol) were used according to GP21 to give the trifluoroacetate salt of the title compound (56NK136-A4) (10.8 mg). $^1$H NMR (CDCl$_3$) δ 8.17 (br. s, 1H), 7.03-7.26 (m, 4H), 5.93 (ap. ddd, J=17.2, 10.4, 5.5 Hz, 1H), 5.26 (ap. ddd, J=17.2, 3.2, 1.6 Hz, 1H), 5.15 (ap. ddd, J=10.4, 2.8, 1.4 Hz, 1H), 3.99 (ap. dt, J=5.5, 1.7 Hz, 2H), 3.93 (t, J=6.8 Hz, 2H), 3.35 (m, 1H), 2.73 (m, 2H), 2.39 (t, J=7.1 Hz, 2H), 2.10 (m, 2H), 1.95 (tt, J=7.1, 6.8, 2H), 1.90 (m, 2H), 1.63 (m, 2H); HPLC-MS (ammonium acetate) [M+H]$^+$=316.40.

3.185 1-(3-[4-Allyloxy-piperidin-1-yl]propyl)-3-methyl-1,3-dihydrobenzimidazol-2-one (56NK136-B4)

4-(2-Ethoxyethyl)piperidine (16 mg, 0.10 mmol) and 1-(3-iodopropyl)-3-methyl-1,3-dihydrobenzoimidazol-2-one (38 mg, 0.12 mmol) were used according to GP21 to give the trifluoroacetate salt of the title compound (56NK136-B4) (8.3 mg). $^1$H NMR (CDCl$_3$) δ 7.07 (m, 3H), 6.97 (m, 1H), 5.93 (ap. ddd, J=17.2, 10.4, 5.5 Hz, 1H), 5.27 (ap. ddd, J=17.2, 3.2, 1.7 Hz, 1H), 5.15 (ap. ddd, J=10.4, 3.0, 1.8 Hz, 1H), 3.99 (ap. dt, J=5.5, 1.7 Hz, 2H), 3.94 (t, J=6.9 Hz, 2H), 3.42 (s, 3H), 3.36 (m, 1H), 2.72 (m, 2H), 2.39 (m, 2H), 2.10 (m, 2H), 1.92 (m, 4H), 1.61 (m, 2H); HPLC-MS (ammonium acetate) [M+H]$^+$=330.4.

3.186 General Procedure 22 (GP22)

The amine (0.10 mmol) in DCM (0.3 ml) and iodide (0.12 mmol) in DMF (0.2 ml) were added to a reaction vessel and DCM (1 ml) was added. The reactions were shaken at r.t. for 72 h then isocyanate resin (ca. 50 mg, 1.1 mmol/g) was added and the reactions were shaken at r.t. for 24 h. The reactions were filtered, washing with MeOH (1 ml) onto a SCX ion exchange column which had been prewashed with MeOH (2 column volumes). The column was washed with MeOH (2 column volumes) then the product was eluted off the column using 5% aqueous NH$_3$ in MeOH (1 column volume) and concentrated in vacuo. The product was purified by the general prep. LC-MS procedure and the desired fractions were made pH 12 by addition of sodium hydroxide (2M). The product was extracted with EtOAc (3×5 ml), and the organic layer washed with brine (5 ml), dried (K$_2$CO$_3$) and concentrated in vacuo to give the desired compound.

3.187 1-(3-[4-Methyl-piperidin-1-yl]propyl)-3-methyl-1,3-dihydrobenzimidazol-2-one (56NK125-A)

4-Methylpiperidine (10 mg, 0.10 mmol) and 1-(3-iodopropyl)-3-methyl-1,3-dihydrobenzoimidazol-2-one (38 mg, 0.12 mmol) were used according to GP22 to give the title compound (56NK125-A) (8.4 mg). $^1$H NMR (CDCl$_3$) δ 7.07 (m, 3H), 6.96 (m, 1H), 3.94 (t, J=7.0 Hz, 2H), 3.41 (s, 3H), 2.84 (m, 2H), 2.37 (m, 2H), 1.93 (m, 4H), 1.61 (m, 2H), 1.34 (m, 1H), 1.24 (m, 2H), 0.92 (d, J=6.2 Hz, 3H); HPLC-MS (ammonium acetate) [M+H]$^+$=288.4.

3.188 1-[2-(4-Butylpiperidin-1-yl)ethyl]-1,3-dihydrobenzoimidazol-2-one (56NK117-A)

4-Butylpiperidine (14 mg, 0.10 mmol) and 1-(2-iodoethyl)-1,3-dihydrobenzoimidazol-2-one (35 mg, 0.12 mmol) were used according to GP22 to give the title compound (56NK117-A) (7.6 mg). HPLC-MS (ammonium acetate) [M+H]$^+$=302.4.

3.189 1-[4-(4-Butylpiperidin-1-yl)butyl]-1,3-dihydrobenzoimidazol-2-one (56NK118-A)

4-Butylpiperidine (14 mg, 0.10 mmol) and 1-(4-iodobutyl)-1,3-dihydrobenzoimidazol-2-one (38 mg, 0.12 mmol) were used according to GP22 to give the title compound (56NK118-A) (11.6 mg). $^1$H NMR (CDCl$_3$) δ 9.02 (br. s, 1H), 7.06 (m, 3H), 7.01 (m, 1H), 3.90 (t, J=7.0 Hz, 2H), 2.89 (m, 2H), 2.37 (m, 2H), 1.89 (m, 2H), 1.79 (m, 2H), 1.64 (m, 4H), 1.23 (m, 9H), 0.88 (m, 3H); HPLC-MS (ammonium acetate) [M+H]$^+$=330.4.

3.190 3-[4-(4-Butylpiperidin-1-yl)butyl]-3H-benzooxazole-2-thione (56NK139C1)

3-(4-Chlorobutyl)-3H-benzooxazole-2-thione (68 mg, 0.28 mmol) and NaI (210 mg, 1.4 mmol) in acetone (10 ml) were heated to 50° C. for 72 h then cooled to r.t. Aqueous sodium thiosulphate solution (10 ml) was added and the product was extracted into EtOAc (2×20 ml). The organic layer was dried (K$_2$CO$_3$), filtered and concentrated in vacuo. DMF (0.2 ml), DCM (1 ml) and 4-butylpiperidine (14 mg, 0.1 mmol) in acetonitile (0.2 ml) were added and the reaction was shaken at r.t. for 72 h then isocyanate resin (ca. 50 mg, 1.1 mmol/g) was added and the reactions were shaken at r.t. for 24 h. The reactions were filtered, washing with MeOH (1 ml) onto a SCX ion exchange column which had been prewashed with MeOH (2 column volumes). The column was washed with MeOH (2 column volumes) then the product was eluted off the column using 5% aqueous NH$_3$ in MeOH (1 column volume) and concentrated in vacuo. The product was purified by preparative LC/MS (method TJ1) and the desired fractions were concentrated in vacuo to give the trifluoroacetate salt of the title compound (56NK139C1) (0.4 mg). HPLC-MS (ammonium acetate) [M+H]$^+$=347.4.

3.191  1-(3-[4-Cyclohexylpiperidin-1-yl]propyl)-1,3-dihydrobenzimidazol-2-one (75NK58-A2)

4-Cyclohexylpiperidine (33 mg, 0.20 mmol) in DCM (0.5 ml) and MeCN (0.5 ml) was added to 1-(3-iodopropyl)-1,3-dihydrobenzoimidazol-2-one (76 mg, 0.24 mmol), K$_2$CO$_3$ (66 mg, 0.48 mmol) and NaI (72 mg, 0.48 mmol). The reaction was stirred at r.t. for 36 h then aqueous sodium thiosulphate solution (5 ml) was added. The product was extracted into EtOAc (2×10 ml), and the organic layer was dried (K$_2$CO$_3$), filtered and concentrated in vacuo. MeOH (1 ml) was added and the compound was loaded onto a SCX ion exchange column which had been prewashed with MeOH (2 column volumes). The column was washed with MeOH (2 column volumes) then the product was eluted off the column using 5% aqueous NH$_3$ in MeOH (1 column volume) and concentrated in vacuo. The product was purified by preparative LC/MS (method TJ1) and the desired fractions were made pH 12 by addition of sodium hydroxide (2M). The product was extracted with EtOAc (3×5 ml), and the organic layer washed with brine (5 ml), dried (K$_2$CO$_3$) and concentrated in vacuo to give the title compound (75NK58-A2) (12.1 mg). $^1$H NMR (CDCl$_3$) δ 9.25 (br. s, 1H), 7.07 (m, 4H), 3.93 (t, J=7.0 Hz, 2H), 2.93 (m, 2H), 2.40 (m, 2H), 1.98 (pent, J=7.0 Hz, 2H), 1.86 (m, 2H), 1.69 (m, 7H), 1.32-0.87 (m, 9H); HPLC-MS (ammonium acetate) [M+H]$^+$=342.3.

3.192  1-(3-[4-Cyclohexylpiperidin-1-yl]propyl)-3H-benzothiazol-2-one (75NK58-B2)

4-Cyclohexylpiperidine (33 mg, 0.20 mmol) in DCM (0.5 ml) and MeCN (0.5 ml) was added to 1-(3-iodopropyl)-3H-benzothiazol-2-one (77 mg, 0.24 mmol), K$_2$CO$_3$ (66 mg, 0.48 mmol) and NaI (72 mg, 0.48 mmol). The reaction was stirred at r.t. for 36 h then aqueous sodium thiosulphate solution (5 ml) was added. The product was extracted into EtOAc (2×10 ml), and the organic layer was dried (K$_2$CO$_3$), filtered and concentrated in vacuo. MeOH (1 ml) was added and the compound was loaded onto a SCX ion exchange column which had been prewashed with MeOH (2 column volumes). The column was washed with MeOH (2 column volumes) then the product was eluted off the column using 5% aqueous NH$_3$ in MeOH (1 column volume) and concentrated in vacuo. The product was purified by preparative LC/MS (method TJ1) and the desired fractions were made pH 12 by addition of sodium hydroxide (2M). The product was extracted with EtOAc (3×5 ml), and the organic layer washed with brine (5 ml), dried (K$_2$CO$_3$) and concentrated in vacuo to give the title compound (75NK58-B2) (9.1 mg). HPLC-MS (ammonium acetate) [M+H]$^+$=359.2.

3.193  1-(3-(4-Butylpiperidin-1-yl)propyl)-1H-indol-2,3-dione (85LM03c)

A 50 ml flask, charged with 4-butylpiperidine (0.042 g, 0.30 mmol), 1-(3-iodopropyl)-1H-indol-2,3-dione (85LM05) (0.113 g, 0.36 mmol) and K$_2$CO$_3$ (0.062 g, 0.45 mmol) in CH$_3$CN (20 ml), was stirred at 50° C. for 24 hours. Water (10 ml) and EtOAc (10 ml) were added and the phases were separated. The water phase was re-extracted with EtOAc (10 ml). The combined organic phases were dried (Na$_2$SO$_4$) and evaporated to dryness. The crude product was purified by column chromatography (SiO$_2$; EtOAc/n-heptane 1:1+1% Et$_3$N) to give the title compound (85LM03c) (0.012 g, 10%). $^1$H NMR (CDCl$_3$) δ 0.95 (t, 3H), 1.10-1.30 (m, 8H), 1.60 (d, 2H), 1.75-1.80 (m, 1H), 1.85-1.95 (m, 4H), 2.40 (t, 2H), 2.80 (d, 2H), 3.80 (t, 2H), 7.0 (d, 1H), 7.10 (t, 1H), 7.55-7.65 (m, 2H); HPLC-MS (ammonium acetate) [M+H]$^+$=329.3.

3.194  1-(3-(4-Butylpiperidin-1-yl)propyl)-1,3-dihydro-indol-2-one (85LM12)

A mixture of compound 1-(3-(4-Butyl-piperidin-1-yl)-propyl)-1H-indol-2,3-dione (85LM03c) (0.030 g, 0.09 mmol) and 10% Pd/C catalyst (0.016 g) in acetic acid (1.4 ml) containing 70% perchloric acid (0.014 ml) was hydrogenated at 50° C. for 20 hours. After removal of the catalyst (filtration of the solution through celite and wash with ethanol) the solution was evaporated. Water (10 ml) and EtOAc (10 ml) were added to the residue followed by addition of sodium hydroxide (1-2 drops) until pH 7. The EtOAc phase was separated, dried (Na$_2$SO$_4$) and evaporated to dryness. The crude product was purified by column chromatography (SiO$_2$; EtOAc/n-heptane 1:3+1% Et$_3$N) to give the title compound (85LM12) (0.001 g, 4%). $^1$H NMR (CDCl$_3$) δ 0.95 (t, 3H), 1.10-1.30 (m, 8H), 1.60 (d, 2H), 1.75-1.80 (m, 1H), 1.85-1.95 (m, 4H), 2.40 (t, 2H), 2.80 (d, 2H), 3.48 (s, 2H), 3.80 (t, 2H), 6.90-6.95 (m, 1H), 7.00-7.05 (m, 1H), 7.20-7.30 (m, 2H); HPLC-MS (ammonium acetate) [M+H]$^+$=314.3.

3.195  3-(3-(4-Butylpiperidin-1-yl)propyl)-1H-indole (85LM18)

A 100 ml flask, charged with 4-butylpiperidine (1.7 g, 12.0 mmol), crude toluene-4-sulfonic acid 3-(1H-indol-3-yl)-propyl ester (85LM17) (4.0 g) and K$_2$CO$_3$ (2.0 g, 14.4 mmol) in CH$_3$CN (20 ml), was stirred at 50° C. for 24 hours. Water (20 ml) and EtOAc (20 ml) were added and the phases were separated. The aqueous phase was re-extracted with EtOAc (20 ml). The combined organic phases were dried (Na$_2$SO$_4$) and evaporated to dryness. The crude product was purified by column chromatography (SiO$_2$; EtOAc/n-heptane 1:3) to give the title compound (85LM18) (0.8 g, 10%-3 steps). $^1$H NMR (CDCl$_3$) δ 0.95 (t, 3H), 1.18-1.38 (m, 8H), 1.65 (d, 3H), 1.83-1.98 (m, 4H), 2.40 (t, 2H), 2.78 (t, 2H), 2.90 (d, 2H), 6.98 (s, 1H), 7.10 (t, 1H), 7.20 (t, 1H), 7.35 (d, 1H), 7.62 (d, 1H); HPLC-MS (ammunium acetate) [M+H]$^+$=299.3.

3.196  3-(3-(4-Butylpiperidin-1-yl]propyl)-1,3-dihydro-indol-2-one (85LM23)

3-(3-(4-Butylpiperidin-1-yl)propyl)-1H-indole (85LM18) (0.156 g, 0.52) was dissolved in DMSO (1 ml) in a 10 ml flask and stirred at room temperature. Concentrated hydrochloric acid (0.04 ml, 0.52 mmol) was added slowly and stirring was continued for 24 hours. Water (10 ml) was added and then aqueous sodium bicarbonate (10-20 ml) until pH 7 followed by extraction with EtOAc (2×20 ml). The combined organic phases were dried (Na$_2$SO$_4$) and evaporated to dryness. The crude product was purified by column chromatography (SiO$_2$; EtOAc/n-heptane 1:10) and prep. RP-HPLC (conditions: stationary phase, Luna 15 um C18; column, 250×21.2 mm; mobile phase, 20 ml/min, H$_2$O/CH$_3$CN, ammoniumacetate buffer (25 nM)) to give the title compound (85LM23) (0.002 g, 1%). $^1$H NMR (CDCl$_3$) δ 0.95 (t, 3H), 1.10-1.30 (m, 8H), 1.50-1.70 (m, 5H), 1.80-1.90 (m, 2H), 1.90-2.00 (m, 2H), 2.30 (m, 2H), 2.85 (m, 2H), 3.45 (m, 2H), 6.80 (d, 1H), 7.00 (t, 1H), 7.20-7.30 (m, 2H); HPLC-MS (ammonium acetate) [M+H]$^+$=315.3.

3.197 General Procedure 23 (GP23)

A 7 ml sealed vial, charged with 4-propoxy-piperidine (1 equiv), chloroalkylheterocycle (1 equiv), NaI (2 equiv) and K$_2$CO$_3$ (equiv) in MeCN (4 ml), was stirred at 50° C. for 24 hours. The mixture was poured into water (20 ml) followed by extraction with EtOAc (2×20 ml). The combined organic phases were dried (Na$_2$SO$_4$) and evaporated to dryness. The crude product was purified by column chromatography (SiO$_2$; MeOH/DCM 1:20).

3.198  3-(3-(4-Propoxypiperidine-1-yl)-propyl)-3H-benzooxazol-2-one (85LM37).

3-(3-Chloropropyl)-3H-benzooxazol-2-one (62KK30) (0.200 G, 0.95 mmol), 4-propoxypiperidine (0.138 g, 0.95 mmol), NaI (0.285 g, 1.90 mmol), and K$_2$CO$_3$ (0.262 g, 1.90 mmol) were reacted according to GP23 to give the title compound (85LM37) (0.211 g, 70%). $^1$H NMR (CDCl$_3$) δ 0.95 (t, 3H), 1.50-1.65 (m, 4H), 1.80-1.90 (m, 2H), 1.95-2.00 (m, 2H), 2.00-2.10 (m, 2H), 2.40 (t, 2H), 2.65-2.75 (m, 2H), 3.20-3.30 (m, 1H), 3.40 (t, 2H), 3.90 (t, 2H), 7.05-7.15 (m, 2H), 7.15-7.25 (m, 2H); HPLC-MS (ammonium acetate) [M+H]$^+$=319.3.

3.199  1-(3-(4-Butylpiperidine-1-yl)propyl)-1,3-dihydro-benzimidazol-2-one (85LM35).

1-(3-chloropropyl)-1,3-dihydro-benzimidazol-2-one (0.200 G, 0.95 mmol), 4-propoxypiperidine (0.138 g, 0.95 mmol), NaI (0.285 g, 1.90 mmol), and K$_2$CO$_3$ (0.262 g, 1.90 mmol) were reacted according to GP23 to give the title compound (85LM35) (0.183 g, 60%). $^1$H NMR (CD$_3$OD) δ 0.95 (t, 3H), 1.50-1.65 (m, 2H), 1.75-1.85 (m, 2H), 1.95-2.05 (m, 2H), 2.15 (m, 2H), 2.85-3.00 (m, 4H), 3.10-3.20 (m, 2H), 3.40 (t, 2H), 3.55 (m, 1H), 4.00 (t, 2H), 7.05-7.15 (m, 3H), 7.20 (d, 1H); HPLC-MS (ammonium acetate) [M+H]$^+$=318.3.

3.200  3-(3-(4-Butyl-piperidin-1-yl)-2-hydroxy-propyl)-3H-benzothiazol-2-one (85LM15).

A 50 ml flask, charged with 4-butylpiperidine (0.152 g, 1.1 mmol), crude 3-(3-bromo-2-hydroxypropyl)-3H-benzothiazol-2-one (85LM04) (0.308 g) and K$_2$CO$_3$ (0.295 g, 2.1 mmol) in MeCN (10 ml), was stirred at 50° C. for 24 hours. Water (10 ml) and EtOAc (10 ml) were added and the phases were separated. The aqueous phase was re-extracted with EtOAc (10 ml). The combined organic phases were dried (Na$_2$SO$_4$) and evaporated to dryness. The crude product was purified by column chromatography (SiO$_2$; EtOAc/n-heptane 1:3) to give the title compound (85LM15) (0.261 g, 28%-2 steps). $^1$H NMR (CDCl$_3$) δ 0.90-1.0 (m, 6H), 1.15-1.30 (m, 9H), 1.60-1.70 (m, 2H), 1.90 (t, 1H), 2.25 (t, 1H), 2.40 (m, 1H), 2.05 (dd, 1H), 2.75 (d, 1H), 2.90 (d, 1H), 3.90 (dd, 1H), 4.00-4.15 (m, 2H), 7.10-7.20 (m, 1H), 7.25-4.05 (m, 3H); HPLC-MS (ammonium acetate) [M+H]$^+$=349.1.

3.201 General Procedure 24 (GP24)

A 100 ml flask, charged with piperidine (1 equiv), 3-(3-chloro-2-methylpropyl)-3H-benzothiazol-2-one (85LM13) (1.2 equiv), NaI (2 equiv) and K$_2$CO$_3$ (2 equiv) in MeCN (30 ml), was stirred at 100° C. for 5 days. Water (20 ml) and EtOAc (20 ml) were added and the phases were separated. The aqueous phase was re-extracted with EtOAc (20 ml). The combined organic phases were dried (Na$_2$SO$_4$) and evaporated to dryness. The crude product was purified by column chromatography (SiO$_2$; EtOAc/n-heptane 1:3).

3.202  3-(3-(4-Butyl-piperidin-1-yl)-2-methyl-propyl)-3H-benzothiazol-2-one (85LM14).

4-Butylpiperidine (0.471 g, 3.3 mmol), 3-(3-chloro-2-methylpropyl)-3H-benzothiazol-2-one (0.964 g, 4.0 mmol), NaI (1.0 g, 6.7 mmol), and K$_2$CO$_3$ (0.93 g, 6.7 mmol) were reacted according to GP24 to give the title compound (85LM14) (0.344 g, 25%). $^1$H NMR (CDCl$_3$) δ 0.90-1.0 (m, 6H), 1.15-1.30 (m, 9H), 1.55-1.65 (m, 2H), 1.80 (t, 1H), 1.95 (t, 1H), 2.15-2.30 (m, 3H), 2.70 (d, 1H), 2.90 (d, 1H), 3.80 (dd, 1H), 4.05 (dd, 1H), 7.10-7.20 (m, 2H), 7.30 (t, 1H), 7.40 (d, 1H); HPLC-MS (ammonium acetate) [M+H]$^+$=347.3.

3.203  3-(3-(4-Propoxy-piperidin-1-yl)-2-methyl-propyl)-3H-benzothiazol-2-one (85LM49B).

4-Propxypiperidine (79KS66) (0.150 g, 0.62 mmol), 3-(3-chloro-2-methylpropyl)-3H-benzothiazol-2-one (85LM13) (0.179 g, 0.74 mmol), NaI (0.185 g, 1.2 mmol), and K$_2$CO$_3$ (0.172 g, 1.2 mmol) were reacted according to GP24 to give the title compound (85LM49b) (0.049 g, 23%). $^1$H NMR (CDCl$_3$) δ 0.90-1.0 (m, 6H), 1.45-1.60 (m, 4H), 1.80-1.90 (m, 2H), 2.00 (t, 1H), 2.10-2.30 (m, 4H), 2.60 (m, 1H), 2.80 (m, 1H), 3.20 (m, 1H), 3.40 (t, 2H), 3.80 (dd, 1H), 4.00 (dd, 1H), 7.10-7.20 (m, 2H), 7.30 (d, 1H); HPLC-MS (ammonium acetate) [M+H]$^+$=349.2.

3.204 General Procedure 25 (GP25)

A 100 ml flask, charged with 4-butyl-piperidine (1 equiv), toluene-4-sulfonic acid ester (1 equiv) and K$_2$CO$_3$ (1 equiv) in MeCN (20 ml), was stirred at 40° C. for 48 hours. Water (20 ml) and EtOAc (20 ml) were added and the phases were separated. The aqueous phase was re-extracted with EtOAc (20 ml). The combined organic phases were dried (Na$_2$SO$_4$) and evaporated to dryness. The crude product was purified by CC (SiO$_2$; MeOH/DCM 1:50).

3.205  3-(3-(4-Butyl-piperidin-1-yl)-(S)-3-hydroxy-2-methyl-propyl)-3H-benzothiazol-2-one (85LM74-62S).

Toluene-4-sulfonic acid (R)-2-methyl-3-(2-oxobenzothiazol-3-yl)-propyl ester (85LM73-61) (0.900 g, 2.4 mmol), 4-butylpiperidine (0-336 g, 2.4 mmol), and K$_2$CO$_3$ (0.30 g, 2.4 mmol) were reacted according to GP25 to give the title compound (85LM74-62S) (0.450 g, 24%). $^1$H NMR (CDCl$_3$) δ 0.90-1.0 (m, 6H), 1.15-1.30 (m, 9H), 1.55-1.65 (m, 2H), 1.80 (t, 1H), 1.95 (t, 1H), 2.15-2.30 (m, 3H), 2.70 (d, 1H), 2.90 (d, 1H), 3.80 (dd, 1H), 4.05 (dd, 1H), 7.10-7.20 (m, 2H), 7.30 (t, 1H), 7.40 (d, 1H); HPLC-MS (ammonium acetate) [M+H]$^+$=347.3.

3.206  3-(3-(4-Butylpiperidin-1-yl)-(R)-3-hydroxy-2-methylpropyl)-3H-benzothiazol-2-one (85LM91-78R).

Toluene-4-sulfonic acid (S)-2-methyl-3-(2-oxo-benzothiazol-3-yl)-propyl ester (85LM90-77) (0.900 g, 2.4 mmol), 4-butylpiperidine (0-336 g, 2.4 mmol), and K$_2$CO$_3$ (0.30 g, 2.4 mmol) were reacted according to GP25 to give the title compound (85LM91-78R) (0.450 g, 24%). $^1$H NMR (CDCl$_3$) δ 0.90-1.0 (m, 6H), 1.15-1.30 (m, 9H), 1.55-1.65 (m, 2H), 1.80 (t, 1H), 1.95 (t, 1H), 2.15-2.30 (m, 3H), 2.70 (d, 1H), 2.90 (d, 1H), 3.80 (dd, 1H), 4.05 (dd, 1H), 7.10-7.20 (m, 2H), 7.30 (t, 1H), 7.40 (d, 1H); HPLC-MS (ammonium acetate) [M+H]$^+$=347.3.

3.207 General Procedure 26 (GP26)

A mixture of 3-(3-Iodopropyl)-3H-benzothiazol-2-one (61KS80) (1.2 equiv), an amine (1.0 equiv) and K$_2$CO$_3$ (2.0 equiv) in MeCN/DCM (1:2, 3 mL) was shaken at 40° C. for 15 h. The mixture was cooled to room temperature before adding resin bound isocyanate (ArgoNaut Technologies Inc., PS-isocyanate, 3 equiv) and was then left standing for 18 h. Thereafter filtration through cotton wool was performed and subsequently purified by ionexchange (Varian BondElut®-SCX, H$^+$). Elution with 2.5% NH$_4$OH in MeOH and concentration gave the title compounds.

3.208 3-[3-(3-Pent-1-ynyl-8-aza-bicyclo[3.2.1]oct-2-en-8-yl)propyl]-3H-benzothiazol-2-one (79KS38-5).

3-Pent-1-ynyl-8-azabicyclo[3.2.1]oct-2-ene (79KS36-5) (0.033 g, 0.188 mmol), 3-(3-Iodopropyl)-3H-benzothiazol-2-one (61KS80) (0.072 g, 0.226 mmol), and $K_2CO_3$ (0.052 g, 0.376 mmol) were reacted according to GP26 to give the title compound (79KS38-5) (0.018 g, 26%). $^1$H NMR (CDCl$_3$) δ 0.98 (t, 3H, J=7.5 Hz, —CH$_2$CH$_2$CH$_3$), 1.57 (sixt, 2H, J=7.5 Hz, —CH$_2$CH$_2$CH$_3$), 1.59 (ddd, 1H, J=6.8 Hz, 8.3 Hz, J=13.9 Hz), 1.71 (d, 1H, J=18.0 Hz), 1.85 (td, 1H, J=3.0 Hz, J=9.0 Hz), 1.89-2.02 (m, 3H), 2.11 (m, 1H), 2.26 (t, 2H, J=7.2 Hz, —CH$_2$CH$_2$CH$_2$—N(from bicyclo[3.2.1]-oct-2-en-8-yl system)), 2.53 (m, 1H, J=18.0 Hz), 2.56-2.68 (m, 2H), 3.31 (dd, 1H, J=4.5 Hz, 8.1 Hz), 3.35 (t, 1H, J=5.4Hz), 4.04 (t, 2H, J=6.8 Hz, N(from Ar)—CH$_2$CH$_2$CH$_2$—), 6.02 (d, 1H, J=5.6 Hz, H2 (from bicyclo[3.2.1]-oct-2-en-8-yl system), 7.01-7.44 (m, 4H, Ar); $^{13}$C NMR (CDCl$_3$): δ 13.7, 21.5, 22.4, 26.7, 29.8, 33.8, 35.4, 41.3, 45.5, 55.6, 57.0, 80.7, 89.6, 111.1, 118.5, 122.7, 123.0, 123.1, 126.4, 135.3, 137.6, 170.2. HPLC-MS (ammonium acetate): [M+H]$^+$=367.31

3.209 3-[3-(3-Hex-ynyl-8-aza-bicyclo[3.2.1]oct-2-en-8-yl)propyl]-3H-benzothiazol-2-one (79KS38-6).

3-Hex-1-ynyl-8-azabicyclo[3.2.1]oct-2-ene (79KS36-6) (0.049 g, 0.259 mmol), 3-(3-Iodopropyl)-3H-benzothiazol-2-one (61KS80) (0.099 g, 0.311 mmol) and $K_2CO_3$ (0.072 g, 0.518 mmol) were reacted according to GP26 to give the title compound (79KS38-6) (0.053 g, 54%). $^1$H NMR (CDCl$_3$) δ 0.90 (t, 3H, J=7.0 Hz, —CH$_3$), 1.34-1.52 (m, 4H, —CH$_2$CH$_2$CH$_2$CH$_3$), 1.55 (ddd, 1H, J=6.6 Hz, 9.0 Hz, 12.1 Hz), 1.66 (d, 1H, J=17.6 Hz), 1.85 (td, 1H, J=2.6 Hz, 10.8 Hz), 1.86-1.97 (m, 3H), 2.06 (m, 1H), 2.26 (t, 2H, J=7.2 Hz, —CH$_2$CH$_2$CH$_2$—N (from bicyclo[3.2.1]-oct-2-en-8-yl system), 2.49 (d, 1H, J=17.6 Hz), 2.56 (m, 2H), 3.25 (dd, 1H, J=4.6 Hz, 6.9 Hz), 3.28 (t, 1H, J=5.8 Hz), 4.02 (t, 2 Hz, Ar)—CH$_2$CH$_2$CH$_2$—), 6.01 (d, 1H, J=6.8 Hz, H2(from bicyclo[3.2.1]-oct-2-en-8-yl system); $^{13}$C NMR (CDCl$_3$) δ 13.8, 19.2, 22.2, 26.8, 29.3, 31.1, 33.9, 35.4, 41.3, 45.6, 55.5, 56.9, 80.7, 89.4, 111.1, 118.4, 122.7, 123.0, 123.1, 126.4, 135.7, 137.7, 170.1; HPLC-MS (ammonium acetate): [M+H]$^+$=381.32

3.210 3-[3-(3-Hept-1-ynyl-8-aza-bicyclo[3.2.1]oct-2-en-8-yl)propyl]-3H-benzothiazol-2-one (79KS38-7).

3-Hept-1-ynyl-8-azabicyclo[3.2.1]oct-2-ene (79KS36-7) (0.051 g, 0.250 mmol), 3-(3-Iodopropyl)-3H-benzothiazol-2-one (61KS80) (0.096 g, 0.300 mmol) and $K_2CO_3$ (0.069 g, 0.500 mmol) were reacted according to GP26 to give the title compound (79KS38-7) (0.057 g, 58%). $^1$H NMR (CDCl$_3$) δ 0.90 (t, 3H, J=7.1 Hz, —CH$_2$CH$_2$CH$_2$CH$_3$), 1.24-1.40 (m, 4H), 1.44-1.54 (m, 2H), 1.59 (ddd, 1H, J=5.5 Hz, 9.1 Hz, 13.1 Hz), 1.72 (d, 1H, J=18.0 Hz), 1.84 (td, 1H, J=2.8 Hz, 8.3 Hz), 1.90-2.06 (m, 3H), 2.06-2.18 (m, 1H), 2.28 (t, 2H, J=6.9 Hz, —CH$_2$CH$_2$CH$_2$—N(from bicyclo[3.2.1]-oct-2-en-8-yl system), 2.52 (d, 1H, J=18.0 Hz), 2.64 (m, 2H), 3.26-3.42 (m, 2H), 4.04 (t, 2H, J=6.9 Hz, N (from Ar)—CH$_2$CH$_2$CH$_2$—), 6.02 (d, 1H, J=5.9 Hz), 7.06-7.44 (m, 4H, Ar); $^{13}$C NMR (CDCl$_3$) δ 14.1, 19.5, 22.4, 26.6, 28.7, 29.8, 31.3, 33.8, 35.3, 41.2, 45.5, 55.6, 57.0, 80.5 and 90.0 (sp C's), 111.1, 118.6, 122.6, 123.3, 126.4, 137.6 (Ar), 170.2 (C=O); HPLC-MS (ammonium acetate): [M+H]$^+$=395.34

3.211 3-{3-[3-(4-Hydroxy-but-1-ynyl)-8-aza-bicyclo[3.2.1]oct-2-en-8-yl]propyl}-3H-benzothiazol-2-one (79KS38-2).

4-(8-Azabicyclo[3.2.1]oct-2-en-3-yl)-but-3-yn-1-ol (79KS36-2) (0.018 g 0.102 mmol), 3-(3-Iodopropyl)-3H-benzothiazol-2-one (61KS80) (0.039 g, 0.122 mmol) and $K_2CO_3$ (0.028 g, 0.204 mmol) were reacted according to GP26 to give the title compound (79KS38-2) (0.022 g, 59%). $^1$H NMR (CDCl$_3$) δ 1.56 (ddd, 1H, J=5.9 Hz, 9.3 Hz, 13.2 Hz), 1.67 (d, 1H, J=17.6 Hz), 1.83 (td, 1H, J=2.3 Hz, 9.1 Hz), 1.87 (m, 6H), 2.02-2.15 (m, 1H), 2.51 (m, 1H, 17.6 Hz), 2.54-2.64 (m, 4H), 3.27 (dd, 1H, J=4.7 Hz, 7.1 Hz), 3.31 (t, 1H, J=5.7 Hz), 3.71 (t, 2H, J=6.3 Hz, —CH$_2$CH$_2$OH), 4.04 (t, 2H, J=7.0 Hz, N(from Ar)—CH$_2$CH$_2$CH$_2$—), 6.08 (d, 1H, J=5.6 Hz, H2 (from bicyclo[3.2.1]-oct-2-en-8-yl system)), 7.10-7.44 (m, 4H, Ar); $^{13}$C NMR (CDCl$_3$) δ 24.0, 26.8, 29.9, 33.8, 35.3, 41.3, 45.7, 55.5, 57.0, 61.3, 82.7, 85.4, 111.1, 117.9, 122.7, 123.0, 123.1, 126.4, 136.9, 137.7, 170.2. HPLC-MS (ammonium acetate): [M+H]$^+$=369.28

3.212 3-{3-[3-(5-Hydroxy-pent-1-ynyl)-8-aza-bicyclo[3.2.1]oct-2-en-8-yl]propyl}-3H-benzothiazol-2-one (79KS38-3).

5-(8-Azabicyclo[3.2.1]oct-2-en-3-yl)-pent-4-yn-1-ol (79KS36-3) (0.045 g, 0.235 mmol), 3-(3-Iodopropyl)-3H-benzothiazol-2-one (61KS80) (0.090 g, 0.282 mmol) and $K_2CO_3$ (0.065 g, 0.470 mmol) were reacted according to GP26 to give the title compound (79KS38-3) (0.059 g, 66%). $^1$H NMR (CDCl$_3$): δ 1.57 (ddd, 1H, J=6.2 Hz, 9.4 Hz, 13.4 Hz), 1.68 (d, 1H, J=17.9 Hz), 1.72-2.00 (m, 6H), 2.03-2.16 (m, 1H), 2.42 (t, 2H, J=6.9 Hz), 2.50 (d, 1H, 17.9 Hz), 2.54-2.63 (m, 2H), 3.28 (td, 1H, J=4.8 Hz, 6.9 Hz), 3.74 (t, 2H, J=6.0 Hz, —CH$_2$CH$_2$CH$_2$OH), 4.40 (t, 2H, J=7.2 Hz, N (from Ar)—CH$_2$CH$_2$CH$_2$—), 6.04 (d, 1H, J=4.5 Hz), 7.10-7.44 (m, 4H, Ar); $^{13}$C NMR (CDCl$_3$) δ 16.2, 26.8, 29.9, 31.6, 33.8, 35.3, 41.3, 45.6, 55.5, 57.0, 62.0, 81.3, 88.5, 111.1, 118.2, 122.7, 123.0, 123.1, 126.4, 136.0, 137.6, 170.2; HPLC-MS (ammonium acetate): [M+H]$^+$=383.30

3.213 3-[3-(3-Propyl-8-aza-bicyclo[3.2.1]oct-8-yl)-propyl]-3H-benzothiazol-2-one (79KS83-2)

8-tertButyloxycarbonyl-3-propyl-8-aza-bicyclo[3.2.1]octane (79KS75) (0.012 g, 0.0474 mmol) was dissolved in DCM (2 mL) followed by the addition of TFA (0.5 mL) under stirring. The mixture was left stirring until complete conversion of the starting material had occurred before it was concentrated in vacuo, basified (2M NaOH), extracted (EtOAc) and concentrated once again. The resultant oil was reacted with 3-(3-Iodopropyl)-3H-benzothiazol-2-one (61KS80) (0.018 g, 0.0569 mmol) and $K_2CO_3$ (0.013 g, 0.0948 mmol) in accordance with GP26 to give the title compound (79KS83-2) (0.011 g, 67%). $^1$H NMR (CDCl$_3$) δ 0.86 (t, 3H, 7.2 Hz, —CH$_2$CH$_2$CH$_3$), 1.10-1.20 (m, 2H), 1.20-1.42 (m, 4H), 1.42-1.50 (m, 2H), 1.50-1.66 (m, 3H), 1.80-1.98 (m, 4H), 2.38-2.50 (m, 2H), 3.05-3.15 (m, 2H), 4.05 (t, 2H, J=6.6 Hz, N(from Ar)—CH$_2$CH$_2$CH$_2$), 7.10-7.44 (m, 4H, Ar); $^{13}$C NMR (CDCl$_3$) δ 14.5, 20.2, 26.8, 27.9, 37.8, 39.4, 41.2, 49.0, 59.8, 111.4, 122.7, 122.9, 123.1, 126.4, 137.7; HPLC-MS (ammonium acetate): [M+H]$^+$= 377.16

3.214 3-[3-(3-Butyl-8-aza-bicyclo[3.2.1]oct-8-yl)-propyl]-3H-benzothiazol-2-one (79KS96-2)

8-tert-Butyloxycarbonyl-3-butyl-8-aza-bicyclo[3.2.1]octane (79KS92) (0.045 g, 0.168 mmol), 3-(3-Iodopropyl)-3H-benzothiazol-2-one (61KS80) (0.064 g, 0.202 mmol) and $K_2CO_3$ (0.046 g, 0.336 mmol) were reacted according to GP26 to give the title compound (79KS96-2) (0.019 g, 32%). $^1$H NMR (CDCl$_3$) δ 0.87 (t, 3H, J=7.2 Hz, —CH$_2$CH$_2$CH$_2$CH$_3$), 1.12-1.64 (m, 13H), 1.80-1.98 (m, 4H), 2.43 (t, 2H, J=6.4 Hz), 3.18 (br s, 2H), 4.05 (t, 2H, J=6.3 Hz, N(from Ar)—CH$_2$CH$_2$CH$_2$), 7.10-7.43 (m, 4H, Ar); $^{13}$C NMR (CDCl$_3$) δ 14.3 (—CH$_2$CH$_2$CH$_2$CH$_3$), 23.1, 26.8, 28.2, 29.4, 36.8, 37.9, 41.2, 49.0, 59.7, 111.4, 122.7, 122.9, 123.1, 126.4, 137.7, 170.2 (C=O); HPLC-MS (ammonium acetate): [M+H]$^+$=359.27

3.215 3-[3-(3-Pentyl-8-aza-bicyclo[3.2.1]oct-8-yl)-propyl]-3H-benzothiazol-2-one (79KS97-oxalate)

3-Pentyl-8-aza-bicyclo[3.2.1]octane (79KS95) (0.118 g, 0.651 mmol), 3-(3-Iodopropyl)-3H-benzothiazol-2-one (61KS80) (0.064 g, 0.781 mmol) and K$_2$CO$_3$ (0.046 g, 1.30 mmol) were reacted according to GP26 to give (79KS97) (0.161 g, 66%). The oxalate salt was prepared by dissolving the product in Et$_2$O and a minimum of MeOH followed by the addition of a solution of oxalic acid (1.1 eq of obtained product) in Et$_2$O. Filtration gave the title compound (79KS97-oxalate). NMR of the free base was recorded. $^1$H NMR (CDCl$_3$); δ 0.88 (t, 3H, J=6.9 Hz, —CH$_2$CH$_2$CH$_2$CH$_2$CH$_3$), 1.17-1.38 (m, 8H), 1.38-1.48 (m, 2H), 1.56-1.75 (m, 3H), 1.86-2.00 (m, 4H), 2.08-2.22 (m, 2H), 2.43 (t, 2H, J=6.7 Hz), 3.18 (br s, 2H), 4.07 (t, 2H, J=6.9 Hz, N(from Ar)—CH$_2$CH$_2$CH$_2$), 7.12-7.43 (m, 4H, Ar); $^{13}$C NMR (CDCl$_3$) δ 14.3 (—CH$_2$CH$_2$CH$_2$CH$_2$CH$_3$), 22.9, 26.9, 27.3, 28.3, 28.5, 32.2, 35.7, 38.6, 41.2, 48.9, 58.9, 111.3, 122.7, 123.0 123.1, 126.4, 137.7, 170.2(C=O); HPLC-MS (ammonium acetate): [M+H]$^+$=373.28

3.216 3-[3-(3-Hexyl-8-aza-bicyclo[3.2.1]oct-8-yl)-propyl]-3H-benzothiazol-2-one (79KS83-8)

8-tertButyloxycarbonyl-3-hexyl-8-aza-bicyclo[3.2.1]octane (79KS81) (0.031 g, 0.105 mmol), 3-(3-Iodopropyl)-3H-benzothiazol-2-one (61KS80) (0.040 g, 0.126 mmol) and K$_2$CO$_3$ (0.029 g, 0.210 mmol) were reacted according to GP26 to give the title compound (79KS83-8) (0.035 g, 86%). $^1$H NMR (CDCl$_3$) δ 0.82-0.94 (t, 3H, J=6.8Hz, —CH$_2$CH$_2$CH$_2$CH$_2$CH$_2$CH$_3$), 1.10-1.37 (m, 12H), 1.40-1.62 (m, 5H), 1.80-1.95 (m, 4H), 2.40 (t, 2H, 6.2 Hz), 3.18 (br s, 2H), 4.04 (t, 2H, J=6.8 Hz, N(from Ar)—CH$_2$CH$_2$CH$_2$), 7.08-7.44 (m, 4H, Ar); $^{13}$C NMR (CDCl$_3$) δ 14.3 (—CH$_2$CH$_2$CH$_2$CH$_2$CH$_2$CH$_3$), 22.9, 26.8, 27.0, 27.1, 28.3, 29.7, 32.1, 37.2, 38.1, 41.3, 49.0, 59.7, 111.3, 122.7, 122.9, 123.1, 126.4, 137.8, 170.2(C=O); HPLC-MS (ammonium acetate): [M+H]$^+$=387.27

3.217 3-[3-(3-Butylidene-8-aza-bicyclo[3.2.1]oct-8-yl)-propyl]-3H-benzothiazol-2-one (61KS91-1)

To a slurry of butylphosphonium bromide (1.70 g, 4.26 mmol) in dry THF (10 mL) was added BuLi (2.66 mL, 1.6M sol., 4.26 mmol) at 0° C. under stirring. The mixture was allowed to reach room temperature and stirred for another 2 h before dropwise addition of a solution of N-Boc-nortropinone (0.960 g, 4.26 mmol) in dry THF (5 mL) at 0° C. The reaction mixture was slowly heated to room temperature and thereafter left stirring overnight. The resultant heterogeneous mixture was filtered and concentration in vacuo followed by column chromatography in DCM to yield the bicyclic amine 32HS95 (0.032 g, 3%). This was then dissolved in DCM/TFA (1:1, 2 mL) and concentrated. To the resultant syrup was added 2M NaOH (5 mL) and the mixture was extracted (DCM). The combined organic phase was dried (Na$_2$SO$_4$), filtered and concentrated. This product was reacted with 3-(3-Iodopropyl)-3H-benzothiazol-2-one (61KS80) (0.046 g, 0.145 mmol) and K$_2$CO$_3$ (0.033 g, 0.242 mmol) according to GP26 to give the title compound (61KS91-1) (0.025 g, 58%). $^1$H NMR (CDCl$_3$) δ 0.88 (t, 3H, J=7.2 Hz, =CHCH$_2$CH$_2$CH$_3$), 1.35 (sixt, 2H, J=7.2 Hz, =CHCH$_2$CH$_2$CH$_3$), 1.43 (t, 1H, J=8.6 Hz), 1.55 (t, 1H, J=8.6 Hz), 1.76-1.92 (m, 5H), 1.97 (quint, 2H, J=7.2 Hz), 2.22 (d, 1H, J=14.4 Hz), 2.27 (d, 1H, J=14.4 Hz), 2.50-2.64 (m, 3H), 3.24-3.35 (m, 2H), 4.01 (t, 2H, 7.0 Hz, N(from Ar)—CH$_2$CH$_2$CH$_2$), 5.22 (t, 1H, J=7.4 Hz), 7.20-7.42 (m, 4H, Ar); HPLC-MS (ammonium acetate): [M+H]$^+$=357.40

3.218 3-[3-(4-Methoxymethyl-piperidine-1-yl)-propyl]-3H-benzothiazol-2-one (61KS89-oxalate)

To a solution of 1-tertButyloxycarbonyl-4-methoxymethyl-piperidine (61KS83) (0.088 g, 0.385 mmol) in DCM (2 mL) was added TFA (2 mL) under stirring. After complete conversion of the starting material the mixture was basified (2M NaOH) and extracted with DCM. After drying (Na$_2$SO$_4$) of the combined organic phase, filtering and concentration, the crude product was reacted with 3-(3-Iodopropyl)-3H-benzothiazol-2-one (61KS80) (0.147 g, 0.462 mmol) and K$_2$CO$_3$ (0.106 g, 0.770 mmol) to give the title compound (61KS89) (0.086 g, 67%). The oxalate salt was prepared by dissolving the product in Et$_2$O and a minimum of MeOH followed by the addition of a solution of oxalic acid (1.1 eq of obtained product) in Et$_2$O. Filtration gave the title compound (61KS89-oxalate). NMR of the free base was recorded. $^1$H NMR (CDCl$_3$) δ 1.23 (dq, 2H, J=3.9 Hz, 12.1 Hz), 1.48-1.63 (m, 1H), 1.64-1.73 (m, 2H), 1.83-1.95 (m, 4H), 2.35 (t, 2H, J=6.9 Hz), 2.84 (m, 2H, J=11.8 Hz), 3.19 (d, 2H, J=7.2 Hz, —CH$_2$OCH$_3$), 3.30 (s, 3H, —CH$_2$OCH$_3$), 3.97 (t, 2H, J=7.2 Hz, N(from Ar)—CH$_2$CH$_2$CH$_2$), 7.07-7.40 (m, 4H, Ar); $^{13}$C NMR (CDCl$_3$): δ 25.3, 29.5, 36.4, 41.3, 53.7, 55.7, 59.0, 78.2 (—CH$_2$OCH$_3$), 111.0, 122.7, 123.0, 123.1, 126.4, 137.6, 170.1 (C=O); HPLC-MS (ammonium acetate): [M+H]$^+$=321.36

3.219 3-[3-(4-Ethoxymethyl-piperidine-1-yl)-propyl]-3H-benzothiazol-2-one (61KS91-3-oxalate)

To a solution of 1-tertButyloxycarbonyl-4-ethoxymethyl-piperidine (61KS90) (0.071 g, 0.292 mmol) in DCM (2 mL) was added TFA (2 mL) under stirring. After complete conversion of the starting material the mixture was basified (2M NaOH) and extracted with DCM. After drying (Na$_2$SO$_4$) of the combined organic phase, filtering and concentration, the crude product was reacted with 3-(3-Iodopropyl)-3H-benzothiazol-2-one (61KS80) (0.112 g, 0.350 mmol) and K$_2$CO$_3$ (0.067 g, 0.484 mmol) according to GP26 to give the title compound (61KS91-3) (0.048 g, 49%). The oxalate salt was prepared by dissolving the product in Et$_2$O and a minimum of MeOH followed by the addition of a solution of oxalic acid (1.1 eq of obtained product) in Et$_2$O. Filtration gave the title compound (61KS91-3-oxalate). NMR of the free base was recorded. $^1$H NMR (CDCl$_3$) δ 1.16 (t, 3H, J=7.0 Hz, —CH$_2$OCH$_2$CH$_3$), 1.41 (dq, 2H, J=4.2 Hz, 12.6 Hz), 1.56-170 (m, 1H), 1.74-1.82 (m, 2H), 2.05 (quint, 2H, J=7.0 Hz, N(from Ar)—CH$_2$CH$_2$CH$_2$), 2.13 (td, 2H, J=2.8 Hz, 11.8 Hz), 2.57 (t, 2H, J=7.0 Hz, N(from Ar)—CH$_2$CH$_2$CH$_2$), 3.04 (m, 2H, 2H, J=6.2 Hz, —CH$_2$OCH$_2$CH$_3$), 3.43 (q, 2H, J=7.0 Hz, —CH$_2$OCH$_2$CH$_3$), 4.00 (t, 2H, J=7.0 Hz, N(from Ar)—CH$_2$CH$_2$CH$_2$), 7.10-7.40 (m, 4H, Ar); HPLC-MS (ammonium acetate): [M+H]$^+$=335.39

3.220 3-{3-[4-(2-Methoxyethyl)-piperidine-1-yl]-propyl}-3H-benzothiazol-2-one (61KS91-2-oxalate)

To a solution of 1-tertButyloxycarbonyl-4-(2-methoxyethyl)-piperidine (61KS86) (0.100 g, 0.410 mmol) in DCM (2 mL) was added TFA (2 mL) under stirring. After complete conversion of the starting material the mixture was basified (2M NaOH) and extracted with DCM. After drying (Na$_2$SO$_4$) of the combined organic phase, filtering and concentration, the crude product was reacted with 3-(3-Iodopropyl)-3H-benzothiazol-2-one (61KS80) (0.157 g, 0.492 mmol) and K$_2$CO$_3$ (0.113 g, 0.820 mmol) according to GP26 to give the title compound (0.089 g, 65%). The oxalate salt was prepared by dissolving the product in Et$_2$O and a minimum of MeOH followed by the addition of a solution of oxalic acid (1.1 eq of obtained product) in Et$_2$O. Filtration gave the title compound (61KS91-2-oxalate). NMR of the free base was recorded. $^1$H NMR (CDCl$_3$) δ 1.23 (dq, 2H, J=12.1 Hz), 1.31-1.43 (m, 1H), 1.49 (q, 2H, J=6.3 Hz, —CH$_2$CH$_2$OCH$_3$), 1.62-1.70 (m, 2H), J=12.0 Hz), (m, 4H), 2.37 (t, 2H, J=7.3 Hz, N(from Ar)—CH$_2$CH$_2$CH$_2$), 2.80-2.88 (m, 2H), 1.85-1.96 3.30 (s, 3H, —CH$_2$CH$_2$OCH$_3$), 3.38 (t, 2H, J=6.3 Hz, —CH$_2$CH$_2$OCH$_3$), 3.98 (t, 2H, J=7.3 Hz, N(from Ar)—CH$_2$CH$_2$CH$_2$), 7.08-7.40 (m, 4H, Ar); HPLC-MS (ammonium acetate): [M+H]$^+$=335.39

3.221 General Method 27 (GP27)

To a solution of a Boc-protected amine (1.0 eq) in DCM (2 mL) was added TFA (2 mL) followed by concentration in vacuo. The remaining syrup was dissolved in MeCN (3 mL) followed by addition of 3-(3-Chloropropyl)-3H-benzothiazol-2-one (61KS67) (0.046 g, 0.204 mmol, 1.3 equiv), NaI (0.031 g, 0.204 mmol, 1.3 equiv) and Na$_2$CO$_3$ (0.083 g, 0.7.85 mmol, 5 eq). The reaction mixture was shaken at 80° C. for 18 h. Excess cyclohexyl isocyanate (4.0 equiv) was added and shaking at 80° C. was continued for another 30 min before the reaction mixture was put on an ionexchange column (Varian BondElut®-SCX, H$^+$) and eluted with 2.5% NH$_4$OH in MeOH. Evaporation of the solvent gave the desired product. This was taken up in Et$_2$O and a solution of oxalic acid (1.1 equiv) in Et$_2$O was added. The white precipitate was filtered off and dried. NMR spectra of the free bases were recorded.

3.222 3-{3-[4-(Prop-2-ene-1-oxy)-piperidin-1-yl]-propyl}-3H-benzothiazol-2-one (61KS69-oxalate).

1-tert-Butyloxycarbonyl-4-(prop-2-ene-1-oxy)-piperidine (104KS20) (0.038 g, 0.157 mmol) was reacted according to GP27 to give the title compound (61KS69-oxalate) (0.040 g, 77%). $^1$H NMR (CDCl$_3$) δ 1.54-1.65 (m, 2H), 1.80-1.94 (m, 5H), 2.06 (td, J=2.0 Hz, 11 Hz), 2.36 (t, 2H, 7.0 Hz), 2.66-2.75 (m, 2H), 3.34 (sept, 1H, J=4.3 Hz), 3.96 -4.04 (m, 4H), 5.14 (ddt, 1H, J=1.5 Hz, J=11 Hz, —OCH$_2$CH=CH$_c$H$_t$), 5.26 (ddt, 1H, J=1.8 Hz, 17.6 Hz, —OCH$_2$CH=CH$_c$H$_t$), 5.91 (ddt, 1H, J=5.5 Hz, 11 Hz, 17.6 Hz, —OCH$_2$CH=CH$_c$H$_t$), 7.10-7.42 (m, 4H, Ar); $^{13}$C NMR (CDCl$_3$) δ 25.4, 31.7, 41.2, 51.5, 55.2, 69.0 and 74.8 (C4 and —O CH$_2$CH=CH$_c$H$_t$), 111.0, 116.7, 122.8, 123.0, 123.1, 126.4, 135.6, 137.6 (Ar), 170.2 (C=O). HPLC-MS (ammonium acetate): [M+H]$^+$=333.35

3.223 3-[3-(4-Propoxy-piperidin-1-yl)-propyl]-3H-benzothiazol-2-one (61KS70-1-oxalate)

1-tert-Butyloxycarbonyl-4-propoxy-piperidine (104KS21) (0.049 g, 0.200 mmol) was reacted according to GP27 to give the title compound (61KS70-1-oxalate) (0.056 g, 80%). $^1$H NMR (CDCl$_3$) δ 0.90 (t, 3H, J=7.1 Hz, —OCH$_2$CH$_2$CH$_3$), 1.50-1.63 (m, 4H), 1.82-1.95 (m, 4H), 2.06 (td, 2H, J=2.4 Hz, 10.8 Hz), 2.35 (t, 2H, J=6.8 Hz), 2.70 (dt, 2H, J=4.8 Hz, 8.0 Hz), 3.26 (sept, 1H, J=4.3 Hz), 3.37 (t, 2H, J=6.8 Hz), 3.99 (t, 2H, J=7.0 Hz), 7.09-7.42 (m, 4H, Ar); $^{13}$C NMR (CDCl$_3$) δ 10.9 (—OCH$_2$CH$_2$CH$_3$), 23.5, 25.3, 31.4, 41.1, 51.4, 55.2, 69.8 and 74.9 (—OCH$_2$CH$_2$CH$_3$ and C4), 111.1, 122.8, 122.9, 123.2, 126.5, 137.5 (Ar), 170.3 (C=O). HPLC-MS (ammonium acetate): [M+H]$^+$=335.37

3.224 3-[3-(4-Isobutoxy-piperidin-1-yl)-propyl]-3H-benzothiazol-2-one (61KS70-2-oxalate)

1-tert-Butyloxycarbonyl-4-(isobutoxy)-piperidine (61KS66) (0.051 g, 0.200 mmol) was reacted according to GP27 to give the title compound (61KS70-2-oxalate) (0.059 g, 85%). $^1$H NMR (CDCl$_3$) δ 0.89 (d, 6H, J=6.6 Hz, —OCH$_2$CH(CH$_3$)$_3$), 1.52-1.63 (m, 2H), 1.81 (nonet, 1H, J=6.9 Hz, —OCH$_2$CH(CH$_3$)$_3$), 1.82-1.89 (m, 2H), 1.90 (quint, 2H, 7.0 Hz, N(from Ar)—CH$_2$CH$_2$CH$_2$—), 2.65 (td, 2H, J=2.3 Hz, 10.9 Hz), 2.35 (t, 2H, J=7.0 Hz, N(from Ar)—CH$_2$CH$_2$CH$_2$—), 2.68 (m, 2H), 3.17 (d, 2H, J=6.9 Hz, —OCH$_2$CH(CH$_3$)$_3$), 3.20-3.28 (m, 1H), 3.99 (t, 2H, J=7.0 Hz, N(from Ar)—CH$_2$CH$_2$CH$_2$—), 7.10-7.42 (m, 4H, Ar); $^{13}$C NMR (CDCl$_3$) δ 19.7 (—OCH$_2$CH(CH$_3$)$_3$), 25.5, 29.0, 31.7, 41.2, 51.5, 55.3, 75.1 and 75.2 (C4 and —O CH$_2$CH(CH$_3$)$_3$), 111.0, 122.7, 123.0, 123.1, 126.4, 137.7 (Ar), 170.1 (C=O); HPLC-MS (ammonium acetate): [M+H]$^+$=349.1

3.225 3-[3-(4-Cyclobutylmethoxy-piperidin-1-yl)-propyl]-3H-benzothiazol-2-one (61KS 70-3-oxalate)

1-tert-Butyloxycarbonyl-4-(cyclobutylmethoxy)-piperidine (61KS51) (0.054 g, 0.200 mmol) was reacted according to GP27 to give the title compound (61KS70-3-oxalate) (0.044 g, 61%). $^1$H NMR (CDCl$_3$) δ 1.53-1.64 (m, 2H), 1.64-1.75 (m, 2H), 1.78-1.97 (m, 5H), 1.98-2.20 (m, 3H), 2.39 (t, 2H, J=6.9 Hz), 2.52 (sept, 1H, J=7.4 Hz, —OCH$_2$CH(CH$_2$CH$_2$CH$_2$)), 2.67-2.76 (m, 2H), 3.22-3.30 (m, 1H), 3.39 (d, 2H, J=7.4 Hz, —OCH$_2$CH(CH$_2$CH$_2$CH$_2$), 3.99 (t, 2H, J=6.9 Hz), 7.09-7.41 (m, 4H, Ar); $^{13}$C NMR (CDCl$_3$) δ 18.8 (—OCH$_2$CH(CH$_2$CH$_2$CH$_2$)), 25.3 (—OCH$_2$CH(CH$_2$CH$_2$CH$_2$)), 31.4, 34.2, 35.6, 41.2, 51.4, 55.2, 72.8 and 74.9 (—OCH$_2$CH(CH$_2$CH$_2$CH$_2$) and C4), 111.1, 122.7, 122.9, 123.2, 126.4, 137.6 (Ar), 170.2 (C=O).

3.226 1-[3-(1,5-Dioxa-9-azaspiro[5.5]undec-9-yl)propyl]-1,3-dihydrobenzoimidazol-2-one (45NK66)

The reaction was carried out according to GP20 using 1,5-dioxa-9-azaspiro[5.5]undecane (59 mg, 0.5 mmol). The product was purified using an Isco CombiFlash Sq 16× (4.1 g silica column, eluting CH$_2$Cl$_2$ (5 min), 0-15% methanol in CH$_2$Cl$_2$ (20 min), 15% methanol in CH$_2$Cl$_2$ (15 min)). Methanol (2 mL) and HCl in ether (2 M, 0.2 mL) were added, the solution concentrated to give the title compound as the hydrochloride salt (14 mg).

$^1$H NMR (CD$_3$OD) δ 1.67 (tt, 2H), 1.92 (m, 4H), 1.95 (tt, 2H), 2.46 (m, 6H), 3.87 (t, 4H), 3.92 (t, 2H), 7.07 (m, 3H), 7.17 (m, 1H); LC-MS [M+H]$^+$ 332.2 (cald. 332.2).

3.227 1-(3-[4-Butylpiperidino]propyl)-1,3-dihydrobenzimidazol-2-one (61KS19)

1-(3-chloropropyl)-1,3-dihydro-2H-benzimidazole-2-one (7.23 g, 34.3 mmol), 4-butylpiperidine (3.73 g, 26.4 mmol), NaI (5.14 g, 34.3 mmol) and Na$_2$CO$_3$ (3.64 g, 34.3 mmol) was suspended in CH$_3$CN (200 mL) and refluxed for 3 h and then cooled to room temperature. Water (100 mL) was added followed by extraction (EtOAc), drying (MgSO$_4$), filtration and concentration in vacuo. The crude product was purified by column chromatography [SiO$_2$, EtOAc/MeOH/NH$_4$OH (85:10:5) followed by SiO$_2$, dichloromethane/MeOH (95:5) (R$_f$(3)=0.21)] to give the titled compound (6.26 g, 75%) as a colorless oil, which was converted into the corresponding oxalate salt.

$^1$H-NMR (amine, CDCl$_3$) δ 0.88 (t, 3H, J=6.9 Hz), 1.34-1.14 (m, 9H), 1.65 (d, 2H, J=9.2 Hz), 1.86 (t, 2H, J=10.7 Hz), 1.97 (quint, 2H, J=7.3 Hz), 2.38 (t, 2H, J=7.6 Hz), 2.86 (d, 2H, J=10.7 Hz), 3.84 (t, 2H, J=7.3 Hz), 7.10-7.00 (m, 4H), 10.2 (br s, 1H).

3.228 4-(3-Methylbutylidene)piperidine hydrochloride (18HS64)

Isoamyltriphenylphosphonium bromide (25.0 g, 60.5 mmol) was suspended in anhydrous THF (130 ml) and cooled to 0° C. n-BuLi was added drop wise over a 1-1.5 h period. The resulting mixture was stirred at room temperature for 2 h. Boc-4-piperidone (12.05 g, 60.5 mmol) was dissolved in anhydrous THF (25 ml) and added in small portions at 30° C. The mixture was left with stirring over night at 30° C. The reaction mixture was cooled to room temperature. The precipitated triphenylphosphine oxide was filtered off and the crude product was concentrated in vacuo. The crude residue was purified by column chromatography ($SiO_2$, dichloromethane). Treatment with 2N HCl in dioxane gave the title compound in 60% yield.

$^1$H NMR ($CDCl_3$) δ 0.85 (d, 6H), 1.57 (n, 1H), 1.86 (t, 2H), 2.49-2.56 (m, 4H), 3.12-3.20 (m, 4H), 5.32 (t, 1H), 9.64 (br s, 2H); $^{13}$C NMR ($CDCl_3$) δ 22.4, 25.2, 28.8, 32.7, 36.5, 45.1, 45.9, 126.2, 130.4.

3.229    1-tert-Butoxycarbonyl-4-butylidenepiperidine (61KS6)

To a slurry of butylphosphonium bromide (748 mg, 1.8 mmol) in dry diethyl ether (10 mL) was added BuLi (1.1 mL, 1.6 M solution, 1.8 mmol) at 0° C. over a period of 5 min. The cooling was removed and the reaction mixture was left stirring for 1 h. A solution of 1-tert-butoxycarbonyl-4-piperidone (300 mg, 1.5 mmol) in dry diethyl ether (5 mL) was carefully added and the stirring was continued for 3 h at room temperature. The reaction was quenched by the addition of water (10 mL) followed by extraction (diethyl ether), drying ($MgSO_4$), filtration and concentration in vacuo. The crude product was purified by column chromatography ($SiO_2$, ethyl acetate/heptane (1:6) Rf=0.47) to give the title compound (253 mg) as a colorless oil.

$^1$H NMR ($CDCl_3$) δ 0.87 (t, 3H, J=7.0 Hz), 1.34 (2H, J=7.0 Hz), 1.45 (s, 9H), 1.96 (dt, 2H, J=7.0 Hz), 2.10 (t, 2H, J=6.2 Hz), 2.18 (t, 2H, J=6.2 Hz), 3.36 (dt, 4H, J=6.2 Hz), 5.20 (t, 1H, J=7.0 Hz); $^{13}$C NMR ($CDCl_3$) δ 13.9, 23.3, 28.5, 28.7, 29.3, 36.1, 79.5, 124.2, 135.2, 155.0.

3.230    1-tert-Butoxycarbonyl-4-pentylidenepiperidine (61KS7)

The reaction was carried out according to the method used for the preparation of 6]KS-6 using pentylphosphonium bromide to give 50% of the title compound.

$^1$H NMR ($CDCl_3$) δ 0.89 (t, 3H, J=6.9 Hz), 1.36-1.24 (m, 4H), 1.46 (s, 9H), 2.12 (t, 2H, J=6.2 Hz), 2.19 (t, 2H, J=6.2 Hz), 3.38 (dt, 4H, J=6.2 Hz), 5.20 (t, 1H, J=7.1 Hz); $^{13}$C NMR ($CDCl_3$) δ 14.2, 22.5, 27.0, 28.5, 28.7, 32.4, 36.1, 79.6, 124.4, 135.0, 155.1.

3.231    1-(3-[4-Butylidenepiperidino]propyl)-1,3-dihydrobenzimidazol-2-one (61KS12)

1-tert-Butoxycarbonyl-4-butylidenepiperidine (49 mg, 0.2 mmol) was dissolved in trifluoroacetic acid (2 mL) and left stirring at room temperature for 5 min followed by concentration in vacuo. The resultant syrup was dissolved in acetonitrile (5 mL) and 1-(3-chloropropyl)1,3-dihydro-2H-benzimidazole-2-one (58 mg, 0.28 mmol), sodium iodide (41 mg, 0.28 mmol) and $Na_2CO_3$ (56 mg, 0.53 mmol) was added and shaken for 3 days at 80° C. Water (5 mL) was added followed by extraction (ethyl acetate), drying ($MgSO_4$), filtration and concentration. The crude product was purified by column chromatography [$SiO_2$, ethyl acetate/methanol/ammonium hydroxide (85:10:5) ($R_f$ 0.52) followed by $SiO_2$, dichloromethane/methanol (95:5) ($R_f$ 0.21)] to give the title compound (26 mg) as a colorless oil.

$^1$H NMR ($CDCl_3$) δ 0.88 (t, 3H, J=7.3 Hz), 1.34 (sext, 2H, J=7.3 Hz), 2.03-1.91 (m, 4H), 2.18 (t, 2H, J=5.6 Hz), 2.24 (t, 2H, J=5.6 Hz), 2.46-2.35 (m, 6H), 3.97 (t, 2H, J=6.7 Hz), 5.12 (t, 1H, J=7.3 Hz), 7.15-7.00 (m, 4H), 10.3 (br s, 1H); $^{13}$C NMR ($CDCl_3$) δ 13.9, 23.4, 26.1, 28.4, 29.4, 36.2, 39.3, 54.9, 55.5, 55.7, 108.2, 109.8, 121.3, 121.5, 122.8, 128.3, 130.8, 136.2, 156.0.

3.232    1-(3-f4-Pentylidenepiperidino]propyl)-1,3-dihydrobenzimidazole-2-one (61KS13)

The reaction was carried out according to the method used for the preparation of 61KS12 using 1-tert-butoxycarbonyl-4-pentylidenepiperidine (49 mg, 0.2 mmol) to give 60% of the title compound.

$^1$H NMR ($CDCl_3$) δ 0.88 (t, 3H, J=6.7 Hz), 1.38-1.23 (m, 4H), 2.04-1.90 (m, 4H), 217 (t, 2H, J=5.5 Hz), 2.24 (t, 2H, J=5.5 Hz), 2.44-2.33 (m, 6H), 3.96 (t, 2H, J=5.5 Hz), 5.12 (t, 1H, J=7.3 Hz), 7.15-6.95 (m, 4H), 10.2 (br s, 1H); $^{13}$C NMR ($CDCl_3$) δ 14.2, 22.5, 26.1, 27.0, 28.4, 32.5, 36.2, 39.3, 54.9, 55.5, 55.7, 108.3, 109.8, 121.3, 121.5, 123.0, 128.3, 130.8, 136.0, 155.9.

3.233 3-[3-(4-Butylpiperidin-1-yl)propyl]-3H-benzothiazol-2-one (56NK34)

A 25 ml round bottomed flask was charged with 3H-benzothiazole-2-one (151 mg, 1.0 mmol) and a stirring bar then evacuated and put under argon. THF (5 mL) was added followed by sodium hydride (48 mg of 60% suspension in oil, 1.2 mmol) and the reaction was stirred at 0° C. for 90 min. 1-Chloro-3-iodopropane (129 μL, 1.2 mmol) was added and the reaction was stirred for 18 h at room temperature. Water (2 mL) was added and the product was extracted into ethyl acetate (2×10 mL). The organic layer was dried ($K_2CO_3$), filtered and concentrated in vacuo before being purified by using an Isco CombiFlash Sq 16× (4.1 g silica column, eluting 0-35% ethyl acetate in heptanes (30 min) then 35% ethyl acetate in heptanes (12 min)) to give a 1:1 mixture of 3-(3-chloro-propyl)-3H-benzothiazol-2-one and 3-allyl-3H-benzothiazole-2-one (121 mg). A 7 mL vial was charged with the mixture, 4-butyl-piperidine (75 mg, 0.53 mmol), sodium iodide (159 mg, 1.06 mmol), sodium carbonate (112 mg, 1.06 mmol) and acetonitrile (2 mL) and shaken at 80° C. for 18 h. The reaction was cooled to room temperature and water (2 mL) was added. The product was extracted into ethyl acetate (2×5 mL), the organic layer was dried ($K_2CO_3$), filtered and concentrated in vacuo before being purified by using an Isco CombiFlash Sq 16× [4.1 g silica column, eluting 0-20% 2-propanol in $CH_2Cl_2$ (25 min) then 20% 2-propanol in $CH_2Cl_2$ (30 min)] to give the title compound (26 mg).

$^1$H NMR ($CDCl_3$) δ 0.89 (t, 3H), 1.16-1.33 (m, 9H), 1.68 (m, 2H), 1.97 (m, 4H), 2.42 (t, 2H), 2.90 (br. d, 2H), 4.01 (t, 2H), 7.12-7.20 (m, 2H), 7.30 (m, 1H), 7.41 (m, 1H).

3.234 2-(3-Chloropropylthio)benzoxazole (62KK004)

Sodium hydride (0.132 g, 3.3 mmol, 60% in mineral oil) was added in portions to a stirred solution of 2-mercaptobenzoxazole (0.500 g, 3.3 mmol) in dry THF (10 ml) under argon at 0° C. After complete addition the mixture was stirred at room temperature for 1.5 h. A solution of 3-chloro-1-iodopropane (0.677 g, 3.31 mmol) in dry THF (1 ml) was added dropwise and the mixture stirred at room temperature for 24 h. Water was poured into the reaction mixture, and the aqueous mixture was extracted with dichloromethane. The combined organic phases was dried ($K_2CO_3$), filtered and concentrated to give 0.71 g of a brown oil. The oil was purified by flash chromatography on silica gel using n-heptane and dichloromethane (2/1 and 1/1) as eluent to give 0.604 g of the title compound as a colorless oil.

$^1$H NMR ($CDCl_3$) δ 2.37-2.31 (m, $CH_2$), 3.46 (t, J=7, $CH_2$), 3.72 (t, J=6, $CH_2$), 7.30-7.21 (m, 2H), 7.45-7.42 (m,

1H), 7.61-7.58 (m, 1H); $^{13}$C NMR (CDCl$_3$ δ 29.5, 32.1, 43.2, 110.1, 118.7, 124.2, 124.6, 142.1, 152.1, 164.5. MS: 227 (MH$^+$).

3.235 2-(3-Chloropropylthio)benzothiazole (62KK005)

The reaction was carried out according to the method used for the preparation of 62KK004 using 2-mercaptobenzothiazole (0.12 g, 3.0 mmol) to give 76% of the title compound. The crude oil was purified by flash chromatography on silica gel using n-heptane and CH$_2$Cl$_2$ (1/1) as eluent to give 0.552 g of the title compound as a colorless oil.

$^1$H-NMR (CDCl$_3$) δ 2.36-2.29 (m, CH$_2$), 3.51 (t, J=7, CH$_2$), 3.71 (t, J=6, CH$_2$), 7.32-7.26 (m, 1 H), 7.43-7.39 (m, 1 H), 7.76-7.74 (m, 1 H), 7.88-7.85 (m, 1 H); $^{13}$C-NMR (CDCl$_3$) δ 30.7, 32.2, 43.4, 121.2, 121.8, 124.6, 126.3, 135.5, 153.5, 166.3: MS: 244 (MH$^+$).

3.236 2-(2-Chloroethylthio)benzoxazole (56NK27)

Sodium hydride (0.048 g, 1.2 mmol, 60% in mineral oil) was added in portions to a stirred solution of 2-mercaptobenzoxazole (0.151 g, 1.00 mmol) in dry THF (5 ml) under argon at 0° C. After complete addition the mixture was stirred at room temperature for 1.5 h. A solution of 3-chloro-1-iodoethane (0.228 g, 1.2 mmol) was added and the mixture stirred at room temperature for 24 h. Water was poured into the reaction mixture, and the aqueous mixture was extracted with dichloromethane. The combined organic phases was dried (K$_2$CO$_3$), filtered and concentrated to give 0.101 g of the title compound as an oil.

$^1$N-NMR (CDCl$_3$) δ 3.63 (t, J=7, CH$_2$), 3.93 (t, J=7, CH$_2$), 7.32-7.23 (m, 2 H), 7.46-7.43 (m, 1 H), 7.61-7.59 (m, 1 H).

3.237 2-[3-(4-Butyl-1-piperidinyl)propylthio]benzoxazole (62KK034)

A 7 mL vial was charged with 4-butylpiperidine (0.028 g, 0.20 mmol), 2-(3-chloropropylthio)benzoxazole (0.050 g, 0.22 mmol), sodium iodide (0.035 g, 0.23 mmol), and K$_2$CO$_3$ (0.030 g, 0.22 mmol) and 1 ml acetonitrile and shaken at 50° C. for 18 h. Water was added and the aqueous mixture was extracted with dichloromethane. The combined organic phases was filtered through a polytetrafluoroethylene membrane and then concentrated to give 0.064 g of a crude oil. Dichloromethane (2 ml) and PS-Isocyanate (1.0-1.5 mmol/g) resin (0.050 g) were added and the resulting mixture was left at room temperature for 2 h and then filtered. The resin was washed with dichloromethane, and the combined organic phases was concentrated to give 0.051 g oil. The oil was dissolved in methanol and loaded onto a Varian SCX ion exchange column. The column was washed with methanol (2 column volumes) then the product was eluted off the column using 10% ammonium hydroxide in methanol (2 column volumes). The solute was concentrated to give the title compound (0.021 g) as a colorless oil.

$^1$H-NMR (CDCl$_3$) δ 0.88 (t, J=7 Hz, CH$_3$), 1.31-1.21 (m, 9 H), 1.67-1.64 (m, 2 H), 1.88-1.88 (m, 2 H), 2.06-1.99 (m, CH$_2$), 2.47 (t, J=7 Hz, CH$_2$), 2.91-2.88 (m, 2 H), 3.35 (t, J=7 Hz, CH$_2$), 7.29-7.20 (m, 2 H), 7.43-7.41 (m, 1 H), 7.59-7.57 (M, 1 H); $^{13}$C-NMR (CDCl$_3$) δ 14.3, 23.1, 27.0, 29.2, 30.7, 32.7, 36.0, 36.5, 54.3, 57.6, 110.0, 118.6, 123.9, 124.4, 142.3, 152.1, 165.4. MS: 333 (MH$^+$).

3.238 2-[3-(4-butyl-1-piperidinyl)propylthio]benzothiazole (62KK003)

A 7 mL vial was charged with 4-butylpiperidine (0.028 g, 0.20 mmol), 2-(3-chloropropylthio)benzothiazole (0.054 g, 0.22 mmol), sodium iodide (0.034 g, 0.23 mmol), K$_2$CO$_3$ (0.031 g, 0.22 mmol) and acetonitrile (2 ml) and shaken at 82° C. for 20 h. Water was added and the aqueous mixture was extracted with dichloromethane. The combined organic phases was dried (K$_2$CO$_3$), filtered and concentrated to give 0.068 g of a crude oil. The crude oil (0.040 g) was purified with preparative RP-HPLC [SYNARGI 60 mm×21.2 mm. 20 ml/min, gradient acetonitrile/H$_2$O (10 mM ammonium acetate)] to afford 0.016 g of the title compound as a colorless oil.

$^1$H-NMR (CDCl$_3$) δ 0.81 (t, J=7, CH$_3$), 1.22-1.14 (m, 9 H), 1.60-1.57 (m, 2 H), 1.86-1.80 (m, 2 H), 1.98-1.91 (m, CH$_2$), 2.40 (t, J=7, CH$_2$), 2.84-2.81 (m, 2 H), 3.31 (t, J=7, CH$_2$), 7.23-7.19 (m, 1 H), 7.35-7.31 (m, 1 H), 7.68-7.66 (m, 1 H), 7.79-7.77 (m, 1 H); MS: 349 (MH$^+$).

3.239 2-[2-(4-butyl-1-piperidinyl)ethylthio]benzoxazole (62KK004)

The reaction was carried out according to the method used for the preparation of 62KK003 using crude 2-(2-chloroethylthio)-benzoxazole (0.098 g) to give 0.034 g of the title compound as a colorless oil.

$^1$H-NMR (CDCl$_3$) 0.81 (t, J=7, CH$_3$), 1.22-1.14 (m, 9 H), 1.60-1.58 (m, 2 H), 1.97-1.92 (m, 2 H), 2.69 (t, J=7, CH$_2$), 2.89-2.86 (m, 2 H), 3.39 (t, J=7, CH$_2$), 7.21-7.12 (m, 2H), 7.36-7.33 (m, 1 H), 7.52-7.50 (m, 1 H); $^{13}$C-NMR (CDCl$_3$) δ 14.3, 23.1, 29.2, 30.5, 32.6, 35.9, 36.5, 54.1, 57.6, 110.0, 118.6, 123.9, 124.4, 142.3, 152.1, 165.6; MS: 319 (MH$^+$).

What is claimed is:

1. A compound of Formula I

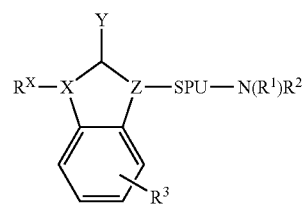

or a pharmaceutically acceptable salt or prodrug thereof, wherein:

X is selected from the group consisting of C$\underline{H}$, O, N and S;

Z is selected from the group consisting of CH and N;

Y is selected from the group consisting of =O, =N$\underline{H}$ and =S or tautomers thereof;

—SPU— is a biradical selected from the group consisting of —(CR$^6$R$^7$)$_n$—A— and —C$_{3-8}$-cycloalkyl-, wherein n is 1, 2, 3, 4, or 5;

A is absent or an optionally substituted —C$_{3-8}$-cycloalkyl;

N together with R$^1$ and R$^2$ form a heterocyclic ring wherein said heterocyclic ring is 8-azabicyclo[3.2.1] octane, wherein the heterocyclic ring is substituted with one or more substituents R$^4$ selected from the group consisting of halogen, C$_{1-8}$-alkyl, C$_{3-8}$-cycloalkyl, C$_{1-8}$-alkoxy, C$_{1-8}$-alkylcarbonyl, C$_{1-8}$-alkylidene, C$_{2-8}$-alkenyl, C$_{2-8}$-alkynyl, C$_{1-6}$-alkyloxyimino, and C$_{1-6}$-alkyloxyamino each of which may be optionally substituted with a substituent R$^5$, and wherein at least one of said substituents R$^4$ is R$^{4t}$ selected from the group consisting of C$_{1-8}$-alkyl, C$_{3-8}$-cycloalkyl, C$_{1-8}$-alkoxy, C$_{1-8}$-alkylcarbonyl, C$_{1-8}$-alkylidene, each of which may be optionally substituted with a substituent R$^5$;

R$^5$ is selected from the group consisting of hydrogen, halogen, hydroxy, C$_{1-8}$-alkyl, C$_{1-8}$-alkoxy, C$_{3-8}$-cycloalkyl, $C_{3-8}$-heterocyclyl, $C_{1-8}$-alkylcarbonyl, $C_{1-8}$-alkylidene, $C_{2-8}$-alkenyl and $C_{2-8}$-alkynyl;

$R^x$ may be absent or selected from the group consisting of hydrogen, optionally substituted $C_{1-8}$-alkyl, optionally substituted $C_{3-8}$-cycloalkyl, optionally substituted $C_{2-8}$-alkenyl, optionally substituted $C_{2-8}$-alkynyl, $CH_2$—$N(R^5)(R^5)$, $CH_2$—$OR^5$, $CH_2$—$SR^5$, and $CH_2$—$O$—$C(=O)R^5$;

$R^3$ may be present 0-4 times and selected from the group consisting of halogen, hydroxy, optionally substituted $C_{1-8}$-alkyl, $C_{1-8}$-alkoxy, optionally substituted $C_{1-8}$-alkylidene, optionally substituted $C_{2-8}$-alkenyl, optionally substituted $C_{2-8}$-alkynyl, optionally substituted aryl, optionally substituted heteroaryl, optionally substituted $C_{3-8}$-cycloalkyl, optionally substituted $C_{3-8}$-heterocyclyl, and optionally substituted $C_{1-8}$-alkylcarbonyl; and each $R^6$ and each $R^7$ optionally and independently selected from the group consisting of hydrogen, halogen, hydroxy, optionally substituted $C_{1-8}$-alkyl, $C_{1-8}$-alkoxy, optionally substituted $C_{1-8}$-alkylidene, optionally substituted $C_{2-8}$-alkenyl, optionally substituted $C_{2-8}$-alkynyl, optionally substituted aryl, optionally substituted heteroaryl, optionally substituted $C_{3-8}$-cycloalkyl, optionally substituted $C_{3-8}$-heterocyclyl, and optionally substituted $C_{1-8}$-alkylcarbonyl.

2. The compound of claim 1, wherein Z is N.

3. The compound of claim 2, wherein X is selected from the group consisting of N, S, and O.

4. The compound of claim 3, wherein —Y is =O.

5. The compound of claim 1, wherein R4' is selected from the group consisting of $C_{1-8}$-alkyl, $C_{1-8}$-alkoxy, $C_{3-8}$-cycloalkyl, $C_{1-8}$-alkylidene, each of which may be optionally substituted with a substituent $R^5$.

6. The compound of claim 1, wherein $R^4$ is selected from the group consisting of $C_{3-8}$-alkyl, $C_{3-8}$-alkoxy, and $C_{3-8}$-alkylidene, each of which may be optionally substituted with a substituent $R^5$ wherein $R^5$ is selected from the group consisting of hydrogen, halogen, hydroxy and $C_{1-8}$-alkyl.

7. The compound of claim 1, wherein $R^4$ is selected from the group consisting of an optionally substituted butyl, an optionally substituted pentyl, an optionally substituted propyloxy, and 3—($C_{1-8}$-alkyl)-butylidene.

8. The compound of claim 1, selected from the group consisting of:
   3-[3-(3-Butylidine-8-aza-bicyclo[3.2.1]oct-8-yl)-propyl]-3H-benzothiazol-2-one,
   3-[3-(3-Propyl-8-aza-bicyclo[3.2.1]oct-8-yl)-propyl]-3H-benzothiazol-2-one,
   3-[3-(3-Hexyl-8-aza-bicyclo[3.2.1]oct-8-yl)-propyl]-3H-benzothiazol-2-one,
   3-[3-(3-Butyl-8-aza-bicyclo[3.2.1]oct-8-yl)-propyl]-3H-benzothiazol-2-one, and
   3-[3-(3-Pentyl-8-aza-bicyclo[3.2.1]oct-8-yl)-propyl]-3H-benzothiazol-2-one.

9. A pharmaceutical composition comprising a compound according to claim 1, together with pharmaceutically acceptable carriers or excipients.

* * * * *